United States Patent
Chen et al.

(10) Patent No.: US 11,629,434 B2
(45) Date of Patent: Apr. 18, 2023

(54) ANTIBODY SCREENING METHODS

(71) Applicant: X-Body, Inc., Waltham, MA (US)

(72) Inventors: Yan Chen, Lexington, MA (US); Tod M. Woolf, Sudbury, MA (US); Richard W. Wagner, Cambridge, MA (US)

(73) Assignee: X-BODY, INC., Waltham, MA (US)

( * ) Notice: Subject to any disclaimer, the term of this patent is extended or adjusted under 35 U.S.C. 154(b) by 186 days.

(21) Appl. No.: 16/862,851

(22) Filed: Apr. 30, 2020

(65) Prior Publication Data

US 2020/0400657 A1 Dec. 24, 2020

Related U.S. Application Data

(62) Division of application No. 15/847,203, filed on Dec. 19, 2017, now Pat. No. 10,677,787, which is a division of application No. 14/005,085, filed as application No. PCT/US2012/029086 on Mar. 14, 2012, now Pat. No. 9,880,160.

(60) Provisional application No. 61/566,778, filed on Dec. 5, 2011, provisional application No. 61/453,106, filed on Mar. 15, 2011.

(51) Int. Cl.
| | |
|---|---|
| *C40B 30/04* | (2006.01) |
| *G01N 33/68* | (2006.01) |
| *C07K 16/00* | (2006.01) |
| *C07K 16/28* | (2006.01) |
| *G01N 33/543* | (2006.01) |
| *C40B 50/06* | (2006.01) |

(52) U.S. Cl.
CPC ............ *C40B 30/04* (2013.01); *C07K 16/005* (2013.01); *C07K 16/2863* (2013.01); *G01N 33/54306* (2013.01); *G01N 33/6854* (2013.01); *C07K 2317/21* (2013.01); *C07K 2317/56* (2013.01); *C07K 2317/622* (2013.01); *C40B 50/06* (2013.01)

(58) Field of Classification Search
None
See application file for complete search history.

(56) References Cited

U.S. PATENT DOCUMENTS

| | | |
|---|---|---|
| 2005/0255552 A1 | 11/2005 | Flynn et al. |
| 2006/0134098 A1 | 6/2006 | Bebbington et al. |
| 2010/0105569 A1 | 4/2010 | Hsieh et al. |

FOREIGN PATENT DOCUMENTS

| | | |
|---|---|---|
| CA | 2712298 A1 | 7/2009 |
| WO | WO 2008/130704 A2 | 10/2008 |
| WO | WO 2013/085972 A1 | 6/2013 |

OTHER PUBLICATIONS

Brezinschek et al. (1998) "Pairing of variable heavy and variable k chains in individual naive and memory B cells," The Journal of Immunology. 160(10):4762-4767.

(Continued)

*Primary Examiner* — Christian C Boesen
(74) *Attorney, Agent, or Firm* — Lathrop GPM LLP; James H. Velema, Esq.

(57) ABSTRACT

Provided are methods and compositions for the production of novel antibodies that bind specifically to a target antigen. These methods and compositions are particularly useful for producing antibodies having the antigen binding specificity of a reference antibody but with improved properties (e.g., binding affinity, immunogenicity, and thermodynamic stability) relative to the reference antibody.

10 Claims, 17 Drawing Sheets

Specification includes a Sequence Listing.

(56) References Cited

OTHER PUBLICATIONS

Chen et al. (2008) "Construction of a Large Phage-Displayed Human Antibody Domain Library with a Scaffold Based on a Newly Identified Highly Soluble, Stable Heavy Chain Variable Domain," J. Mol. Biol. 382(3):779-789.
Hur et al. (2010) "Development of the dual-vector system-III (DVS-III), which facilitates affinity maturation of a Fab antibody via light chain shuffling," Immunol. Let. 132(1-2):24-30.
International Search Report corresponding to International Patent Application No. PCT/US2012/029086, dated Mar. 28, 2013.
Kang et al. (1991) "Antibody redesign by chain shuffling from random combinatorial immunoglobulin libraries," Proc Natl Acad Sci USA. 88(1):11120-11123.
Supplementary European Search Report with Written Opinion corresponding to European Patent Application No. 12757543.9, dated May 11, 2015.
Written Opinion corresponding to International Patent Application No. PCT/US2012/029086, dated Mar. 28, 2013.

ANTIBODY SCREENING METHODS

RELATED APPLICATIONS

This application is a division of U.S. patent application Ser. No. 15/847,203, filed Dec. 19, 2017, which is a division of U.S. patent application Ser. No. 14/005,085, filed Dec. 24, 2013, now U.S. Pat. No. 9,880,160, which is the U.S. national stage of International Patent Application Serial No. PCT/US2012/029086, filed Mar. 14, 2012, which claims priority to U.S. Provisional Patent Application Serial Nos. 61/566,778, filed Dec. 5, 2011; and 61/453,106, filed Mar. 15, 2011, the entire disclosures of which are hereby incorporated herein by reference.

BACKGROUND

Monoclonal antibodies are hugely important as research tools, diagnostics and therapeutics. This is, in large part, due to the fact that monoclonal antibodies can be selected to bind with high specificity and affinity to almost any structural epitope.

Classical methods of immunizing animals to obtain antibodies are slow and cumbersome and, as a result, many in vitro selection techniques have been now developed. Examples of the techniques include nucleic acid display, phage display, retroviral display, and cell surface display (e.g., yeast, mammalian, and bacterial cells). In spite of these technological developments, it is still relatively difficult to obtain antibodies that possess the desired kinetic properties, selectivity, biophysical properties, and immunogenicity necessary for therapeutic use.

Accordingly, there is a need in the art for improved methods for the selection of antibodies against a desired target.

SUMMARY OF THE INVENTION

The invention provides methods and compositions for the production of novel antibodies that bind specifically to a target antigen. The invention is particularly useful for producing novel antibodies having the antigen binding specificity of a reference antibody but with improved properties (e.g., binding affinity, immunogenicity, and thermodynamic stability) relative to the reference antibody. In particular, the methods disclosed herein make it possible to rapidly generate an entirely novel antibody molecule starting only from a CDR3 of known antigen-binding specificity.

The disclosed methods also allow for the rapid identification of novel pairs of VH and VL domains having a high intrinsic thermostability. Prior art methods for selecting VH/VL binding pairs generally involve the enforced covalent linkage of VH and VL domains (e.g., as Fab or scFv fragments) and selection of VH/VL pairs based solely upon binding affinity of the linked VH and VL domains to a target antigen, without any being paid attention to the strength of non-covalent interaction between VH and VL domains. In contrast, the methods disclosed herein select stable VH/VL pairs based upon the strength of the non-covalent interaction between unpaired VH and VL domains (in addition to the binding affinity for a target antigen). As a result, the novel methods disclosed herein yield VH/VL pairs with greater intrinsic thermostability than those obtained using prior art methods.

Accordingly, in one aspect the invention provides a method for producing a V domain that binds specifically to a target antigen. The method generally comprises: (a) providing a library of chimeric, unpaired VH or VL domains wherein diversity lies in the FR1-FR3 regions of each domain, and wherein each member of the library comprises the CDR3 region sequence from a reference antibody that binds specifically to the antigen; (b) contacting the library with the antigen; and (c) selecting from the library at least one chimeric, unpaired VH or VL domain that binds specifically to the antigen, thereby producing a V domain that binds specifically to the antigen.

In certain embodiments, the method further comprises introducing additional amino acid sequence diversity into the library of step (a). In one embodiment, additional amino acid sequence diversity is introduced by random mutagenesis.

In certain embodiments, the method further comprises the step of (d) introducing additional amino acid sequence diversity into the VH or VL domain(s) selected in step (c).

In certain embodiments, the CDR3 region sequence is from a rodent, lagomorph, avian, camelid, shark, or human antibody.

In certain embodiments, each member of the library comprises an identical CDR3 region sequence.

In certain embodiments, the FR4 region sequences of said domains are human sequences.

In certain embodiments, the FR1-FR3 region sequences of the VH and VL domains are human sequences.

In certain embodiments, each member of the library comprises FR1-FR3 sequences encoded by a single human antibody VH or VL gene.

In certain embodiments, the library is a nucleic acid display library e.g., a dsDNA display library.

In another aspect, the invention provides library of chimeric, unpaired VH or VL domains wherein diversity lies in the FR1-FR3 regions of said domains, and wherein each member of the library comprises the CDR3 region sequence from the VH or VL domain of a reference antibody.

In certain embodiments, the CDR3 region sequence is from a rodent, lagomorph, avian, camelid, shark, or human antibody.

In certain embodiments, each member of the library comprises an identical CDR3 region sequence.

In certain embodiments, the FR4 region sequences of said domains are human sequences.

In certain embodiments, the FR1-FR3 region sequences of the VH and VL domains are human sequences.

In certain embodiments, each member of the library comprises FR1-FR3 sequences encoded by a single human antibody VH or VL gene.

In certain embodiments, the library is a nucleic acid display library e.g., a dsDNA display library.

In another aspect, the invention provides a method for selecting a stable VH/VL pair. The method generally comprises: (a) providing a VH domain that binds specifically to an antigen; (b) contacting the VH domain with a library of VL domains such that a library of VH/VL pairs is formed; (c) contacting the library of VH/VL pairs with the antigen; and (d) selecting from the library of VH/VL pairs at least one VH/VL pair that binds specifically to the antigen, thereby selecting a stable VH/VL pair.

In certain embodiments, the method further comprises the step of introducing additional amino acid sequence diversity into library of VL domains of step (b). In one embodiment, the additional amino acid sequence diversity is introduced by random mutagenesis.

In certain embodiments, the library of VL domains of step (b) comprises human VL domains.

In certain embodiments, the library of VL domains or VH/VL pairs is a nucleic acid display library, e.g., a dsDNA display library.

In certain embodiments, the complementary VH domain of step (a) is produced by the methods disclosed herein.

In another aspect, the invention provides a method for selecting a bispecific, stable VH/VL pair. The method generally comprises: (a) providing a VH domain that binds specifically to a first antigen; (b) contacting the VH domain with a library of VL domains such that a library of VH/VL pairs is formed; (c) contacting the library of VH/VL pairs with a second antigen; (d) selecting from the library of VH/VL pairs at least one VH/VL pair that binds specifically to the second antigen; and (e) contacting the VH/VL pair(s) selected in step (d) with the first antigen; and (f) selecting at least one VH/VL pair that binds specifically to the first antigen, thereby selecting a bispecific, stable VH/VL pair.

In certain embodiments, the method further comprises the step of introducing additional amino acid sequence diversity into library of VL domains of step (b). In one embodiment, the additional amino acid sequence diversity is introduced by random mutagenesis.

In certain embodiments, the library of VL domains of step (b) comprises human VL domains.

In certain embodiments, the library of VL domains or VH/VL pairs is a nucleic acid display library, e.g., a dsDNA display library.

In certain embodiments, the complementary VH domain of step (a) is produced by the methods disclosed herein.

DETAILED DESCRIPTION

Figure 1:
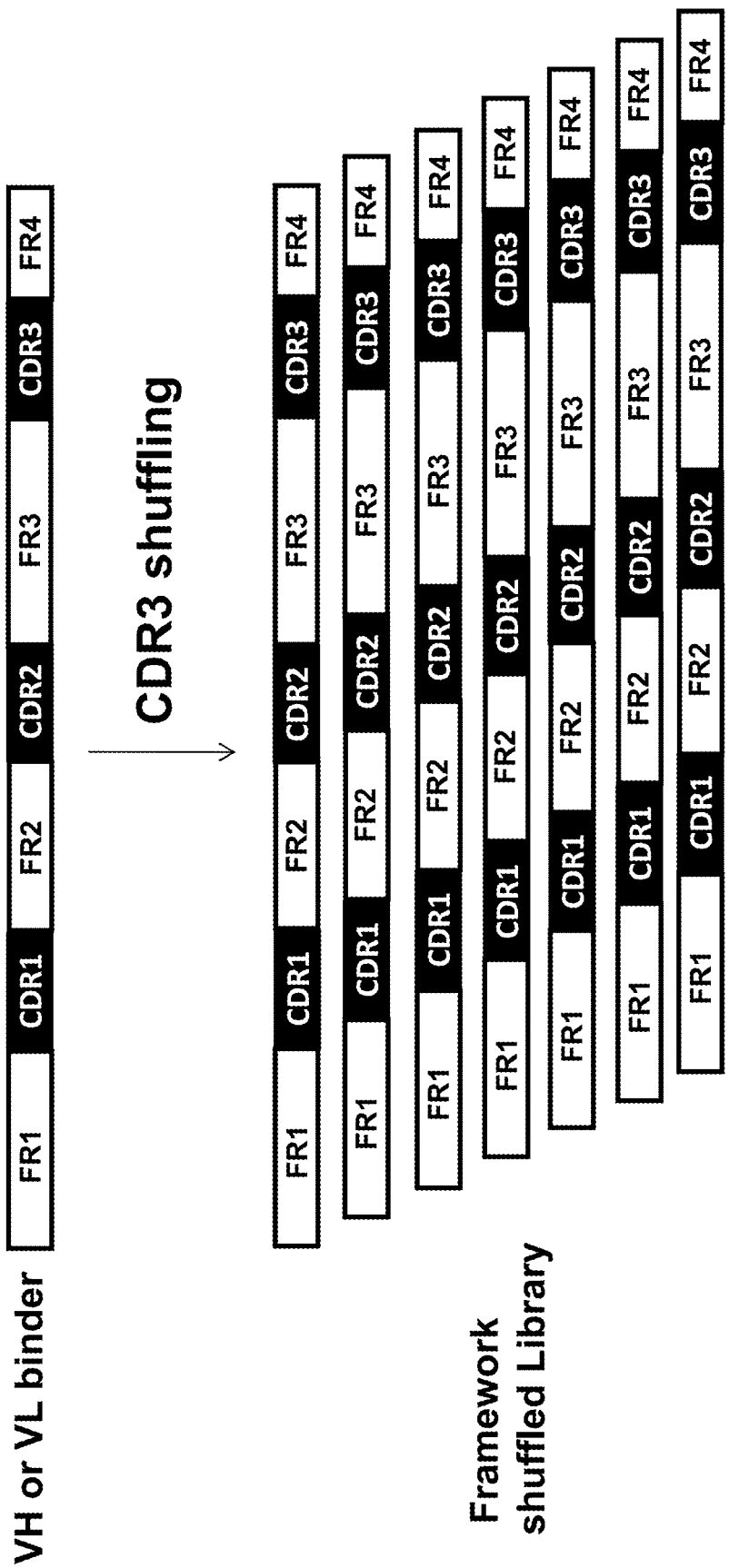
FIG. 1 is a schematic representation of exemplary CDR3/framework shuffling methods as disclosed herein.

The invention provides methods and compositions for the production of novel antibodies that bind specifically to a target antigen. The invention is particularly useful for producing antibodies having the antigen binding specificity of a reference antibody but with improved properties (e.g., binding affinity, immunogenicity, and thermodynamic stability) relative to the reference antibody.

I. DEFINITIONS

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see e.g., Kabat et al. (1991) Sequences of Proteins of Immunological Interest. (NIH Publication No. 91-3242, Bethesda). The CDR boundaries can be defined using any art recognized numbering system.

As used herein, the term "V domain" refers to a single polypeptide comprising a VH domain or VL domain that is devoid of constant region sequences that facilitate the covalent pairing of said VH domain or VL domain with a complementary VL domain or VH domain, respectively.

As used herein, the term "FR1-FR3" refers to the region of a VH encompassing FR1, CDR2, FR2, CDR2 and CDR3, but excluding the CDR3 and FR4 regions.

As used herein, the term "chimeric" refers to an antibody variable domain comprising amino acid sequences from two or more different antibody variable domain, e.g., a variable domain with CDR3 sequences from a reference antibody and FR1-FR3 sequences from one or more different antibodies.

As used herein, the term "unpaired" refers to VH or VL that are not linked (either covalently or non-covalently) to a complementary VL or VH domain, respectively.

As used herein, the term "complementary VL or VH domain" refers to a VL or VH domain that associates with a VH or VL domain, respectively, to form a VH/VL pair.

As used herein, the term "VH/VL pair" refers to a non-covalent dimer of a single VH and a single VL domain, wherein the VL and VH domains are associated through the natural VH/VL dimer interface in a similar manner to that observed in a complete, tetrameric immunogobulin molecule, and the dimer can bind specifically to at least one target antigen. A "stable VH/VL pair" is a VH/VL pair that does not exhibit significant dissociation of the substituent VH and VL domains under physiological conditions.

As used herein, the term "bispecific" refers to a VH/VL pair, wherein the VH and the VL domains bind to different antigens.

As used herein, the term "nucleic acid display library" refers to any art recognized in vitro cell-free phenotype-genotype linked display, including, without limitation those set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315, and in WO2010/011944, which are all hereby incorporated by reference in their entirety.

As used herein, the term "specifically binds to" refers to the ability of a binding molecule (e.g., a VH or VL domain) to bind to an antigen with an affinity of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or bind to a target with an affinity that is at least two-fold greater than its affinity for a nonspecific antigen.

As used herein, the term "antigen" refers to the binding site or epitope recognized by a binding molecule (e.g., a VH or VL domain).

As used herein, the term "reference antibody" refers to any antibody that binds specifically to an antigen of interest.

As used herein, the term "antibody" refers to IgG, IgM, IgA, IgD or IgE or an antigen-binding fragment thereof (e.g. VH and/or VL), whether derived from any species naturally producing an antibody, or created by recombinant DNA technology.

II. METHODS FOR CDR3/FRAMEWORK SHUFFLING OF ANTIBODY VARIABLE DOMAINS

In one aspect, the invention provides a method for producing a V domain that binds specifically to a target antigen. This method allows for the rapid generation of an entirely novel antibody molecule starting only from a CDR3 of known antigen-binding specificity. The method generally comprises the steps of: (a) providing a library of chimeric, unpaired VH or VL domains wherein diversity lies in the FR1-FR3 regions of each domain, and wherein each member of the library comprises a CDR3 region sequence that binds specifically to the antigen; (b) contacting the library with the antigen; and (c) selecting from the library at least one chimeric, unpaired VH or VL domain that binds specifically to the antigen.

The CDR3 region sequence can be artificial, naturally derived, or a combination thereof. Naturally derived CDR3 region sequences can be from any organism that produces an antibody including, but not limited to, rodent, lagomorph, avian, camelid, shark, or human.

The CDR3 sequence can be from an antibody heavy chain or a light chain. However, the skilled worker will appreciate that the CDR3 must match the V-domain context into which it is placed e.g., a heavy chain CDR3 should be used in a VH domain library and a light chain CDR3 should be used in a VL domain library.

In certain embodiments, the library contains a single species of CDR3 sequence. In a particular embodiment, the CDR3 sequence is from a single reference antibody that binds to the target antigen. In other embodiments, the library contains multiple species of CDR3 sequence. In a particular embodiment, the multiple species of CDR3 sequence are variants of a single CDR3 sequence from a single reference antibody. Such variants can be produced by alteration (e.g. substitution, addition, deletion and/or modification) of at least one amino acid in the CDR3 sequence from the reference antibody. Alterations can be generated randomly (e.g., by random mutagenesis) or in a site-directed fashion using any art recognized means.

In general, the library comprises a diversity plurality of diverse FR1-FR3 region amino acid sequences. The plurality of FR1-FR3 region amino acid sequences can be from any source including, without limitation, naturally-occurring variable regions (e.g, from the antibody VH or VL gene repertoire of an animal), artificial antibody variable regions, or a combination thereof. In certain embodiments, each member of the library comprises FR1-FR3 sequences encoded by a single antibody VH or VL gene (e.g., a human VH or VL gene). In other embodiments, the FR1-FR3 region sequences are human sequences. In a particular embodiment, the FR1-FR3 region sequences are naturally-occurring human antibody variable region sequences from the B-cells of healthy donors.

In certain embodiments, the V domain further comprises an FR4 region. The FR4 region can be from the reference antibody or from another source. Suitable sources include, without limitation, naturally occurring human antibody variable regions, artificial antibody variable regions, or a combination thereof.

The V-domain library can be generated using any art recognized methods including, without limitation, ab initio nucleic acid synthesis and DNA or RNA polymerase-mediated assembly. In a preferred embodiment, the library is assembled by PCR using overlapping oligonucleotides. Suitable oligos for assembling a VH domain library include those set forth in SEQ ID No: 4-21. Suitable oligos for assembling a VL domain library include those set forth in SEQ ID No: 70-102.

The chimeric, unpaired VH or VL domain(s), selected using the methods of invention, can be paired with a complementary VL or VH, respectively, to generate a VH/VL pair using the methods disclosed herein.

III. METHODS FOR IDENTIFICATION OF STABLE VH/VL PAIRS

In another aspect, the invention provides a method for selecting stable VH/VL pairs. This method selects stable VH/VL binding pairs based upon the strength of the non-covalent interaction between unpaired VH and VL domains and allows for the rapid identification of novel pairs of VH and VL domains having a high intrinsic thermostability. The method generally comprises the steps of: (a) providing a VH domain that binds specifically to an antigen; (b) contacting the VH domain with a library of VL domains such that a library of VH/VL pairs is formed; (c) contacting the library of VH/VL pairs with the antigen; and (d) selecting from the library of VH/VL pairs at least one VH/VL pair that binds specifically to the antigen.

The VH domain that is used to screen for stable VH/VL pairs can be from any source (artificial, naturally derived, or a combination thereof). In certain embodiments, the VH domain is a from a reference antibody. In other embodiments, the VH domain is a chimeric VH domain selected using the CDR3/Framework methods disclosed herein.

The library of VL domains that is used to screen for stable VH/VL pairs can be from any source (artificial, naturally derived, or a combination thereof). In certain embodiments, the library of VL domains is a human VL domain library. In a particular embodiment, the human VL domain library comprises naturally-occurring human antibody VL region sequences from the B-cells of healthy donors. The VL domain libraries disclosed herein are particularly suitable for use in these methods.

Although it is preferred to screen a library of VL domains using a VH domain as the bait, the skilled worker will appreciate that it is entirely within the scope of the invention to perform the converse screen i.e., to screen a library of VH domains using a VL domain as the bait. This method general comprises that steps of: (a) providing a VL domain that binds specifically to an antigen; (b) contacting the VL domain with a library of VH domains such that a library of VH/VL pairs is formed; (c) contacting the library of VH/VL pairs with the antigen; and (d) selecting from the library of VH/VL pairs at least one VH/VL pair that binds specifically to the antigen, thereby selecting a stable VH/VL pair.

In another aspect, the invention provides, a method for selecting a stable VH/VL pair, wherein the method generally comprises: (a) providing a first nucleic acid display library of VH domains, wherein members of the library comprise a VH domain linked to its cognate nucleic acid coding sequence; (b) providing a second nucleic acid display library of VL domains, wherein members of the library comprise a VL domain linked to its cognate nucleic acid coding sequence; (c) contacting the first nucleic acid display library with the second nucleic acid display library such that a library of VH/VL pairs is formed; (d) contacting the library of VH/VL pairs with an antigen; and (e) selecting from the library of VH/VL pairs at least one VH/VL pair that binds specifically to the antigen, and, (f) ligating together the nucleic acid coding sequences of the VH and VL domains in the VH/VL pairs selected in step (e). This method is particularly advantageous in that it allows for the simultaneous screening of VH and VL domain libraries and the precise determination of the sequences of the VH and VL domains in each selected, stable VH/VL pair.

The nucleic acid coding sequences in each selected VH/VL pair can be ligated together using any appropriate art recognized means (e.g., chemical and/or enzymatic). RNA can be ligated with, for example, RNA ligase. DNA can be ligated, with, for example, DNA ligase. Ligation of the VH and VL domain nucleic acid coding sequences can be facilitated by the use of, for example, nucleic acid linkers, adaptors and/or restriction enzyme digestion. In certain embodiments, the nucleic acid coding sequences of the VH and VL domain in each selected VH/VL pair are ligated together to form a single, continuous nucleic acid sequence (linear or circular), and the VH and VL domain sequences present in the continuous nucleic acid sequence are determined. Nucleic acid sequence determination can achieved by any art-recognized means, including without limitation, single molecule DNA sequencing.

The above methods for identification of stable VH/VL pairs are particularly suitable for use in combination with the CDR3/framework shuffling methods disclosed herein. This combination of methods allows selection of a novel, stable VH/VL pair specific for a target antigen using only an antigen-specific CDR3 sequence as a starting point.

The methods of the invention are particularly useful for screening for stable VH/VL pairs. However, one skilled in the art will appreciate that the invention can be used more broadly to screen for any stable protein dimer, wherein at least one monomer of the dimer binds to a ligand. Suitable protein dimers include, without limitation, immunoglobulin superfamily members (e.g., T-cell receptors), hormones, cytokines, transcription factors, and the like.

IV. METHODS OF PRODUCING BISPECIFIC ANTIBODIES

In another aspect, the invention provides a method for selecting a bispecific, stable VH/VL pair, (e.g., a VH/VL pair in which the VH and VL domains bind to two different antigens). The method generally comprises the steps of: (a) providing a VH domain that binds specifically to a first antigen; (b) contacting the VH domain with a library of VL domains such that a library of VH/VL pairs is formed; (c) contacting the library of VH/VL pairs with a second antigen; (d) selecting from the library of VH/VL pairs at least one VH/VL pair that binds specifically to the second antigen; and (e) contacting the VH/VL pair(s) selected in step (d) with the first antigen; and (f) selecting at least one VH/VL pair that binds specifically to the first antigen.

In one embodiment, the first and second antigens are different epitopes present in a single molecule. In another embodiment, the first and second antigens are epitopes present in two separate molecules.

In certain embodiments, it is desirable to select for a promiscuous light chain that can bind to at least two different VH domains (with different antigen specificities) but that cannot, itself, specifically bind to an antigen (e.g., has a low affinity for all antigens). Such light chains are particularly useful in that they can be used in the assembly of full-length, bispecific, heterotetrameric antibodies. These bispecific antibodies generally comprising a first heavy chain with a first antigen specificity, a second heavy chain with second antigen specificity, and two molecules of the selected promiscuous light, wherein each heavy chain is paired with a different promiscuous light chain molecule.

V. LIBRARY SCREENING METHODS

The skilled worker will appreciate that any type of VH or VL domain expression library can be employed in the methods of the invention. Suitable expression libraries include, without limitation, nucleic acid display, phage display, retroviral display, and cell surface display libraries (e.g., yeast, mammalian, and bacterial cells). In certain embodiments, the library is a nucleic acid display library. In a preferred embodiment, the nucleic acid display library is a DNA-display library constructed as exemplified herein or in WO2010/011944, which is hereby incorporated by reference in its entirety.

Methods for screening expression libraries are well known in the art. See, for example, Antibody Engineering: Methods and Protocols. Methods in Molecular Biology Volume 248, (B.K.C. Lo, Ed) Humana Press, 2004 (ISBN: 1-58829-092-1), which is hereby incorporated by reference in its entirety. Suitable methods of screening nucleic acid display libraries, include, without limitation those set forth in U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489, 116; 6,436,665; 6,537,749; 6,602,685; 6,623,926; 6,416,950; 6,660,473; 6,312,927; 5,922,545; and 6,348,315, and in WO2010/011944, which are all hereby incorporated by reference in their entirety. In a preferred embodiment, the screening of nucleic acid-display libraries is performed as exemplified herein or in WO2010/011944.

The methods of the invention are particularly well suited to generating VH or VL domains, and/or VH/VL pairs that bind to a target antigen with high affinity. To enhance affinity for the antigen, multiple rounds of library screening can be performed, with additional amino acid sequence diversity being introduced at each screening round, if desired. If desired, the stringency of the method can be enhanced by altering the assay conditions to reduce the affinity of the VH or VL domains for the antigen, for example, by altering the pH and/or salt concentration of the antigen binding reaction. Such methods selectively enrich for VH or VL domains with the highest affinity and stability.

The methods of the invention also allow for selection of VH or VL domains, and/or VH/VL pairs having a different antigen specificity to that of a starting reference antibody. For example, the HCDR3 from an antibody that only binds to human PDGFRβ can be used to select for a VH domain, and/or VH/VL pair that binds to both human and mouse PDGFRβ. Such a selection is exemplified in Example 2 herein.

In certain embodiments, additional amino acid sequence diversity is introduced into the VH or VL domain library, or the VH or VL domain(s) selected from the library. Amino acid sequence diversity can be introduced by any art-recognized means. In certain embodiments, amino acid sequence diversity is introduced by alteration of the nucleic acid sequence(s) encoding the VH or VL domain library, or the VH or VL domain. In certain embodiments amino acid sequence diversity is introduced by random mutagenesis. Such random mutagenesis can be achieved, for example, by low-fidelity PCR amplification of the nucleic acid sequence(s) encoding the VH or VL domain library, or the VH or VL domain.

VI. ANTIBODY FORMATS

The VH and/or VL domains employed in the methods of the invention can be used in isolation or fused to additional amino acids (e.g., epitope tags) and/or domains. In certain embodiments, at least one VH domain in a library is fused to at least one CH1 domain, CH2 domain, CH3 domain or a combination thereof. In a particular embodiment, at least one VH domain in a library is fused to at least one heavy chain constant region comprising at least one CH1 domain, CH2 domain and CH3 domain. In certain embodiments, at least one VL domain in a library is fused to at least one light chain constant region.

VH or VL domains, and/or VH/VL pairs selected using the methods of the invention can be incorporated into another antibody format including, without limitation, scFv, Fab, and/or complete tetrameric antibody.

VII. EXAMPLES

The present invention is further illustrated by the following examples which should not be construed as further limiting. The contents of Sequence Listing, figures and all references, patents and published patent applications cited throughout this application are expressly incorporated herein by reference.

Example 1. Isolation of VH Domains that Bind Specifically to Human PDGFRβ

VH domains that bind specifically to human PDGFRβ were selected using DNA display as set forth in WO2010/011944, which is hereby incorporated by reference in its entirety. Specifically, a naïve, human VH domain DNA display library containing derived from 10 bone marrow donors was subject to six rounds of selection against human PDGFRβ. The selected binders were cloned and sequenced. From this screen VH domain clones A4, B4 and G2 were selected, the amino acid sequences of which are set forth in Table 1.

TABLE 1

Amino acid sequences of exemplary PDGFRβ-binding VH domains.

| Clone name | VH Amino Acid Sequence | SEQ ID NO. |
|---|---|---|
| A4 XB1511 | QVQLVQSGAEVKKPGSSVKVSCKASGGTFSSYAI SWVRQAPGQGLEWMGGIIPIFGTANYAQKFQGRV TITADESTSTAYMELSSLRSEDTAVYYCAIHGGD RSYWGQGTLVTVSS | 1 |
| B4 | QVQLVQSGAEVKKPGASVKVSCKASGYTFTSYAI SWVRQAPGQGLEWMGGIIPIFGTANYAQKFQGRV TITADESTSTAYMELSSLRSEDTAVYYCAIHGGD RSYWGQGTLVTVSS | 2 |
| G2 | QVQLVQSGAEVKKPGASVKVSCKASGYTFTGYAI SWVRQAPGQGLEWMGGIIPIFGTANYAQKFQGRV TITADESTSTAYMELSSLRSKDTAVYYCAIHGGD RSYWGQGTLVTVSS | 3 |

Example 2. HCDR3 Shuffling

A. VH Library Construction

Figure 2:
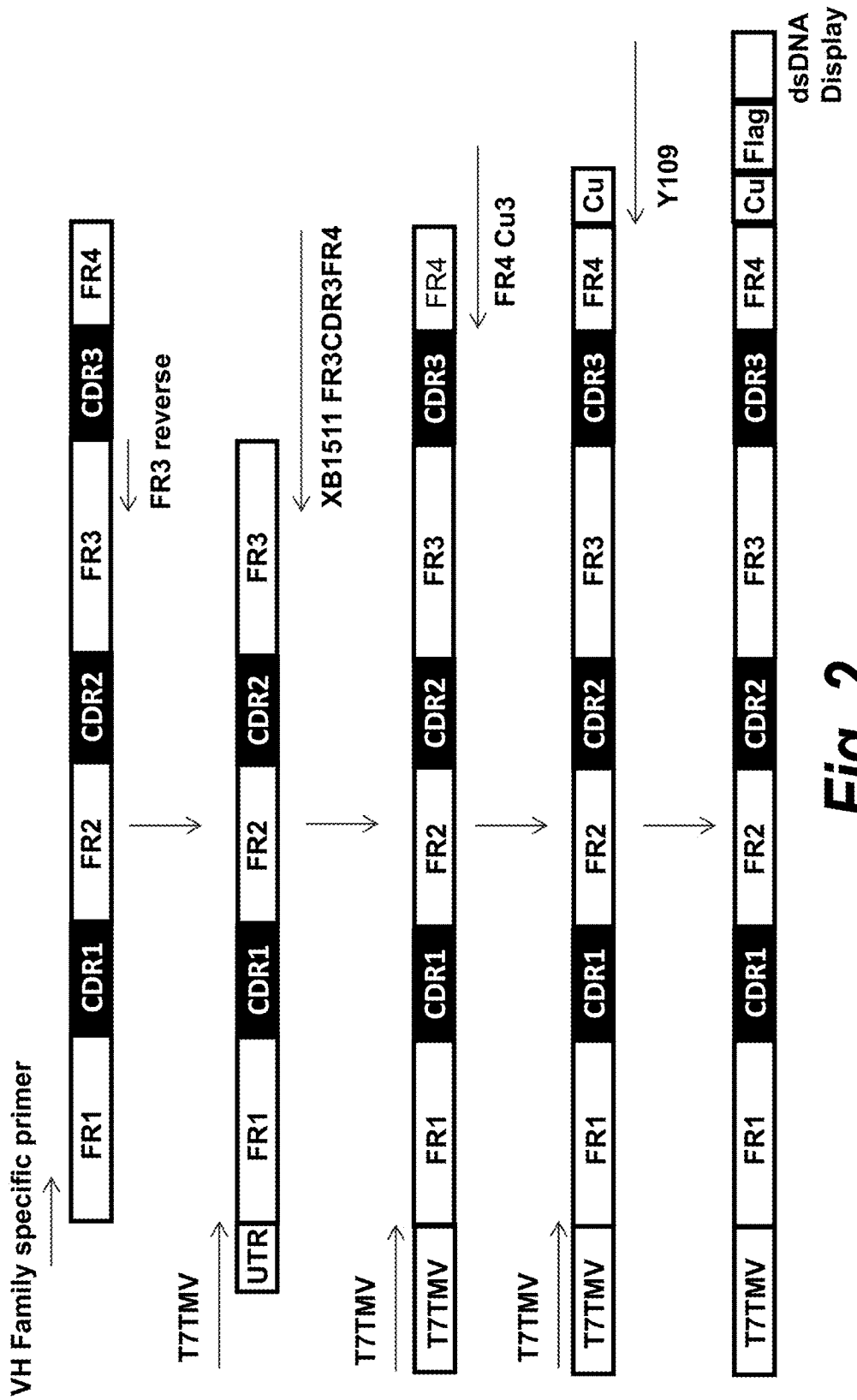
FIG. 2 is a schematic representation of the construction of exemplary VH nucleic acid display libraries for use in the disclosed methods.

To screen for VH domains with improved binding characteristics, the HCDR3 sequence of clone A4 (designated XB1511) was shuffled into a naïve human VH library, which was further selected for binding to human and mouse PDGFRβ. Specifically, the DNA sequence coding for the HCDR3 of clone A4 (SEQ ID NO: 1) was synthesized and assembled into a library comprising framework regions 1-3 of naïve human VH domains amplified from bone marrow B cells and PBMCs using framework specific oligonucleotides. Human VH framework regions 1-3 were amplified using 5' VH family-specific and 3' generic FR3 reverse primers to create separate libraries of VH family framework regions. The VH family framework libraries and the XB1511 HCDR3 were shuffled by further PCR amplification using 5' T7TMV and 3' XB1511 FR3CDR3FR4 oligos. This also added a T7TMV promoter sequence at the 5' end for in vitro transcription/translation. A C-terminal Cµ3 sequence and a FLAG tag (for purification after translation) were also added by PCR using FR4 Cu3 Reverse and Y109 primers, respectively, together with the 5' T7TMV primer. The nucleic acid sequences of the oligonucleotides used for preparation of the HCDR3-shuffled VH library are set forth in Table 2. A schematic representation of the general concept of CDR3/framework shuffling is set forth is FIG. 1, and a schematic representation of the VH library construction is set forth in FIG. 2.

TABLE 2

Oligonucleotides for constructing HCDR3 shuffled VH libraries

| Oligo | Sequence | SEQ ID NO. |
|---|---|---|
| FR3 Reverse | CGCACAGTAATACACGGC | 4. |
| VH1a | CAATTACTATTTACAATTACAATGCAGGTKCAGCTGGTGCAGTCTG | 5. |
| VH1b | CAATTACTATTTACAATTACAATGCAGGTCCAGCTTGTGCAGTCTG | 6. |
| VH1c | CAATTACTATTTACAATTACAATGSAGGTCCAGCTGGTACAGTCTG | 7. |
| VH1d | CAATTACTATTTACAATTACAATGCARATGCAGCTGGTGCAGTCTG | 8. |
| VH2 | CAATTACTATTTACAATTACAATGCAGRTCACCTTGAAGGAGTCTG | 9. |
| VH3a | CAATTACTATTTACAATTACAATGGARGTGCAGCTGGTGGAGTCTG | 10. |
| VH3b | CAATTACTATTTACAATTACAATGCAGGTGCAGCTGGTGGAGTCTG | 11. |
| VH3c | CAATTACTATTTACAATTACAATGGAGGTGCAGCTGTTGGAGTCTG | 12. |
| VH4a | CAATTACTATTTACAATTACAATGCAGSTGCAGCTGCAGGAG | 13. |
| VH4b | CAATTACTATTTACAATTACAATGCAGGTGCAGCTACAGCAGTGG | 14. |
| VH5 | CAATTACTATTTACAATTACAATGGARGTGCAGCTGGTGCAGTCTG | 15. |
| VH6 | CAATTACTATTTACAATTACAATGCAGGTACAGCTGCAGCAGTCAG | 16. |
| VH7 | CAATTACTATTTACAATTACAATGCAGGTGCAGCTGGTGCAATCTG | 17. |
| T7TMVUTR | TAATACGACTCACTATAGGGACAATTACTATTTACAATTACA | 18. |
| XB1511 FR3CDR3FR4 Reverse | TGAGGAGACGGTGACCAGGGTTCCCTGGCCCCAGTAGCTCCTGTCG CCCCCATGTKTCGCACAGTAATACACGGC | 19. |
| FR4 Cu3 Reverse | GGAGACGAGGGGGAAAAGGGTTGAGGAGACGGTGACCAG | 20. |
| Y109 | TTTTTTTTTTTTTTTTTTTAAATAGCGGATGCTAAGGACGACTTG TCGTCGTCGTCCTTGTAGTCGGAGACGAGGGGGAAAAGGGT | 21. |

B. Library Screening

Figure 3:
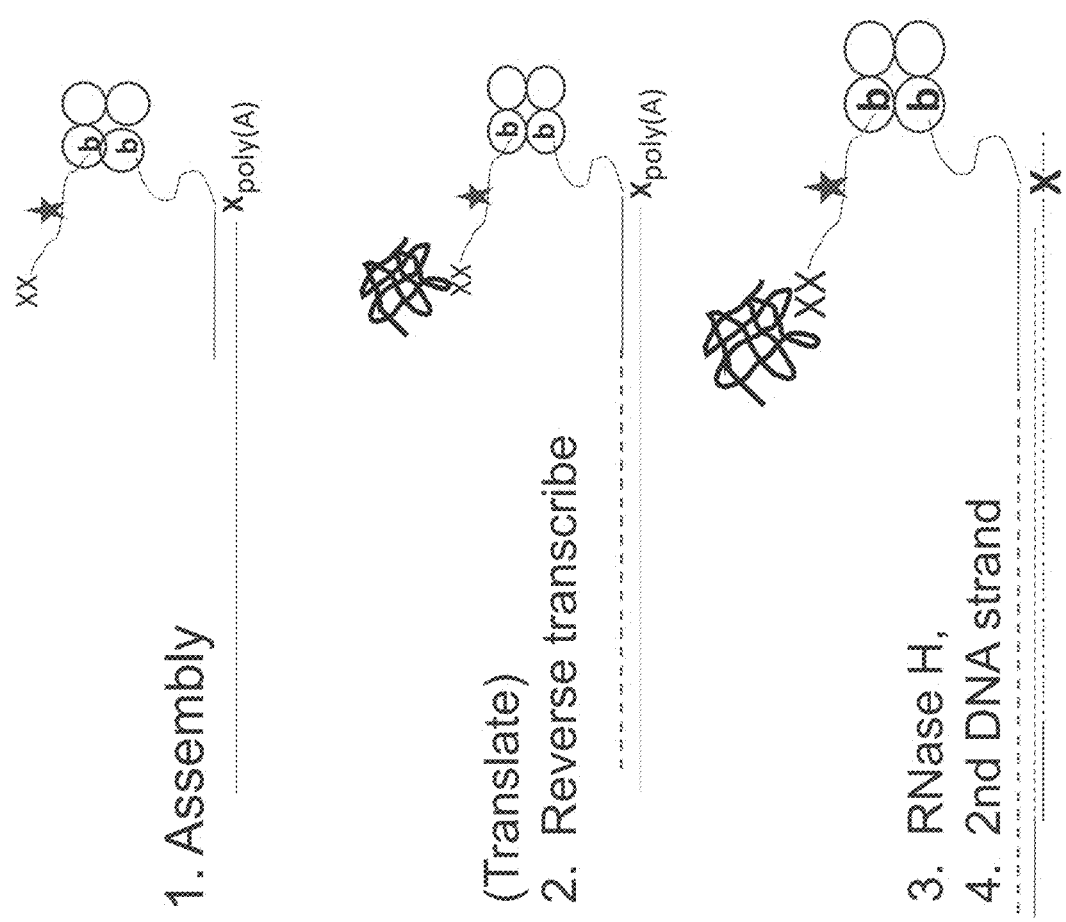
FIG. 3 is a schematic representation of exemplary nucleic acid display methods for use in the disclosed methods. The letter "b" represents biotin and the circles represent a tetrameric biotin binding molecule.

The HCDR3 shuffled VH domain library was then transcribed into an mRNA library and subjected to selection with dsDNA display technology as set forth in WO2010/011944. A schematic representation of the screening method is set forth in FIG. 3. The selection was carried out with human and mouse PDGFRβ at alternate round for 4 rounds. Kinetic controlled on and off rate selection was applied at successive rounds to increase the stringency of the selection to improve the affinity. Specifically, selection was performed as follows: Round 1 (R1) with 10 nM of immobilized human PDGFRβ; R2 with immobilized 100 nM mouse PDGFRβ; R3 with 10 nM soluble human PDGFRβ and competed with 200 nM immobilized human PDGFRβ for 24 hours and 120 hours; and R4 with 10 nM mouse PDGFRβ. The R4 binding pool was subcloned for DNA sequencing. Analysis of the sequences of the R4 binding pool showed that the HCDR3 of XB1511 was present in a variety of different framework contexts. No wild type parental sequence was obtained from the set of sequences analyzed. The amino acid sequences of the selected VH domains are set forth in Table 3.

TABLE 3

Amino acid sequences of exemplary PDGFRβ-binding VH domains selected from HCDR3 shuffled VH libraries.

| Clone name | VH Amino Acid Sequence | SEQ ID NO. |
|---|---|---|
| | XB1511 framework shuffled and selected with 2 rounds on human and 2 rounds on mouse PDGFRβ targets | |
| XB2202 | QVQLVQSGAEVKKPGSSVRVSCKASGGTFSRHAISWVRQAPGQG LEWIGGILPILKTPNYAQRFQGRVTINADESTSTVYMEMSSLRS EDTAVYYCATHGGDRSYWGQGTLVTVSS | 22. |

TABLE 3-continued

Amino acid sequences of exemplary PDGFRβ-binding VH domains selected from HCDR3 shuffled VH libraries.

| Clone name | VH Amino Acid Sequence | SEQ ID NO. |
|---|---|---|
| C4. | QMQLVQSGAEVKKPGSSVRVSCKAGGTFSRHAISWVRQAPGQG LEWIGGILPILKTPNYAQRFQGRVTINADESTSTVYMEMSGLRS EDTAVYYCATHGGDRSYWGQGTLVTVSS | 23. |
| B12. | QMQLVQSGAEVKKPGSSVRVSCKASGGTFSRHAISWVRQAPGQG LEWIGGILPILKTPNYAQRFQGRVTINADESTSTVYMEMSSLRS ENTAVYYCATHGGDRSYWGQGTLVTVSS | 24. |
| D07. | QMQLVQSGAEVKKPGSSVRVSCKASGGTFSRHAISWVRQAPGQG LEWIGGILPILKTPNYAQRFQGRVTINADESTSTVYMEMSSLRS DDTAVYYCATHGGDRSYWGQGTLVTVSS | 25. |
| C05. | QMQLVQSGAEVKKPGSSVRVSCKASGGTFSRHAISWVRQAPGQG LEWIGGVLPILKTPNYAQRFQGRVTINADESTSTVYMELSSLRS EDTAVYYCATHGGDRSYWGQGTLVTVSS | 26. |
| E05. | QVQLVQSGPKVKKPGSSVRVSCKASGGTFSRHAISWVRQAPGQG LEWIGGILPILKTPNYAQRFQGRVTINADESTSTVYMEMSSLRS EDTAVYYCATHGGDRSYWGQGTLVTVSS | 27. |
| E2. | QMQLVQSGAEVKKPGASVKISCKTSGYTFTDYYIQWVRQAPGQG LEWVGWINPNSGNTGYAQKFQGRVTMTRDTSISTAYMELSSLRS EDTAVYYCATHGGDYSYWGQGTLVTVSS | 28. |
| A3. | QVQLVQSGAEVKKPGASVRVSCKASGYTFSDYYIQWVRQAPGQG LEWMGWINPNSGGTYFAQKFQGRVTMTRDTSISTAYMELSSLTS DDTAVYYCATHGGDRGYWGQGTLVTVSS | 29. |
| C3. | QMQLVQSGAEVKKPGASVKVSCKASGYTFTDYYIQWVRQAPGQG LEWIGGILPILKTPNYAQRFQGRVTINADESTSTVYMEMSSLRS EDTAVYYCATHGGDRSYWGQGTLVTVSS | 30. |
| F10. | QMQLVQSGAEVKKPGASVKVSCKASGYTFTDYYIQWVRQAPGQG LEWMGWINPDSGGTYFAQKFQGRVAMTRDTSINTAYMELSSLRS DDTAVYYCATHGGDRSYWGQGTLVTVSS | 31. |
| C12. | QVQLVQSGAEVKKPGASVKVSCKASGYTFTDYYIQWVRQAPGEG LEWMGWMNPDSGGTIYAQKFQGRVTMTRDTSISTAYMELSRLRP DDTAVYYCATHGGDRSYWGQGTLVTVSS | 32. |
| H2. | QMQLVQSGAEVKNPGASVKVSCKASGYPFSAYYIQWVRQAPGQG LEWMGWLNPNSGDTHSAQKFQGRVTMTRDTSISTAYMELSGLTS DDTAVYYCATHGGDRSYWGQGTLVTVSS | 33. |
| F11. | QMQLVQSGAEVKNPGASVKVSCKASGYPFSAYYIQWVRQAPGQG LEWMGWLNPNSGDTHSAQKFQGRVTMTRDTSISTAYMELSGPTS DDTAVYYCATHGGDRSYWGQGTLVTVSS | 34. |
| B1. | QMQLVQSGAEVRKPGASVKVSCKASGYSFSDYYIHWVRQAPGQG LEWIGWINPNNGNTTYAQKFQGRVTMIRDTSISTAYMELSELRS DDTAVYYCATHGGDRSYWGQGTLVTVSS | 35. |
| E11. | QVQLVQSGAEVEKPGASVKVSCKASGYTFTDYYIHWVRQAPGQG LEWMRGIIPIFGTANYAQKFQGRVTITADESTSTAYMELSSLRS EDTAVYYCATHGGDRSYWGQGTLVTVSS | 36. |
| H1. | EVQLLESGAEVKQPGASVKVSCKTSGYTFTDYHLHWVRQAPGQG LEWMGWINPNSGGTNSAPKFQGRVTMTRDTSISTAYMELSGLTS DDTAVYYCATHGGDRSYWGQGTLVTVSS | 37. |
| E6. | QMQLVQSGAEVKRPGASVKVPCKASGYTFTDYYLHWVRQAPGQG LKWMGWINPNSGGTNYAQKFQGRVTMTRDTSISTAYMELSRLRS EDTAVYYCATHGGDRSYWGQGTLVTVSS | 38. |
| A1. | QVQLVQSGPEVKKPGTSVKVSCKASGFTFTSSAVQWVRQARGQR LEWIGWIVVGSGNTNYAQKFQERVTITRDMSTSTAYMELSSLRS EDTAVYYCATHGGDRSYWGQGTLVTVSS | 39. |
| H7. | QVQLVQSGPEVKKPGTSVKVSCKASGFTFTSSAMQWVRQARGQR LEWIGWIVVGSGNTNYAQKFQERVTITRDMSTSTAYMELSSLRS EDTAVYYCATHGGDRSYWGQGTLVTVSS | 40. |

TABLE 3-continued

Amino acid sequences of exemplary PDGFRβ-binding VH domains selected from HCDR3 shuffled VH libraries.

| Clone name | VH Amino Acid Sequence | SEQ ID NO. |
|---|---|---|
| G04. | QVQLVQSGAEVKKPGASVKVSCKASGFTFTSYAISWVRQARGQR LEWIGWIVVGSGNTNYAQKFQERVTITRDMSTSTAYMELSSLRS EDTAVYYCATHGGDRSYWGQGTLVTVSS | 41. |
| B2. | QVQLVQSGAEVKKPGASVKVSCKASGYSFTNYQVQWVRQAPGQG LEWLGVINTGVGSTNYAQKFQGRVTMTRDTATSTVYMELSSLRS EDTAVYYCATHGGDRSYWGQGTLVTVSS | 42. |
| A7. | QVQLVQSGAEVKKPGASVKVSCKASGYSFTNYPVQWVRQAPGQG LEWLGVINTGVGSTNYAQKFQGRVTMTRDTATSIVYMELSSLRS EDTAVYYCATHGGDRSYWGQGTLVTVSS | 43. |
| H3. | QVQLVQSGAEVKKPGASVKVSCRASGYTFTNSFMQWVRQVPGQR LEWVGLSNPSGDYTVYAPKFQGRVTMTTDTATSTFYMELFSLRS DDTAVYYCATHGGDRSYWGQGTLVTVSS | 44. |
| B4. | QVQLVQSGAEVKKPGASVKVSCRASGYTFTNSFMQWVRQVPGQR LEWVGLSNPSGDYTVYAPKLQGRVTMTTDTATGTFYMELFSLRS DDTAVYYCATHGGDRSYWGQGTLVTVSS | 45. |
| H05. | EVQLVQSGGGVVQPGGSLRLSCAASGFTFRSYGMHWVRQAPGKG LEWVAFILFDGNNKYYADSVKGRFTISSDNSKNTLYLQMNSLRA EDTAVYYCATHGGDRSYWGQGTLVTVSS | 46. |
| D06. | QVQLVQSGGGVVQPGRSLRLSCAASGFTSSYGMHWVRQAPGKG LEWVAVISYDGSNKYYADSVKGRFTISRDNSKNTLYLQMNSLRA EDTAVYYCAKHGGDRSYWGQGTLVTVSS | 47. |
| F3. | QVQLVQSGAEVKKPGASVKVSCKASGYTFISHGMSWVRQAPGQG LEWMGWISADNGNTNYAQKFQERVTITRDMSTSTAYMELSSLRS EDTAVYYCATHGGDRSYWGQGTLVTVSS | 48. |
| A12. | QVQLVQSGAEVKKPGASVKVSCKASGYTFISHGMSWVRQAPGQG LEWMGWISADNGNTKYAQKFQDRVTLTTDTSTSTAYLELRSLRS DDTAVYYCATHGGDRSYWGQGTLVTVSS | 49. |
| G3. | QVQLVQSGAEVKKPGASVKVSCKVSGYTLTELSMHWVRQAPGKG LEWMGGFDPEDGETIYAQKFQGRVTMTRDTSISTAYMELSRLRS DDTAVYYCATHGGDRSYWGQGTLVTVSS | 50. |
| F05. | QVQLVQSGAEVKRPGASVKVSCKASGYTLTELSMHWVRQAPGKG LEWMGGFDPEDGETIYAQKFQGRVTMTEDTSTDTAYMELSSLRS EDTAVYYCATHGGDRSYWGQGTLVTVSS | 51. |
| H12. | QVQLVQSGAEVKKPGASVKVSCKASGYTFTDNYVHWVRQAPGQG LEWMGGIIPIFGTANYAQKFQGRVTITADESTSTAYMELSSLRS EDTAVYYCATHGGDRSYWGQGTLVTVSS | 52. |
| G12. | QVQLVQSGAEVKKPGSSVKVSCKASGGAFNAYPISWVRQAPGQG LEWMGGIIPVSGTPNYAQKFQGRVTITADKSTYTAYMELSSLRS EDTAVYYCATHGGDRSYWGQGTLVTVSS | 53. |
| C06. | QMQLVQSGAEVKKPGASVKVSCMASGYTFTGHYIHWVRQAPGQG LEWMGGIIPIFGTANYAQKFQGRVTITADESTSTAYTELSSLRS EDTAVYYCATHGGDRSYWGQGTLVTVSS | 54. |
| C11. | QVQLVQSGAAVKKPGASVKVSRKASGYTFTNDYIHWVRQAPGQG LEWMGGIIPIFGTANYAQKFQGRVTITADESTSTAYMELSSLRS EDTAVYYCATHGGDRSYWGQGTLVTVSS | 55. |
| F08. | QVQLVQSGAEVKKPGASVKVSCKASGYTFTSSYIHWVRQAPGQG LEWMGGIIPIFGTANYAQKFQGRVTITADKSTSTAYMELSSLRS EDTAMYYCATHGGDRSYWGQGTLVTVSS | 56. |
| E9. | QVQLVESGAEVRKPGESLQISCKASGYRFTNYWIGWVRQMPGKG LEWMGITYPADSTTVYSPSFQGQVTISADKSISTVFLQWSSLRS EDTAVYYCATHGGDRSYWGQGTLVTVSS | 57. |
| E11. | QVQLVESGGGVVQPGRSLRLSCAASGFTFSSYWMHWVRQAPGKG LVWVSRINNDGSSTSYADSVKGRFTISRDTAKNTLYLQMNSLRA EDTAVYYCATHGGDRSYWGQGTLVTVSS | 58. |

TABLE 3-continued

Amino acid sequences of exemplary PDGFRβ-binding VH domains selected from HCDR3 shuffled VH libraries.

| Clone name | VH Amino Acid Sequence | SEQ ID NO. |
|---|---|---|
| H11. | QVQLLESGAEVKNPGASVKVSCKASGYPFSAYYIQWVRQAPGQG LEWMGWLNPNSGDTHSAQKFQGRVTMTRDTSISTAYMELSGLTS DDTAVYYCATHGGDRSYWGQGTLVTVSS | 59. |
| C08. | EVQLLESEGGLVQPGGSLRLSCTASGFSFNAFWMHWVRQAPGKG LEWVSRISIDGTTTTYADSVQGRFTISRDNARNTLYLQMNSLRA EDAAVYYCATHGGDRSYWSQGTLVTVSS | 60. |
| | XB1511 framework shuffled and selected with human PDGFRβ and off rate selection | |
| XB2708 | QVQLVQSGGGVVQPGGSLRLSCAASGFTSRSYGMHWVRQAPGKG LEWVAFILFDGNNKYYADSVKGRFTISSDNSKNTLYLQMNSLRA EDTAVYYCATHGGDRSYWGQGTLVTVSS | 61. |
| D03. | QVQLVQSGGGLVQPGGSLRLSCVASGFTFGNDWMHWVRQAPGKG LVWVSRINADGTSTAYAESVKGRFTVSRDNAKNTLYLQMNGLRA EDTAVYYCATHGGDRSYWGQGTLVTVSS | 62. |
| A10. | QVQLVQSGGGLVQPGRSLRLSCAASGFTFDDYAMNWVRQAPGKG LEWVSLIYSDGSTYYADSVKGRFTISRDNSKKTLYLQMNNLRVE DTAVYYCATHGGDRSYWGQGTLVTVSS | 63. |
| C09. | QVQLVQSGGALVQPGGSLRLSCAASGFTLSNNAMSWVRQAPGKR LEWVSAIDGSGGTTYYAGSVKGRFTISSDNSKNTVFLQMNSLPA EDTAVYYCATHGGDRSYWGQGTLVTVSS | 64. |
| A06. | QVQLVQSGGGLVQPGGSLRLSCAASGFTFSGHWMHWVRQVPGKG LVWVSHISNDGSITRYADSVKGRFTVARDNAKNTMYLQMNSLRA EDTAVYYCATHGGDRSYWGQGTLVTVSS | 65. |
| C05. | QVQLVQSGGGLVKPGGSLRLSCAASGFIFSSNWMHWVRQVPGKG LEWVSRIKTDGSSTSYADSVKGRFTISRDNAKNTLYLQMNSLPA EDTAVYYCATHGGDRSYWGQGTLVTVSS | 66. |
| H01. | QVQLVQSGGGLVQPGGSLRLSCAASGFTLSSDWMHWVRQAPGKG LVWVSRISSDGSTTAYADSVRGRFTISRDNAKNTLYLQMNSLRA EDTAVYYCATHGGDRSYWGQGTLVTVSS | 67. |
| G04. | QVQLVQSGGGLVQPGGSLRLSCAASGFTLSSDWMHWVRQAPGKG LVWVSRISSDGSTTAYADSVRGRFTISRDNTKNTLYLQMNSLRA EDTAVYYCATHGGDRSYWGQGTLVTVSS | 68. |
| G07. | QVQLVQSGGGLVQPGGSLRLSCAASGFTFSSDWMHWVRQAPGEG LVWVSRISSDGSSTAYADSVKGRFTISRDNAKNTVSLQMNSLRA EDTAVYYCATHGGDRSYWGQGTLVTVSS | 69. |

C. Binding Specificity of Selected HCDR3 Shuffled VH Domains

Figure 4:
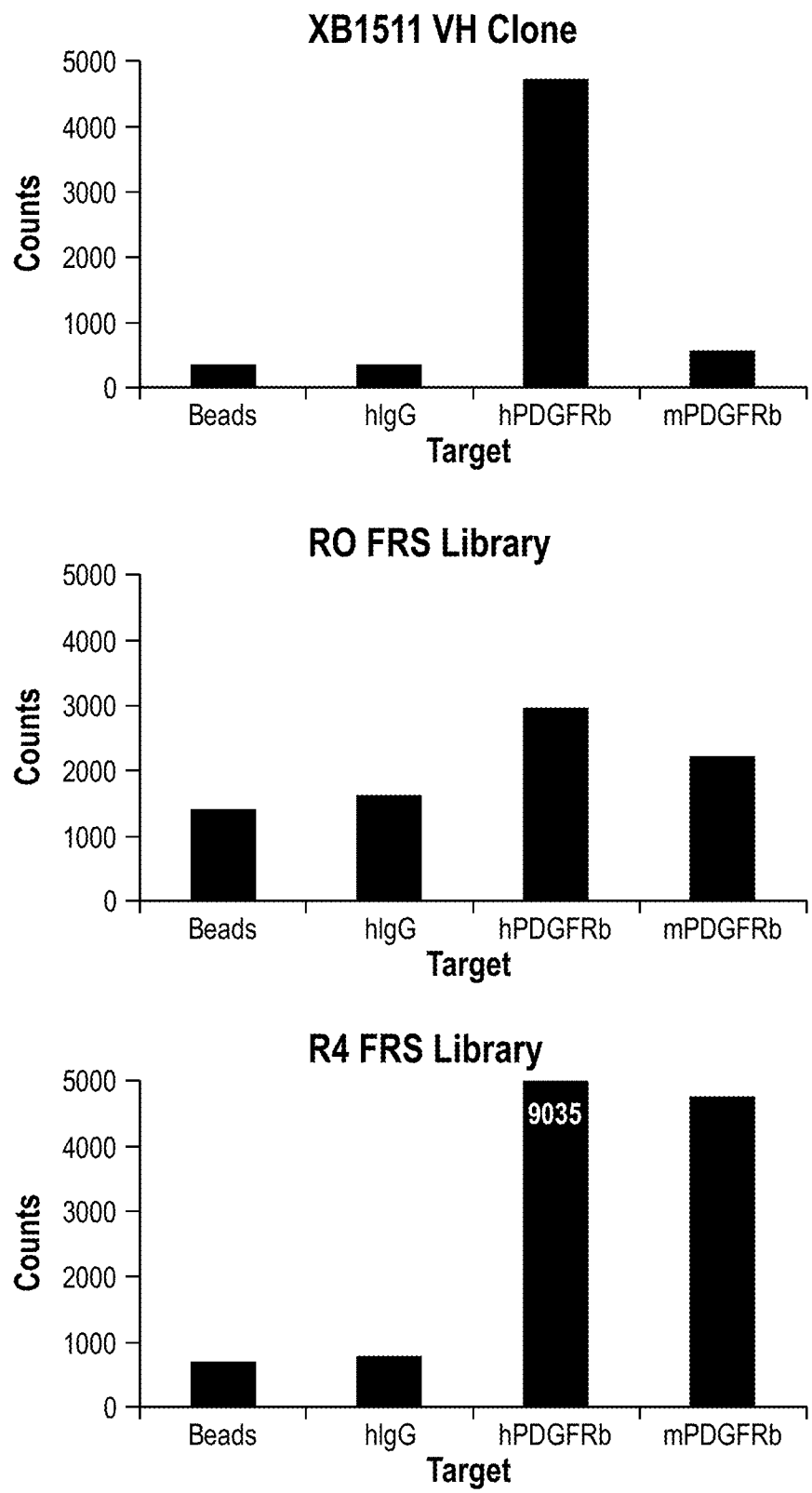
FIG. 4 depicts the results of in vitro binding assays measuring the binding to human or mouse PDGFRβ of the XB1511VH domain, an unselected XB1511 CDR3/framework shuffled DNA display library (R0), and an XB1511 CDR3/framework shuffled DNA display library pool after four rounds of selection (R4).

The R4 binding pool selected above was assessed for binding to both human and mouse PDGFβ using a $^{35}$S Met-labelled in vitro translated library. Specifically, binding of the pool to epoxy beads, 100 nM of human IgG, human PDGFβ and mouse PDGFRβ were assessed. As shown in FIG. 4, the parental XB1511 VH domain showed specific binding to human PDGFRβ, and undetectable binding to mouse PDGFRβ. The framework shuffled pre-selected library showed weak binding to human PDGFRβ. However, in contrast, the R4 framework shuffled library showed significant binding to both human and mouse PDGFRβ.

D. Binding Affinity of Selected HCDR3 Shuffled VH Domains

Figure 5:
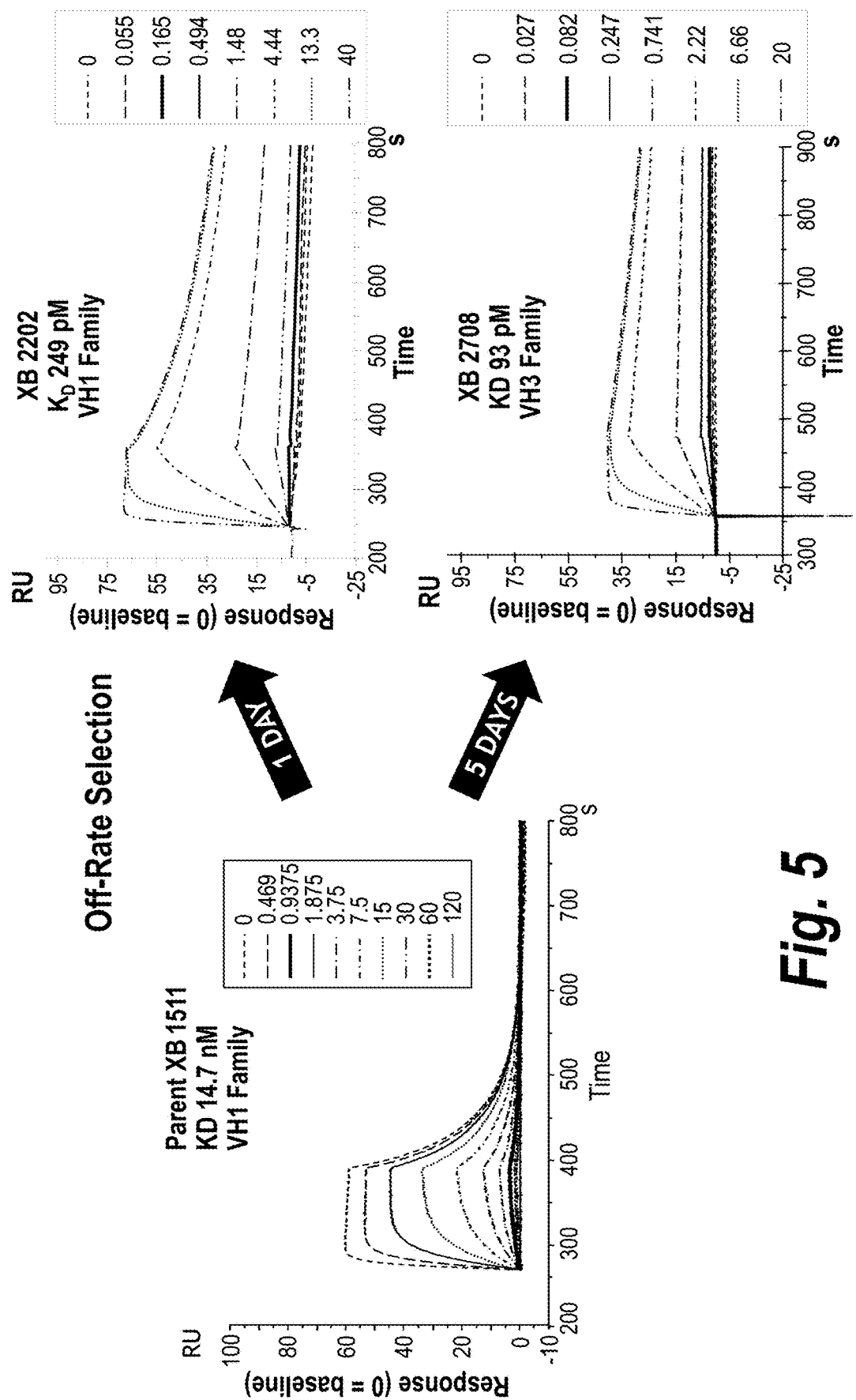
FIG. 5 depicts the results of surface Plasmon resonance binding studies measuring the binding kinetics of XB1511 and the framework shuffled derivatives XB2202 and XB2708 to human PDGFRβ.
Figure 6A:
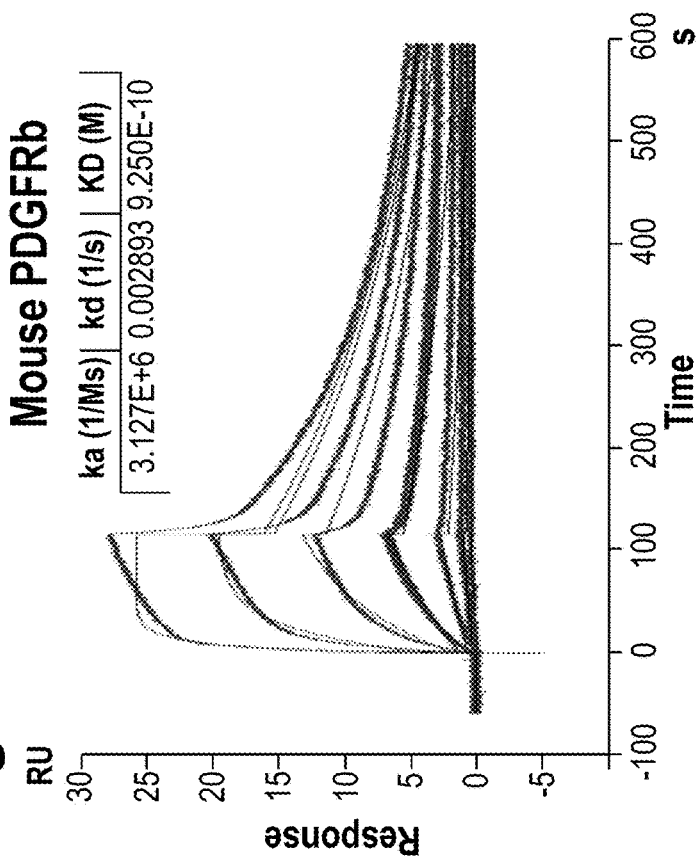
FIGS. 6A-6B depict the results of surface plasmon resonance binding assays measuring the binding kinetics of XB2202 to human (FIG. 6A) and mouse (FIG. 6B) PDGFRβ.
Figure 6B:
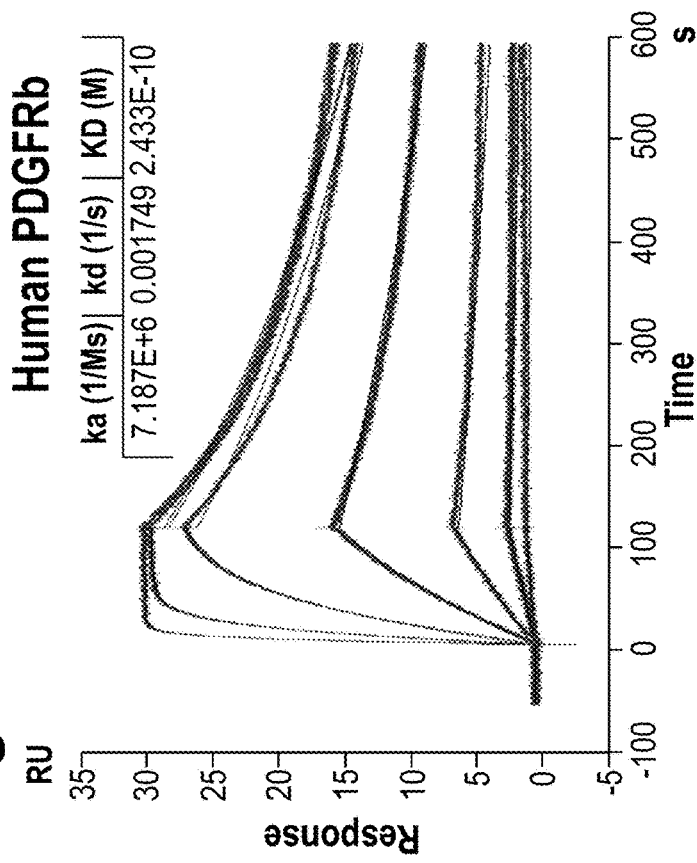
Figure 7A:
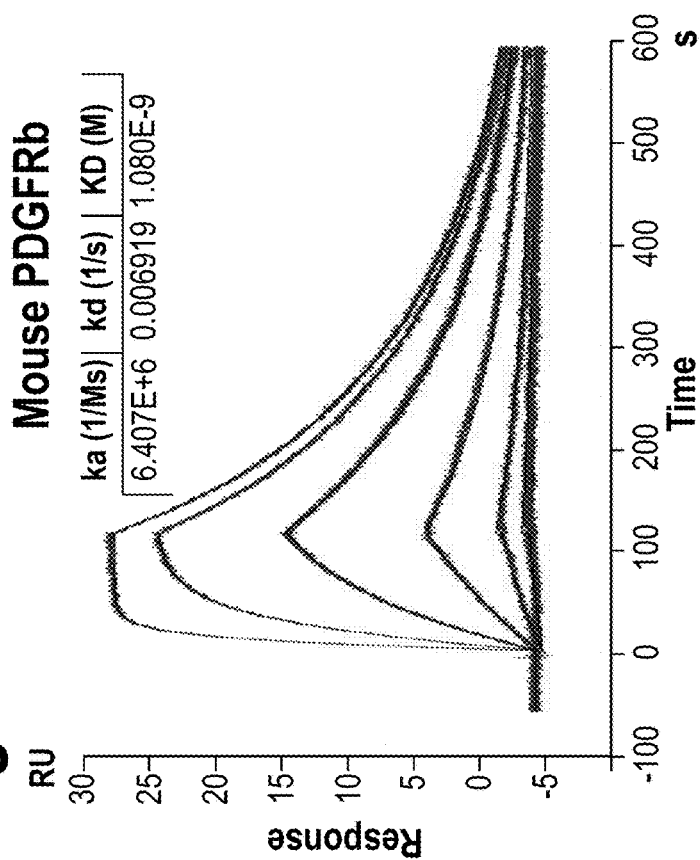
FIGS. 7A-7B depict the results of surface plasmon resonance binding assays measuring the binding kinetics of XB2708 to human (FIG. 7A) and mouse (FIG. 7B) PDGFRβ.
Figure 7B:
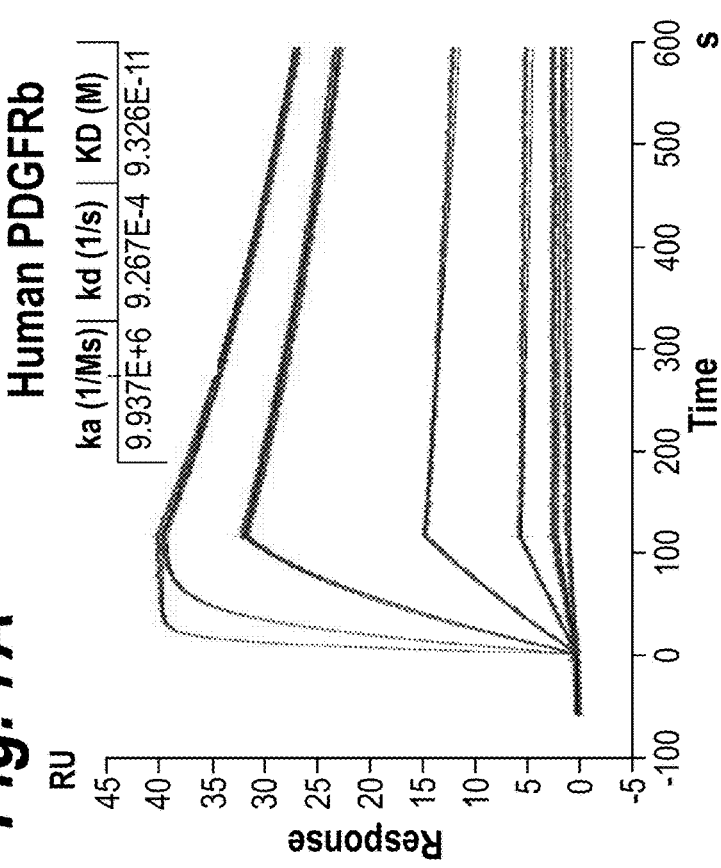

The R4 framework shuffled human and mouse PDGFβ enriched VH domain pool was cloned into E. coli expression vectors, produced and purified. The binding kinetics of the VH domains to human and mouse PDFGR was determined using surface Plasmon resonance on a Biacore T100. Briefly, human and mouse PDGFR-hIgG1-Fc chimeric fusion protein were separately immobilized using a Series CM5 sensorchip (CM5) coupled to anti-hIgG1 Fc monoclonal antibody. For each cycle, the PDGFR fusion protein was first captured, followed by the injection of VH for 115 seconds at a flow rate of 100 uL/min (association). Immediately following the association phase is a dissociation phase of 600 seconds. The surface was regenerated at each cycle with a single injection 3M MgCl2 (10 uL/min, 60 seconds). Multiple concentrations of VH were injected (0.55 nM-40 nM) and the resulting sensorgram were analyzed with T100 Evaluation software. The binding kinetics was determined using 1:1 binding curve fitting. The binding kinetics of VH domain clones XB2202 and XB2708 to human and mouse PDGFR are shown in FIGS. 4, 5 and 6. These results show that XB2202 and XB2708 have a 50-150 fold affinity improvement compared to parental XB1511. Specifically, XB2202 and XB2708 have Kds of 249 pM and 93 pM, respectively and off rates (Koff) of $1.86 \times 10'$ and $9.267 \times 10^{-4}$, respectively. Both XB2202 and XB2708 bound to human and mouse PDGFRβ. It is of particular note that, although they shared the same HCDR3, XB2202 was derived from a VH1 family germline sequence and XB2708 was derived from VH3 family germline sequence.

Example 3. Identification of Stable VL/VH Pairs

A. Construction of VL DNA Libraries

Figure 8:
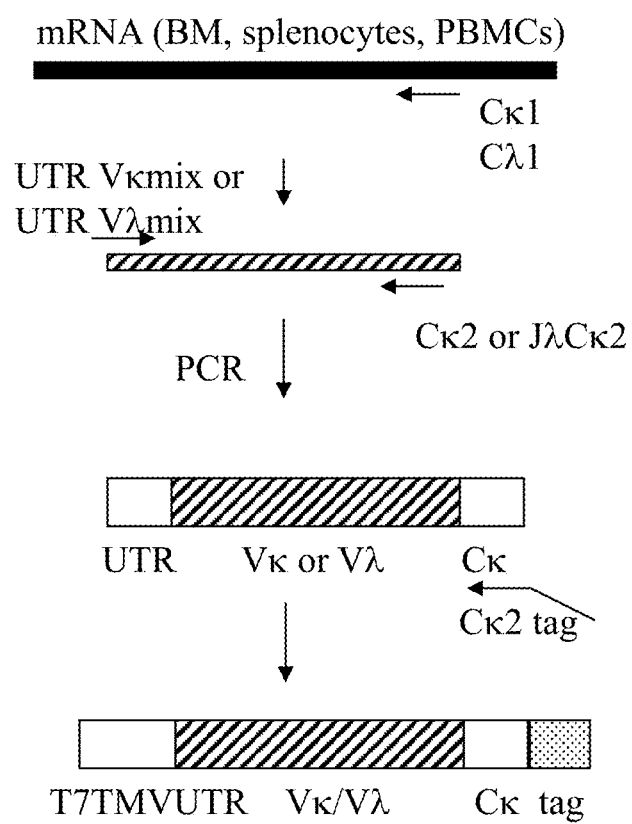
FIG. 8 is a schematic representation of the construction of exemplary VL nucleic acid display libraries for use in the disclosed methods.

Human VL libraries (Vkappa and Vlamda) were constructed from B cells of young healthy donors (Allcells) by RT-PCR. To ensure the diversity of the library, 300 million mononuclear cells from bone marrow of each donor and total of 10 donors and 100 million of peripheral blood mononuclear cells from each donor and total of 10 donors were obtained for naïve VH and VL library construction. A schematic of the library generation method is set forth in FIG. 8.

Oligonucleotide primers for cDNA synthesis and subsequent PCR amplification of the Vkappa and Vlamda sequences were design as set forth in Table 4. Specifically, multiple sense primers were designed from the Vκ and Vλ FR1 regions of each family with an upstream UTR sequence. The anti-sense primers for κ and λ gene amplification were designed from the constant regions nested to Cκ1 (Cκ2) or Jλ with the same Cκ2 downstream (JλCκ2). The Vκ and Vλ libraries carry the same C-terminal sequence for PCR amplification during the selection cycles.

mRNA was prepared with individual donors using a FastTrack mRNA preparation kit (Invitrogen) following the protocol provided by the kit. First strand cDNA was synthesized from the isolated mRNA using primers specific for the light chain kappa and lambda constant regions (Cκ1 and Cλ1).

PCR amplification of the Vkappa and Vlamda sequences was performed with Cκ2 and Vκ family specific or JλCκ2 mix and Vλ family specific oligos using cDNA synthesized from mRNA prepared from the various source of B cells as template. The PCR was performed with individual families and individual donors for 18-20 cycles. After gel purification, Vκ and Vλ libraries from different sources were pooled to generate Vκ and Vλ libraries.

TABLE 4

Oligonucleotides for constructing human Vλ and Vκ DNA display libraries

| | Sequence | SEQ ID NO. |
|---|---|---|
| Oligo | | |
| Ck1 | CAACTGCTCATCAGATGGCGG | 70. |
| cl1 | CAGTGTGGCCTTGTTGGCTTG | 71. |
| Ck2 | AGATGGTGCAGCCACAGTTCG | 72. |
| Jl1-3Ck2 | AGATGGTGCAGCCACAGTTCGTAGACGGTSASCTTGGTCCC | 73. |
| J17Ck2 | AGATGGTGCAGCCACAGTTCGGAGACGGTCAGCTGGGTGCC | 74. |
| T7TMVUTR | TAATACGACTCACTATAGGGACAATTACTATTTACAATTACA | 75. |
| Vλ oligos | | |
| UTRVk1a | CAATTACTATTTACAATTACAATGRACATCCAGATGACCCAG | 76. |
| UTRVk1b | CAATTACTATTTACAATTACAATGGMCATCCAGTTGACCCAG | 77. |
| UTRVk1c | CAATTACTATTTACAATTACAATGGCCATCCRGATGACCCAG | 78. |
| UTRVk1d | CAATTACTATTTACAATTACAATGGTCATCTGGATGACCCAG | 79. |
| UTRVk2a | CAATTACTATTTACAATTACAATGGATATTGTGATGACCCAG | 80. |
| UTRVk2b | CAATTACTATTTACAATTACAATGGATRTTGTGATGACTCAG | 81. |
| UTRVk3a | CAATTACTATTTACAATTACAATGGAAATTGTGTTGACRCAG | 82. |
| UTRVk3b | CAATTACTATTTACAATTACAATGGAAATAGTGATGACGCAG | 83. |
| UTRVk3c | CAATTACTATTTACAATTACAATGGAAATTGTAATGACACAG | 84. |
| UTRVk4a | CAATTACTATTTACAATTACAATGGACATCGTGATGACCCAG | 85. |
| UTRVk5a | CAATTACTATTTACAATTACAATGGAAACGACACTCACGCAG | 86. |
| UTRVk6a | CAATTACTATTTACAATTACAATGGAAATTGTGCTGACTCAG | 87. |

TABLE 4-continued

Oligonucleotides for constructing human Vλ and Vκ DNA display libraries

| | Sequence | SEQ ID NO. |
|---|---|---|
| UTRVk6b | CAATTACTATTTACAATTACAATGGATGTTGTGATGACACAG | 88. |
| UTRVL1a | CAATTACTATTTACAATTACAATGCAGTCTGTGCTGACKCAG | 89. |
| UTRVL1b | CAATTACTATTTACAATTACAATGCAGTCTGTGYTGACGCAG | 90. |
| UTRVL2 | CAATTACTATTTACAATTACAATGCAGTCTGCCCTGACTCAG | 91. |
| UTRVL3a | CAATTACTATTTACAATTACAATGTCCTATGWGCTGACTCAG | 92. |
| UTRVL3b | CAATTACTATTTACAATTACAATGTCCTATGAGCTGACACAG | 93. |
| UTRVL3c | CAATTACTATTTACAATTACAATGTCTTCTGAGCTGACTCAG | 94. |
| UTRVL3d | CAATTACTATTTACAATTACAATGTCCTATGAGCTGATGCAG | 95. |
| UTRVL4 | CAATTACTATTTACAATTACAATGCAGCYTGTGCTGACTCAA | 96. |
| UTRVL5 | CAATTACTATTTACAATTACAATGCAGSCTGTGCTGACTCAG | 97. |
| UTRVL6 | CAATTACTATTTACAATTACAATGAATTTTATGCTGACTCAG | 98. |
| UTRVL7 | CAATTACTATTTACAATTACAATGCAGRCTGTGGTGACTCAG | 99. |
| UTRVL8 | CAATTACTATTTACAATTACAATGCAGACTGTGGTGACCCAG | 100. |
| UTRVL4/9 | CAATTACTATTTACAATTACAATGCWGCCTGTGCTGACTCAG | 101. |
| UTRVL10 | CAATTACTATTTACAATTACAATGCAGGCAGGGCTGACTCAG | 102. |

R = A/G, Y = C/T, K = G/T, M = A/C, S = G/C, W = A/T

B. Generation of VL Fusion Libraries by dsDNA Display

Vk and VL DNA libraries generated using the methods set forth in this Example were transcribed into mRNA libraries using the T7 Megascript kit (Invitrogen, Cat #AM1334). The mRNA was purified with RNeasy MinElute Cleanup Kit (Qiagen, Cat #74204) following protocol provided by the kit. A total of 600 pmol of RNA (300 pmol of Vk and Vl libraries) was ligated and assembled with dsDNA display linkers and components as described in WO2010/011944. The assembled VL library was subjected to in vitro translation system to create a fusion library in which each VL domain (phenotype) is stably fused to its coding sequence (genotype). $^{35}$S Met was incorporated in the translation process to radiolabel the fusions. The library was then purified with oligo dT cellulose, converted into a dsDNA display library using the standard molecular biology techniques of reverse transcription, RNaseH digestion, $2^{nd}$ strand DNA synthesis, followed by flag tag purification. A schematic of this process is set forth in FIG. 3.

C. Identification of VL Pairs for XB1511, and XB2202 VH Domains

Figure 9:
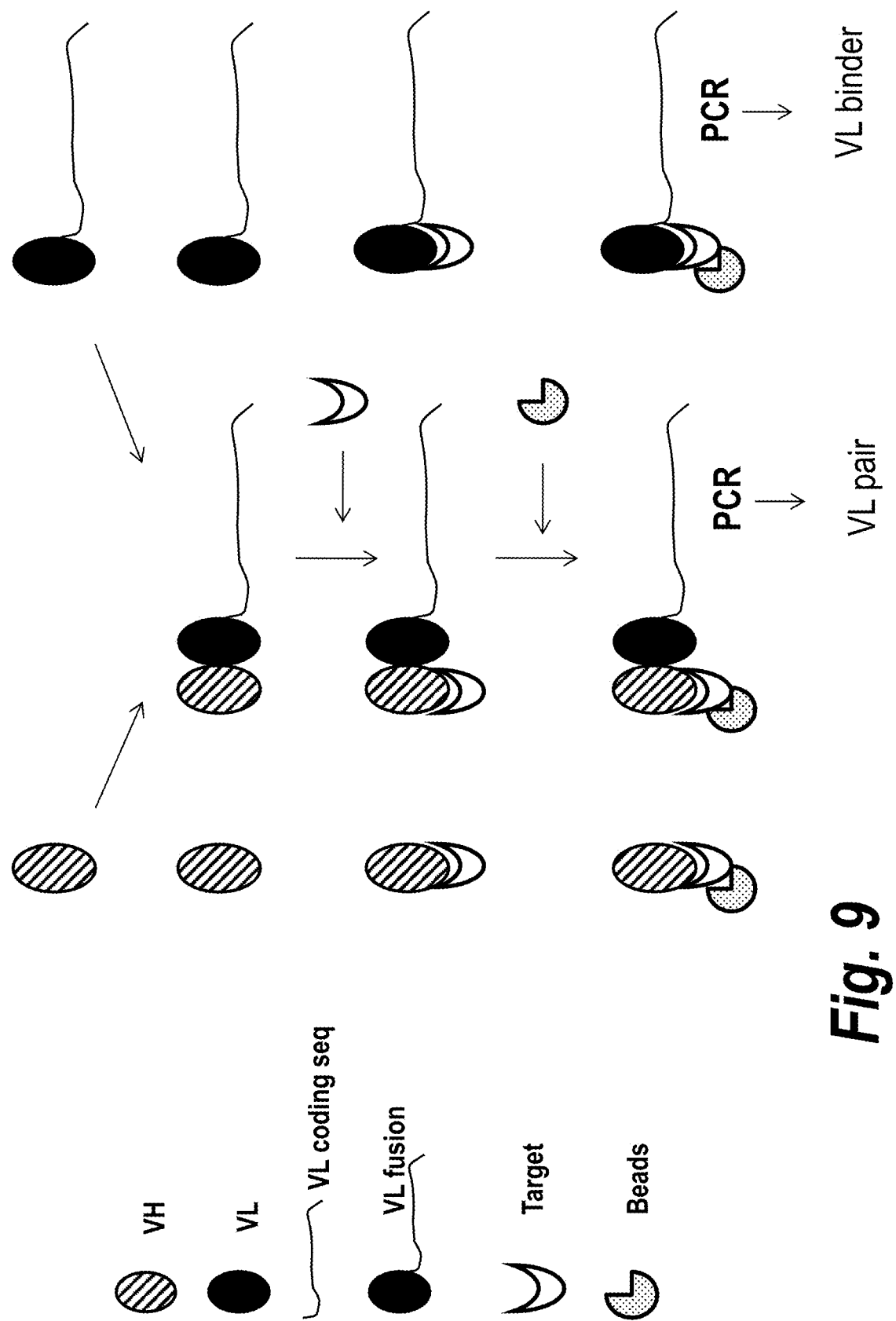
FIG. 9 is a schematic representation of exemplary methods for identification of stable VH/VL pairs.

As a proof of concept, PDGFRβ VH binding domain XB1511 was translated as free protein (with incorporation of $^{35}$S Met in the translation reaction) and affinity purified through a c-terminal flag tag. The XB1511 and a purified VL fusion library (prepared as above) were then mixed at an equal molar ratio and incubated at 25 C overnight to allow for in vitro association of VH and VL fusion domains through their hydrophobic patch. The mixture was then contacted with PDGFRβ target pre-immobilized on Epoxy450 beads or in solution and captured by protein A beads. Complexes that bound to the immobilized PDGFRβ target were washed and eluted with 0.1N KOH. PCR was performed with VL specific primer sets to recover the VLs that bound to the PDGFRβ target, both as VH-VL pairs and as unpaired VL domains. The VL pairing was performed for 3 rounds, with low stringency (100 nM PDGFRβ) for the first 2 rounds and higher stringency (10 nM PDGFRβ) for the third round. PDGFRβ VH binding domain XB2202 was also paired with VL library similarly for 2 rounds. For each round of XB2202 VL pairing and selection, the stringency was increased by kinetic controlled on and off rate strategy to identify VLs that can pair with VH stably and enhance the VH binding. A schematic of this process is set forth in FIG. 9.

VL pools identified above were then cloned into Blunt Zero TOPO vector (Invitrogen) and VL-encoding DNA sequences were amplified from the resultant bacterial colonies by PCR using M13 forward and reverse primers. The individual amplified VL-encoding DNA sequences were then sequenced. The sequence data obtained from VL pools showed that a diverse repertoire of VLs was enriched through the process. Multiple families and frameworks were present in the pool. Several VLs were present as replicates or families. Distinct VL families could be identified and several VLs were present more than once. Exemplary VL sequences identified using the methods of the invention that pair with the PDGFRβ-binding VH domains XB1511 and XB2202 are set forth in Table 4 herein.

TABLE 4

Light chain variable domain (VL) amino acid sequences of exemplary anti-PDGFRβ antibodies.

| Clone name | VL Amino Acid Sequence | SEQ ID NO. |
|---|---|---|
| | PR2 VL sequences from XB1511 pairing | |
| B10. | QSVLTQSPDLQSVTPREKLTITCRASQTIGSTLHWYQQKPGQSPR LVIKYAYQSVSGVPSRFSGSGSGTEFTLTINGLEAEDAATYYCHQ SSSLPWTFGQGTKLTVL | 103 |
| H10. | QSVLTQSPDFQSVSPKDKVTITCRASQSIGSSLHWYQQKPGQSPK LLIKYSSQSFSGVPSRFSGSASGTEFTLTITGLEAEDAATYYCHQ SSSLPHTFGQGTKVTVL | 104 |
| F10. | QSVLTQSPEFQSVTPKEKVTITCRASQSIGSGLHWYQQKPHQSPK LLIRYASQSMSGVPSRFSGSGSGTDFTLTISRLEVEDAAMYYCHQ SSSLPWTFGQGTKVTVL | 105 |
| B12. | QSVLTQSPDFQSVTPKQNVTFTCRASQSIGIKLHWYQQKPDQSPK VLIKYASQPFSGVPSRFSGRGSGTDFTLTINSLEAEDAATYYCHQ TSSLPLTFGGGTKVTVL | 106 |
| B11. | QSVLTQSPGTLSLSPGERATLSCRASQSVSSNYLAWYQQKPGQAP RLLIYGASSRASGIPVRVSGSGSGTDFTLTISRLEPEDFAVYYCQ QYGSSPWTFGQGTKLTVL | 107 |
| E7. | QSVLTQSPGTLSLSPGERATLSCRASQSVSSSYLAWYQQKPGQAP RLLIYGASSRATGIPDRFSGSGSGTDFTLTISRLEPEDFAVYYCQ QYGSSPQTFGQGTKLTVL | 108 |
| E8. | QSVLTQSPGTLSLSPGERATLSCRASQSVSSSYLAWYQQKPGQAP RLLIYGASSRATGIPDRFSGSGSGTDFTLTISRLEPEDFAVYYCQ QYGSSPPYTFGQGTKLTVL | 109 |
| H8. | QSVLTQSPGTLSLSPGERATLSCRASQSVSSNYLAWYLQKPGQAP RLLISGASSRATGIPDRFSGSGSGTDFTLTISRLEPEDFAVYYCQ QYAGSPFTFGPGTKLTVL | 110 |
| H12. | QSVLTQSPGTLSLSPGERATLSCRASQSVRSSYVAWYQQKPGQAP RLLISGASRRATGIPDRFTGSGSGTDFTLTISRLEPEDFAVYHCQ QFGSSPWTFGQGTKLTVL | 111 |
| F8. | QSVLTQPPSASGTPGQRVTISCSGGRSNIGGNAVNWYQQKPGQAP RLLIHVASRRVTGIPDRFSGSGSGTDFTLTISRLEPEDFAIYYCQ QYGSSPLTFGGGTKLTVL | 112 |
| D11. | QSVLTQSPGTLSLSPGERATLSCRASQNITSNFFAWYQQKPGQAP RLLIYGASSRATGIPDRISGSGSGTDFTLTISRLEPEDFALYYCQ QYGASPRTFGQGTQLTVL | 113 |
| G8. | QSVLTQSPGTLSLSPGDRATLSCRASQSLSGTYLAWYQQKPGQAP RLLIYDASNRAAGIPKRFSGSGSRTDFTLTISRVDPADSAVYYCQ QYGSALLTFGGGTKVTVL | 114 |
| H9. | QSVLTQSPGTLSLSPGESATLSCRASEDIYNNYLAWYQHKRGQPP RLLIFRASTRATGIPTRFSGSGSGRDFVLTINRLEPEDFAVYYCQ QYGNSWTFGQGTKLTVL | 115 |
| H11. | QSVLTQSPDFQSVTPKEKVTITCRASQSIGSSLHWYQQKPDQSPK LLITFASQSFSGVPSRFSGSGSGTDFTLTINSLEAEDAATYYCHQ SRNLPFTFGPGTKLTVL | 116 |
| G12. | QSVLTQSPDFQSVTPKEEVTITCRASESIGTALHWYQQKPDQSPK LLIKYSSQSISGVPSRFVGRGSETEFTLTINSLEAENAATYYCHQ SRSFPLTFGQGTQLTVL | 117 |
| E11. | QSVLTQSPGTLSLSPGERATLSCRTSQILHSQYLAWYQQKRGQAP RLLIFRASTRATGIPERFSGSGSGRDFVLTISRLEPEDSAVYYCQ QYETSWTFGQGTKVTVL | 118 |
| F12. | QSVLTQDPVVSVALGQTVRITCQGDTLRTCYASWYQQRPRQAPIL VIYGENNRPSGIPARFSGSSSGSTASLTITGAQAEDEGDYYCHCR DGLNHLVFGGGTKVTVL | 119 |
| C8. | QSVLTQPPSVSAAPGQKVTISCSGSTSNIGKNFVSWYQHLPGTAP KLLIYDNYQRFSGIPDRFSGFKSGTSATLSITGLQTADEADYYCG TWDSSLSVVIFGGGTKLTVL | 120 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| A8. | QAGLTQSPDFQSVTPKERVTITCRASRYIGSNLHWYQQKPDQPPK LLIKLASQSFSGVPPRFSGGGSGTDFTLTINGLEAEDAATYYCHQ TGSFPYTFGQGTKLTVL | 121 |
| B8. | QAVLTQEPSLTVSPGGTVTLTCGSSTGAVTSGHSPFWFQQRPGQA PRTLIYDTSNKQSWTPARFSGSLLGGKAALTLSGAQPEDEAEYYC LLSYSGPRVVFGGGTKVTVL | 122 |
| F7. | QAVVTQSPDSLAVSLGERATISCKSSXSLLYRSNNKNYLAWYQQK PGQPPRLLISWASTRESGVPDRFSGSGSGTDFTLTVSRLRAEDAA VYYCQQSYRTPFSFGPGTKVTVL | 123 |
| B7. | SYVLTQPLSVSVALGQTARISCGGANIANKNVHWYQLQPGQAPVL VIYRDSNRPSGIPERFSGSNSGNTATLTITRAQARDEADYYCQVW DSSSVIIGGGTKVTVL | 124 |
| G9. | SYVLTQDPAVSVALGQTVRITCQGDSLRTYYASWYRQKPGQAPVL VFYGKDNRPSGIPDRFSGSSSGNTASLTITGAQAEDEADYYCKSR DSSAMRWVFGGGTKLTVL | 125 |
| A9. | NFMLTQEPSLTVSPGGTVTLTCGSSTGAVTSGHYPYWFQQKPGQV PRTFIYDTHNRHSWTPVRFSGSLFGGKAALTLSGAQPEDEAEYYC LLYFNPTRVFGGGTKLTV | 126 |
| A11. | NFMLTQPPSASASLGASVTLTCTLSSGYSNYKVDWYQQRPGKGPR FVMRVGTGGIVGSKGDGIPDRFSVLGSGLNRYLTIKNIQEEDESD YHCGADHGRVFGGGTKLTVL | 127 |
| E12. | QPVLTQPPSVSVAPGKTARITCGGNNIGSKSVHWYHLRPGQAPVL VIYFDSDRPSGIPERFSGSNSGNTATLTISRVEAGDEADYYCQVW HSGVIFGGGTKLTVL | 128 |
| H7. | QPVLTQSLDFQSVTPKEKVTITCRASQNIGNSLHWYQQKPNQSPK VLIKYASQSFSGVPSRFSGSGFGTDFTLTINSLEPEDAATYYCHQ SRSSHTFGQGTKLTVL | 129 |
| A10. | EIVLTQSPGNLSLSPGERATLSCTRCTGNIASHFVQWYQQRPGSS PTTVIFGNNQRPSGVSDRFSGSIDSSSNSASLTISRLKTEDEADY YCQSFDVYSHEVVFGGGTKLTVL | 130 |
| C11. | QTVVTQTPVSLSVTPGQPASISCKSSQSLLNSDDGKTYLYWYLQR PGQPPHLLIYEVSKRFSGVPDRFSGSGSGTDFTLRISRVEAEDVG VFYCMQSTHFPFTFGPGTKVTVL | 131 |
| D10. | NIQMTQSPVSLSASLGDTVSITCQASHDISNYLNWYQQKPGKAPK LLIYDASHLEAGVPSRFRGSGSGTDFTLTINRLEPEDFAVYYCQQ YDSPPWTFGQGTKLTVL | 132 |
| D12. | DVVLTQSPGTMSLSPGERATLSCRASQSVSRTYLAWHQQKPGQAP RLLIYGASSRAAGIPDRFSGSGSGTDFTLSISRLEPEDFAVYYCQ QHDTSQWTFGQGTKLTVL | 133 |
| C7. | DIVMTQTPLSLSVTPGQPASISCKSSQSLLHSDGKTHLFWYLQRP GQSPQLLIYEVSGRFSGVSERFSGSGSGTDFTLKISRVEAEDVGV YYCMQGLHIPHTFGQGTKVEIK | 134 |
| D7. | DIVMTQSPLSLPVTLGQPASISCRSSHSLVHSDGNIYLNWYHQRP GQSPRRLIYSVSKRDSGVPDRFSGSGSRTDFTLKISRVEAEDVGV YFCMQSTHQWTFGQGTKVEIK | 135 |
| C9. | VIWMTQSPSTVSASVGDRVTITCRASQSISSWLAWYQQKPGKAPN LLIYEASRLESGIPSRFSGSGSGTEFTLTXSSLQPDDFATYYCQQ YDSYSRTFGQGTKVAIK | 136 |
| C12. | DVVMTQSPSSLSASVGDRVTITCRTSQGIRNYLSWYQQKPAKAPK LLIHGASGLQSGVPSRFSGSGSGTNFTLTISSLQPEDFATYYCQQ SFSMRTFGQGTKVEIK | 137 |
| D8. | EIVMTQSPGTLTLSPGEGATLSCRASQSVTSNYLAWYQQRPGASS LQSGQAPRLLIYDASNRATGIPDRFSGSGFGTDFTLTISRLEPED FAVYYCQQYVNSRTFGQGTKVEIK | 138 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| D9. | EIVMTQSPVTLSVSPGERATLSCRASQSVSSKLAWYQQKPGQAPR LLIYGASTRATGIPARFSGSGSGTEFTLTISSLQSEDFAIYYCQQ YNDFFTFGPGTKVDIK | 139 |
| G7. | EIVLTQTPLSSPVTLGQPASISCRSSESPVHSDGNIYLSWLHQRP GQPPRLLLYKISNRMSGVPDRFSGSGAGTDFTLKISRVEAEDVGV YYCMQATQFPSFGQGTKLEIK | 140 |
| G11. | EIVLTQSPGTLSLSPGEGATLSCRASQSVSSRNLAWYQQKPGQAP RLLIYGGSIRASGTSTRFSGSGSGTDFTLTINRLEPEDFAVYYCQ QYGDSVFTFGPGTKVDIK | 141 |
| F9. | NIQMTQSPSSLSASVGDRVNITCRASDNIGNYLNWYQHKPGKAPT VLIYAASTLHYGVPSRFSGRGSGTDFTVTISSLQPEDSATYYCQQ SYSTPRTFGQGTRVELK | 142 |
| E9. | AIQMTQSPSSLSASVGDRVTITCRASESISNYLNWYQQKPGKAPK LLLSAASRLQSGVPSRFSGSGSGTDFTLTITSLQPEDLATYYCQE SYSTLLYTFGQGTKLEIK | 143 |
| | VL sequences from XB2202 VLpairing | |
| B1. | SYELTQPPSVSVAPGKTASITCGGNNIGYDSVHWYQQKPGQAPVL VVFDDSDRPSGIPERFSGSNSGNTATLTISRVEAGDEADYYCQVW ESGSEHYVFGTGTQLTVL | 144 |
| E6. | LPVLTQPPSVSVAPGQTARISCGGNNIGATTVHWYQHRPGQAPVS VIFYDNDRPSGIPERFSGSNSGNTATLTISRVEAGDEADYYCQVW ESTSDHPTFGGGTQLTVL | 145 |
| F3. | QSVLTQPPSVSVAPGKTARITCGGNNIGSKSVHWYQQKPGQAPVL VIYYDSDRPSGIPERFSGSNSGNTATLTISRVEAGDEADYYCQVW DSSSDHWVFGGGTKLTVL | 146 |
| H4. | SYELTQPSVSVPPGQTARITCGGNNIVSKGVHWYQQRPGQAPVL VVYDDSDRPSGIPERFAGFNSGNTATLTISRVEAGDEADYYCQVW DSSSGHRGVFGGGTKVTVL | 147 |
| H5. | SYELTQPPSVSMAPGKTARITCGGNNLGSKIVHWYQQKPGQAPVV VIYSDRDRPSGVPERFSGSNSGNSATLTISGVEAGDEADYYCQVW DSATDHVVFGGGTKLTVL | 148 |
| B5. | SYELTQPPSVSVAPGQTATITCAGNNIGGKSVQWYQQKPGQAPVV VVYDDYGRPSGIPERVSGSNSGNTATLTLTRVEAGDEADYYCQVW DSDRHHVVFGGGTKLTVL | 149 |
| G6. | QLVLTQPPSVSVSPGQTASITCSGDNLGHTNACWYQQNPGQSPVL VIYQDTKRPSGIPERFSGSNSGNPATLTIXRVXAGDEANYYCQVW DINDDYAVFGTGTXLTVL | 150 |
| C1. | QSVLTQSPGTLSLSPGERATLSCTASQSVSSTYLTWYQQKPGQAP RLLIYGASSRATGIPDRFSGSGSGTDFTLTISRLEPEDFAVYYCQ QYVSSPPMYTFGQL | 151 |
| F1. | DIQMTQSPSTLSASVGDRVTISCRASQNIDYDLAWYQXKPGKAPX LLIYGASNLEGGVPSXFSGXGSGTEFTLTISSLQPDXSATYYCQQ YVTYPLTFGQGTRLEIK | 152 |
| A3. | AIQMTQSPSSLSASVGDRVTMTCQASQVIDKYVNWYRQRPGKAPE LLIYGASTLESGVPSRFSGSGSGTQFTFSITSVQPEDFATYICQQ YDSVPLTFGPGTILDVKRTVA | 153 |
| B4. | DIQLTQSPSSLSASIGDRVTITCQASQDIFHYLNWFQQKPGKAPK LLIYEASNLETGVPSRFSGSGSVTDFTFTISSLQPEDIATYYCQQ YEDLPSFGGGTKVDIKRTVA | 154 |
| B6. | EIVLTQSPGTLSLSPGERATLSCRASQSFGSNYLAWYQHKPGQAP RLLIFAASNRATGIPDRFTGSASGTDFTLTINRVEPEDLAVYYCQ QYGSFPYSFGQGTKLEIK | 155 |
| F2. | NIQMTQSPSSLSASVGDRVTITCQASQFIHIYLNWYQQKLGKAPK LLIYGASNLERGVPSRFSGRGSETDFTFTIDSLQPEDIATYFCQQ YQNPPFTFGGGTKVE INGTVA | 156 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| D3. | AIRMTQSPSSLSASIGDRISVTCRASQDVGIYVAWFQQKPGKPPR SLIYAASYLQTAVPPKFRGSGSGTDFTLTISDLQPDDFATYYCQQ YKTFPHTFGQGTKLDFKRTVA | 157 |
| G2. | VIWMTQSPSTLSASVGDRVTITCRASQDINTWLAWYQQKPGKAPK LLMFKVSTLESGDFSRFSGSGSGTEFTLTVSSLQPDDSAIYYCQQ YHSYPYTFGQGTRLEIK | 158 |
| A4. | DVVMTQSPSSLSASVGDRVTITCQASQDISNWLNWYQQKPGKAPK LLIYEASNLETGVPSRFSGSGSGTDFTFTISSLQPEDIATYYCQQ YNNVLRTFGQGTKVEIK | 159 |
| G4. | EIVMTXSPATLSVSPGERVTLSCRVSQNVFSDLAWYQRKTGQSPR LLIHGASTRATGIPTRFSGSGSGTEFTLTISSLXSDDFAVYYCQQ YNKWPTFGQGTKVEIK | 160 |
| D5. | AIQLTQSPSSLSASVGDRVNITCRASDNIGNYLNWYQHKPGKAPT VLIYAASTLHYGVPSRFSGRGSGTDFTVTISSLRSDDFAVYYCQQ YYNWPPWTFGQGTTVDIKRTVA | 161 |
| A1. | EIVLTQSPATLSLSPGERATLSCRASQSVSSFLAWYQQKPGQAPR LLIFEASTRATGISARFSGSGSGTDFTLTISTLEPEDFAVYYCQQ RSNGVTFGQGTRLEIK | 162 |
| H2. | DIQMTQSPSTLSASVGDTVTITCRATESISIWLAWYQQEPGKAPN LLVSQASSLKTGVPSRFSASGSGTEFTLTISSLHPDDFATYVCQH YHTYPFTFGPGTKVDMKRTVA | 163 |
| E2. | EIVLTQSPDSXAVSLGERATINCKSSQSVLYSSNNKNYLAWYQQK PGQPPRLLIYWASTRESGVPDRFSGSGSGTDFTLTISRLQAEDVA VYYCQQYYLTPTFTVTFGQGTKLEIK | 164 |
| F4. | DIQLTQSPSSVSASVGDRVTITCRASQDISSWLAWYQQKPGKAPK FLIYRATNLQSGVPSRFSGSGSGTDFTLTISSLQPGDFATYYCQQ TNTFPLTFGGGTKVEVKRTVA | 165 |
| C5. | DIVMTQSPDSLAVSLGERATINCKSSQSVLYSSNNRNYLAWYQKK PGQPPKLLFYWASTRESGVSDRFSGSGSGTDFTLTISSLQAEDVA VYYCQQYHTTPYTFGQGTKLEIK | 166 |
| E5. | VIWMTQSPSSLSASVGDRVSITCRASQTFTSHLNWYQQKPGQPPK LLIFAASNLQSGVPSRFSGSGSGTDFTLTINGLQATDFATYYCQQ SFSSPWTFGQGTTVDVKGTVA | 167 |
| F6. | DIQMTQSPSSLSASVGDRVTITCRASQSVNVYLNWYQQKPGKAPK LLIYSASTLQSGVPSRFTGSGSRTDFTLTINGLQPEDFATYYCQQ SFTTLVTFGPGTRVDVTRTVA | 168 |
| G5. | DIQMTQSPSSLSASVGDRVTITCRASQDISSSLAWYQQKPGKAPK PLIYDASTLQTGVPSRFSGRASGTDFTLTIDSLQPEDFATYCCQQ FNSYPLSFGGGTKVELKRTVA | 169 |
| A5. | SYELTQPPSASASLGASVTLTCTVSSGYRSYEVDWFQQRPGKGPR FVMRVGTGGIVGSRGDGIPDRFSVWGSGLNRYLTIEDIQEEDESD YYCGADHGSGSNLVYFGTGTKVTVL | 170 |
| D6. | QLVLTQPPSASASLGASVTLTCTLSSDYSSYNVDWYQQRPGMGPR FLMRVGTGGIVGSRGDGIPDRFSVKGSGLNRYLTIKNIQEEDESD YYCGADHGSGSDFVYVFGIGTKLTVL | 171 |
| E4. | QSVLTQPPSASGTPGQRVTISCSGSSTNIGSNAVNWYQQLPRTAP KLLIYTNNQRPSGVPDRFSGSKSGTSASLAISGLQSEDEANYYCA AWDDSLNGPVFGGGTQLTVL | 172 |
| F5. | QSVLTQPPSASGTPGQTVIISCSGGGSNIGSNFGYWYQQFPGTAP KLLIYTTDRRPSGVPDRFSGSKSGTTASLAISGLRSEDEADYYCA AWDDRLSGPVFGGGTQLTVL | 173 |
| G1. | QTVVTQPPSVSGTPGQRVTISCSGSSSNIGSNSVDWYQQFPGSAP KLLIYTTNQRPSGVPDRFSGSKSGTSASLAISGLRSEDEADYYCA TWDDDLSNPKWVFGGGTKLTVL | 174 |

TABLE 4-continued

Light chain variable domain (VL) amino acid sequences of exemplary anti-PDGFRβ antibodies.

| Clone name | VL Amino Acid Sequence | SEQ ID NO. |
|---|---|---|
| E3. | DIVMTQSPLSLPVTPGEPASISCRSSQSLLHSNGYNFLDWYLQKP GQSPQLLIYLGSNRASGVPDRFSGSGSGTDFTLKISRVEAEDVGI YYCMQALQTSWTFGQGTKLEIK | 175 |
| A2. | DICRIRPLIRLTIGTITIYNYNGCCDDTVSTLPARHPWTAGLHLQ SPRRLMYQVSTRDSGVPDRFSGSGSGTDFTLRISRVEAEDVGVYY CMQGTHWPYTFGQGTKLEIRRTVA | 176 |
| D1. | DIVMTQTPLSLSVTPGQPAAISCKSSQSLVHRDGKTYLYWYLQKP GHSPQLLVYEASSRFSGVPDRISGSASGTQFTLNISRVEAEDVGL YYCMQSRNLPKTFGQGTKVEIK | 177 |
| C4. | SYELTQPTSLSASPGASASLTCTLSSGFNVVSYNIYWYQQKPGSP PQYLLRYRSDSDRHQGSGVPSRFSGSKDASANAGILVISALQSDD EADYYCMVWYSAWVFGGG | 178 |
| E1. | SYELTQPLSVSVALGQTATITCAGNNIGTYYVHWYQQRPGQAPVL VMYRDTNRPSGISDRFSGSNSGDTATLTICGVQVGDEADYYCHVL DSSTIVIFGGGTQLTVL | 179 |
| A6. | QSVLTQSPATLSVSPGERASLSCRASQSVSSNLAWYQQKPGQAPR LLIYGASTRATGIPARFSGSGSGTEFTLTISSLQSEDFAVYYCHQ YNNWPLYTFGQGTKLTVL | 180 |
| H1. | QSVLTQDPAVPVALGQTVRITCQGDSLRTYYASWYQQKPGQAPLL VIYGKNTRPSGIPVRFSGSSSGNTASLTITGAQAEDEADYYCNSR DSSGYLLLFGTGTKLTVL | 181 |
| B2. | QAVLTQEPSLTVSPGGTVTLTCGSSTGAVTSGHYPYWFQQKPGQA PRTLIYDASNKHSWTPARFSGSLLGGKAALTLSGAQPEDEAEYYC LLSYSGAGVFGTGTKVTVL | 182 |
| C2. | DIQMTQSPSSLSASVGDRVAIACRPSQDIGTDLGWYQQKPGKAPK LLIFDSSTLQSGVPSRFSGSLSGTDFILTITNLQPEDFATYYCLQ DYSFPYTFGQGTKLQIKRTVA | 183 |
| G3. | SYVLTQPPSVSVSPGQTASITCSGDELKYKYTCWYHQKPGQSPVL LIYQDTKRPSGIPERFSGSRSENTATLTISGTQAMDEADYYCQAW DSSHAVFGRGTQLTVL | 184 |
| H3. | SYVLTQPPSVSVFPGQTARITCSGSTFPKLYSFWYQQKTGQAPLL VIYKDTERPSGIPERFSGSTSGTTVTLIISGVQPEDDADYYCQSE DSRGPVFGGGTKVTVL | 185 |
| D4. | GVVMTQTPLSSLVTLGQPASISCRSSESVVHDDGNTYLSWLQQRP GQPPRLLIYKISNRFSGVPDRFSGSGAGTDFTLKISRVEPEDVGV YYCVQATHFPVTFGGGTRVEIK | 186 |
| C6. | QSALTQPASVSASPGQSVTISCTGTSDDVGRYDYVSWYQQHPGGA PKLILYDVNRRPSGVSDRFSGSKSANKASLTISGLQADDEGDYYC CSYTTGSTLYLFGTGTQLTVL | 187 |

D. Evaluation of Identified VH and VL Pairs

To evaluate the characteristics of the identified VH-VL pairs, 10-12 scFVs from each pool were constructed and produced by either in vitro translation or by *E. coli* expression, followed by affinity purification.

Figure 10:
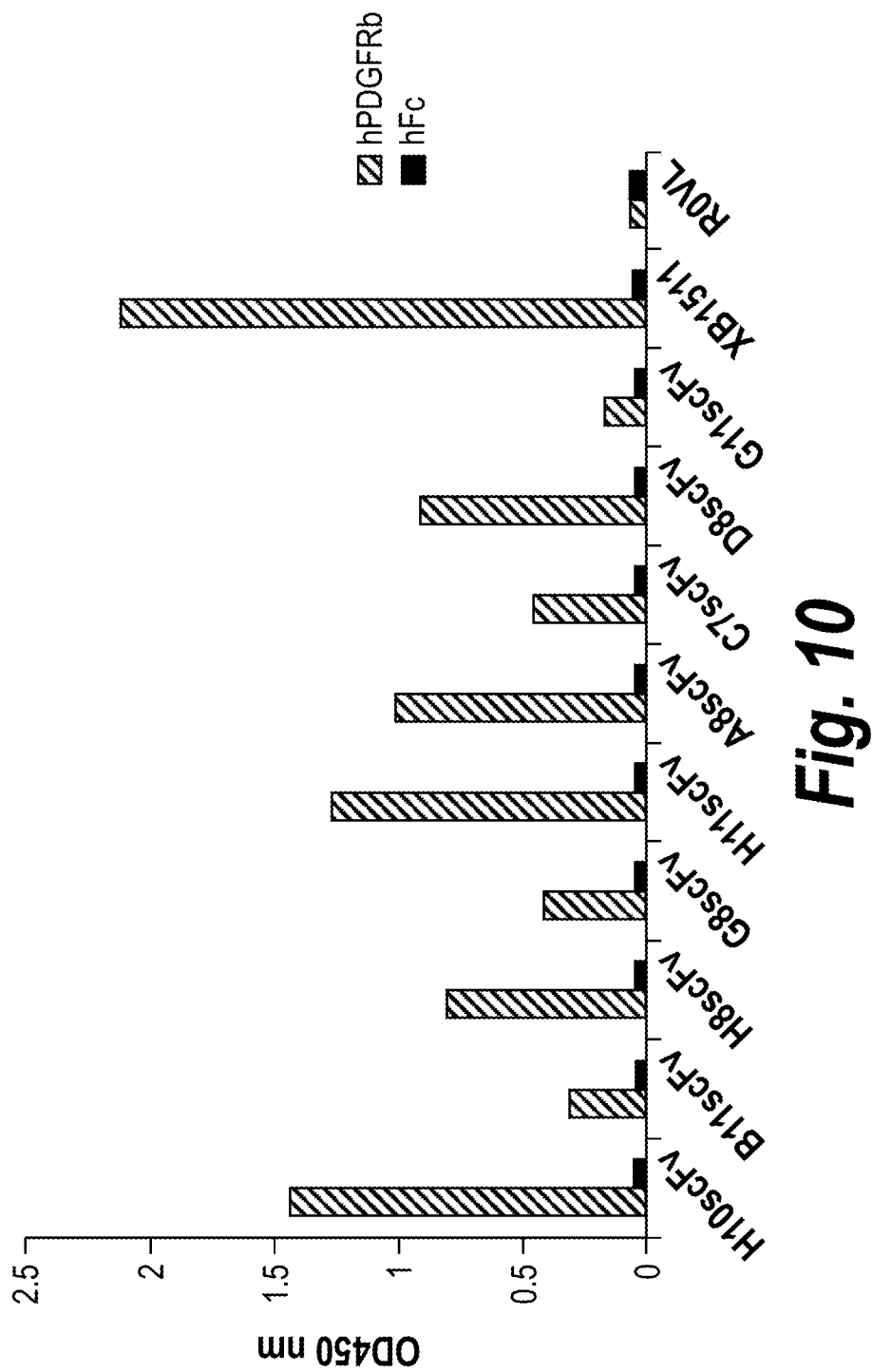
FIG. 10 depicts the results of ELISA assays measuring the binding to human PDGFRβ of XB1511/VL scFv comprising VL isolated from the second round screening pool of a VH/VL pairing DNA display screen.
Figure 11:
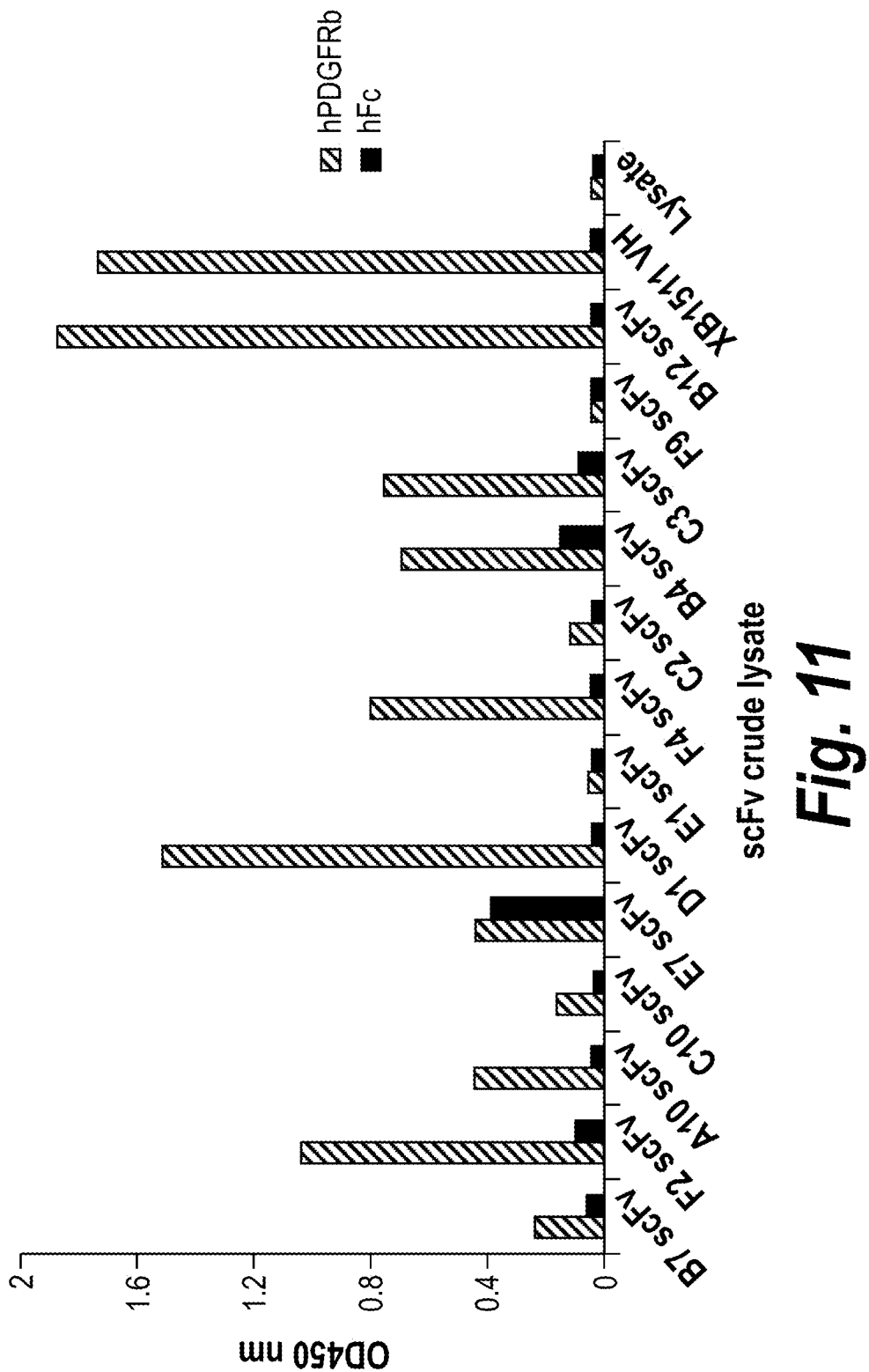
FIG. 11 depicts the results of ELISA assays measuring the binding to human PDGFRβ of XB1511/VL scFv comprising VL isolated from the third round screening pool of a VH/VL pairing DNA display screen.
Figure 12:
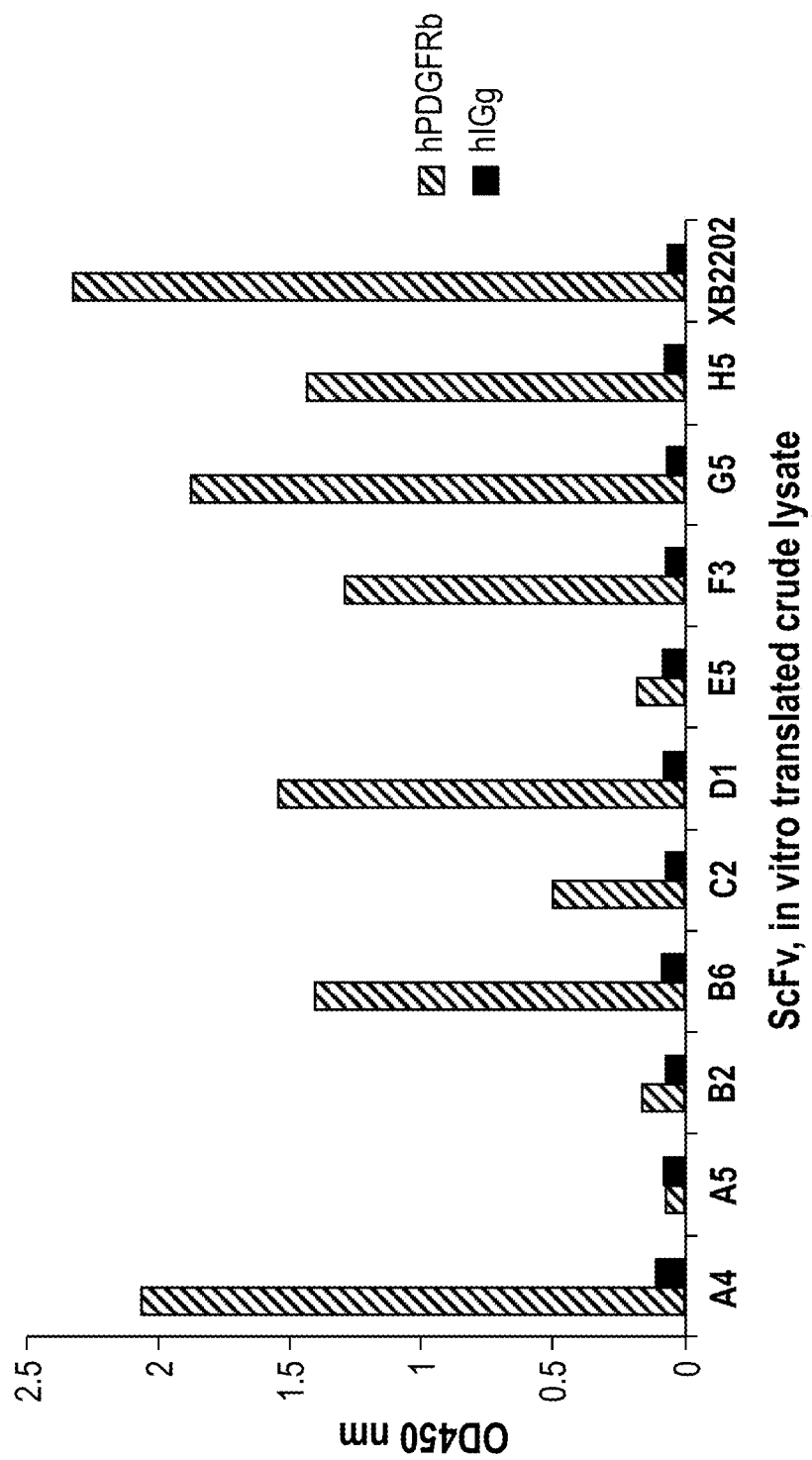
FIG. 12 depicts the results of ELISA assays measuring the binding to human PDGFRβ of XB2202/VL scFv comprising VL isolated from the second round screening pool of a VH/VL pairing DNA display screen.
Figure 13:
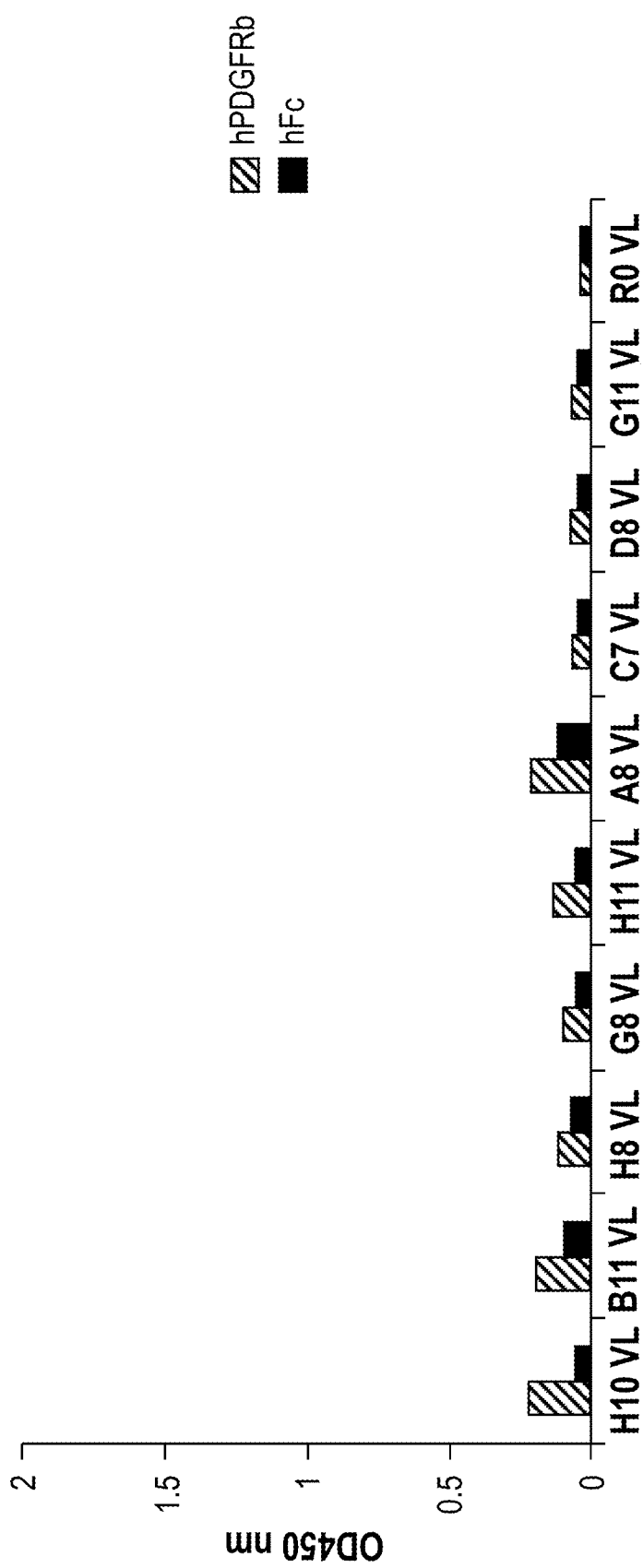
FIG. 13 depicts the results of ELISA assays measuring the binding to human PDGFRβ of unpaired VL from the XB1511/VL scFv set forth in FIG. 9.

A PDGFRβ binding ELISA assay was performed to assess the binding of the scFv to immobilized PDGFRβ and to determine the EC50. Specifically, 2 ug/mL of human PDGFRβ and human Fc or IgG in PBS was immobilized on Maxisorp plates at 4° C. overnight. The plate was then washed and blocked with superblock. In vitro translated crude scFv lysate was diluted 1:3 in 1×PBST. 100 ul of the diluted scFv lysate was loaded into each well of Maxisorp plates and incubated for 1 hour at room temperature. scFv that bound to immobilized PDGFRβ was detected by anti-flag antibody-HRP at 1:5000 dilution and a TMB substrate. The plate was read on a Molecular Device plate reader with end point assay at OD 450 nm. As shown in FIGS. 10, 11 and 12, in the ELISA binding assay, greater than 50% of the scFvs generated for XB1511 and XB2202 showed specific binding to hPDGFRβ. In contrast, the unpaired VLs alone did not show binding to PDGFRβ (see FIG. 13).

Figure 14:
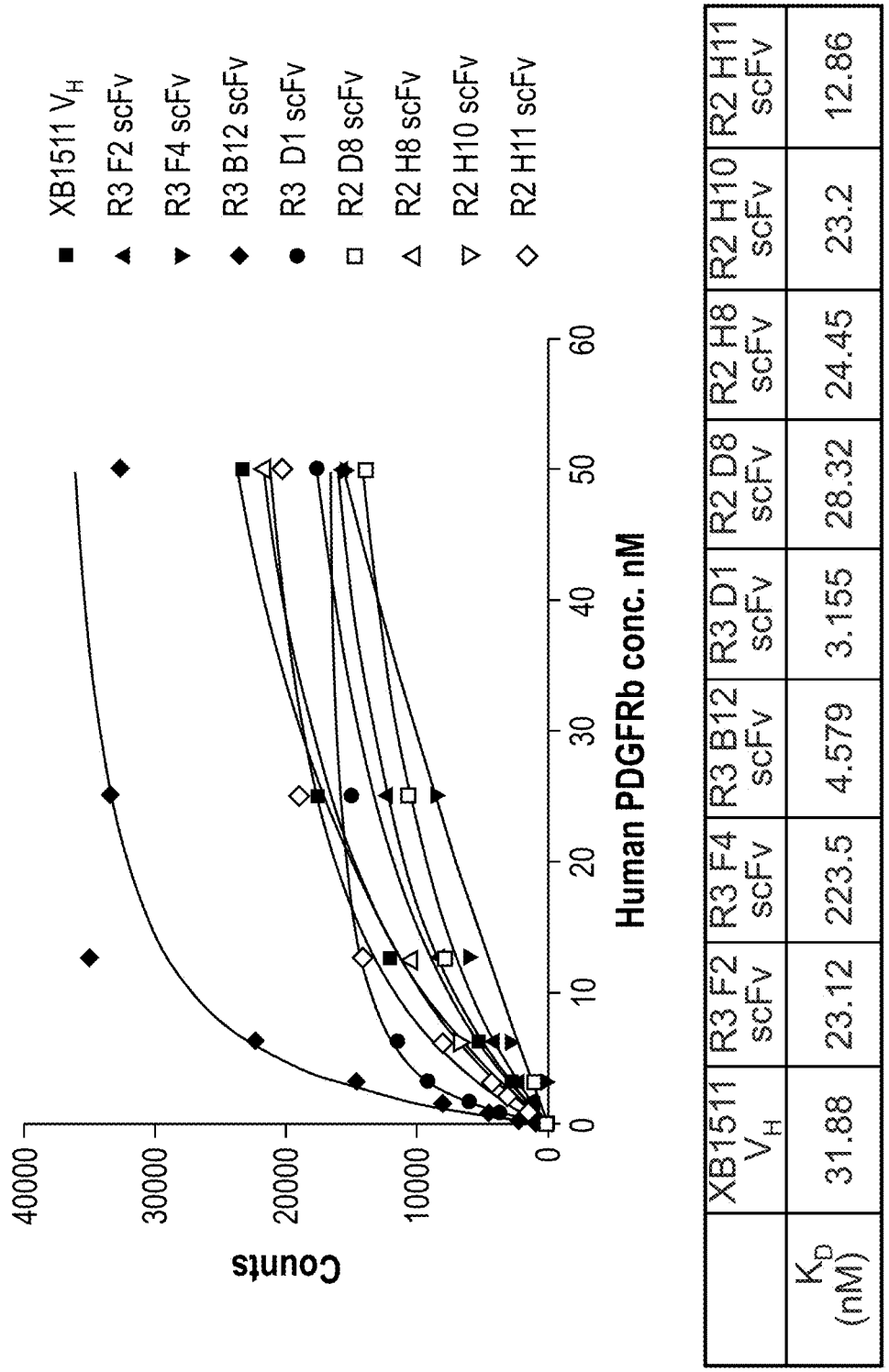
FIG. 14 depicts the results of solution binding affinity studies measuring the binding to human PDGFRβ of $^{35}$S Met labeled XB1511 VH domain and XB1511-containing scFV obtained from VH/VL pairing DNA display screens.
Figure 15:
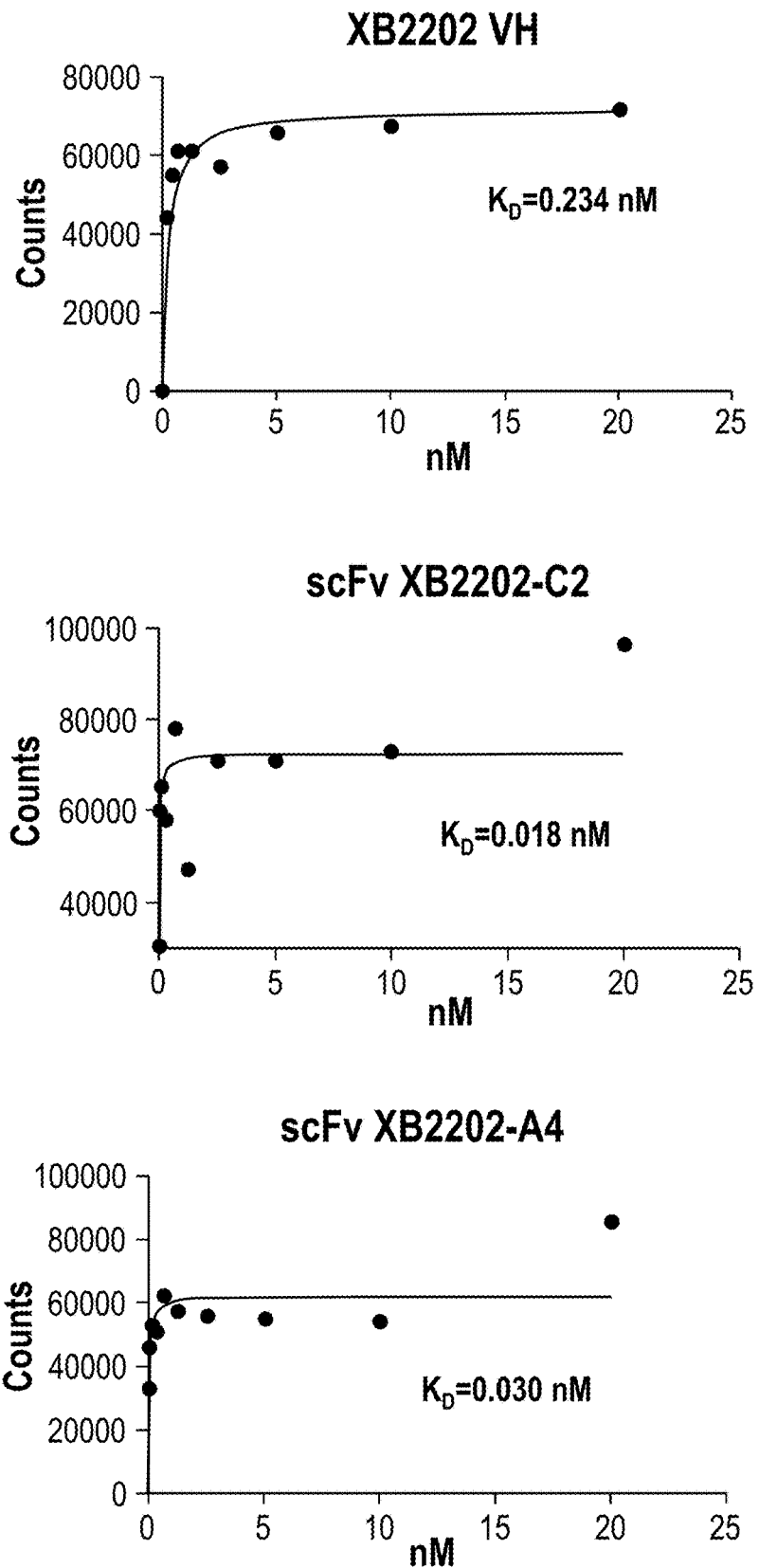
FIG. 15 depicts the results of solution binding affinity studies measuring the binding to human PDGFRβ of $^{35}$S Met labeled XB2202 VH domain and XB2202-containing scFV obtained from VH/VL pairing DNA display screens.

The affinity of several scFvs was determined by solution based equilibrium binding assay. Specifically, 120 pmol of scFv RNA was translated into free protein with $^{35}$S Met incorporated. The translated reaction mixture was 3-fold diluted in binding buffer containing 1×PBS with 0.025% triton, 1 mg/mL BSA and 0.1 mg/mL sssDNA. Human PDGFRβ was diluted in the same binding buffer to final concentrations from 100 nM to 0 nM. The diluted scFv mixture was incubated with hPDGFRβ in final volume of 100 ul on Kingfisher plates (Thermofisher Scientific, 97002084). Following incubation, 25 ul of protein A magnetic beads (Invitrogen) were used to capture the PDGFRβ from solution. The captured PDGFRβ was washed and eluted in kingfisher Reader (Thermofisher Scientific). The amount of scFv (labeled with $^{35}$S Met) bound to the magnetic bead-immobilized hPDGFRβ was counted using a scintillation counter and the Kd was calculated with Graph Pad Prism 5. For the XB1511-derived scFv tested, 2 scFv showed an 8-10 fold higher $K_D$, 1 showed 2.5 fold higher $K_D$, and 4 showed a similar $K_D$ when compared to XB1511 VH alone (FIG. 14). Only 1 scFv showed a lower $K_D$ than XB1511 VH alone. As shown in FIG. 15, both of the XB2202-derived scFv tested showed approximately an 8-10 fold better $K_D$ when compared to XB2202 VH alone.

Figure 16:
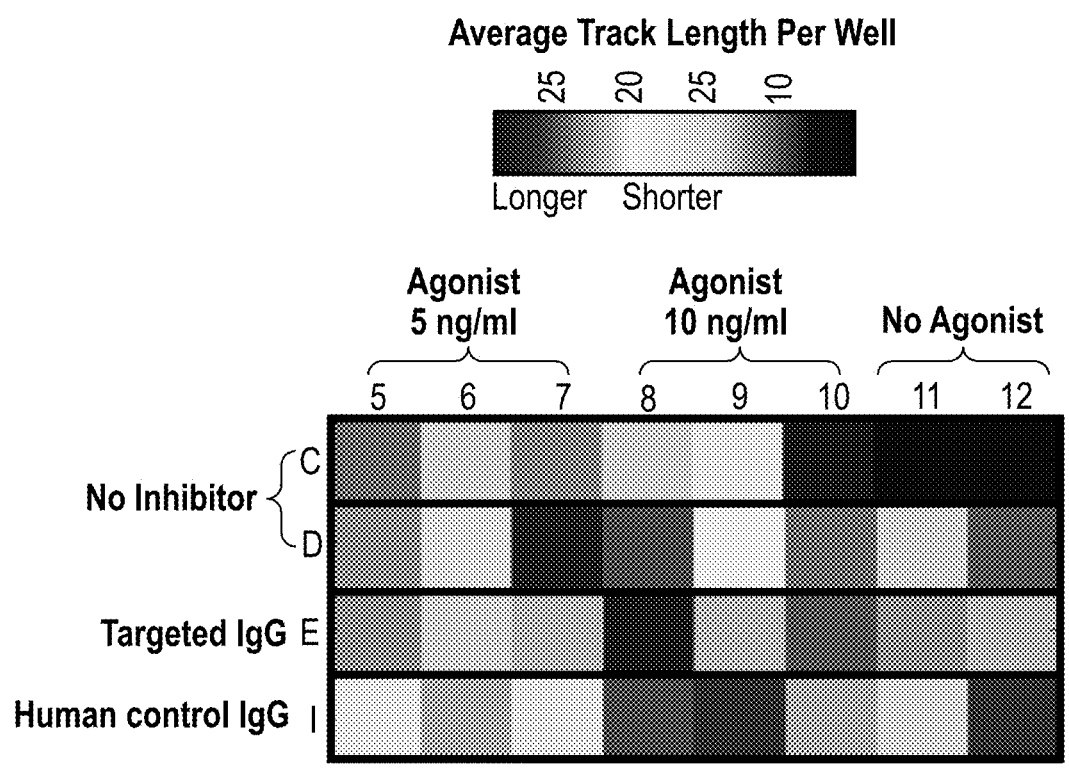
FIG. 16 depicts the results of label-free migration assays measuring the ability of an XB1511-containing IgG1 to inhibit the migration of human foreskin fibroblasts.

Example 4. Conversion of VH-VL Pairs to Heterotetrameric IgG and Demonstration of Biological Activity XB1511 VH and D8 VL were expressed as heterotetrameric IgG in 293T cells. Cell culture supernatant was collected after 48 hours and 96 hours and the expressed IgG was purified with protein A agarose beads. The IgG was produced at 8 mg/L without any optimization. To evaluate the biological activity of the XB1511/D8 IgG, HFF-1 human foreskin fibroblasts were seeded in 384-well BIND biosensors and allowed to attach overnight in serum-free media. The fibroblast cells were then stimulated with 5 ng/mL or 10 ng/mL of PDGFBB ligand and allowed to migrate for 18 hours. BIND Scanner images were captured every 15 minutes and software analysis tools used to measure the track lengths of individual cell migration responses. Track length is represented by a "heat map" from blue (no migration) to red (maximal migration). As shown in FIG. 16, the XB1511/D8 IgG was able to completely block the PDGFBB-induced migration of human fibroblasts.

Example 5. scFv Thermostability

Figure 17:
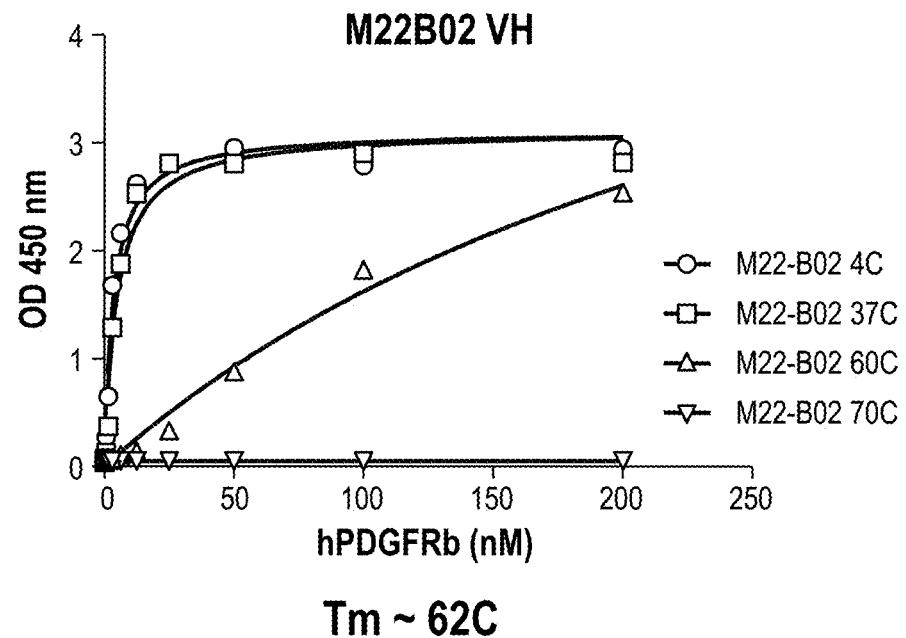
FIG. 17 depicts the results of ELISA assays measuring the binding to human PDGFRβ of XB2202 VH and XB2202/A4 scFv after incubation at various temperatures.
Figure 17:
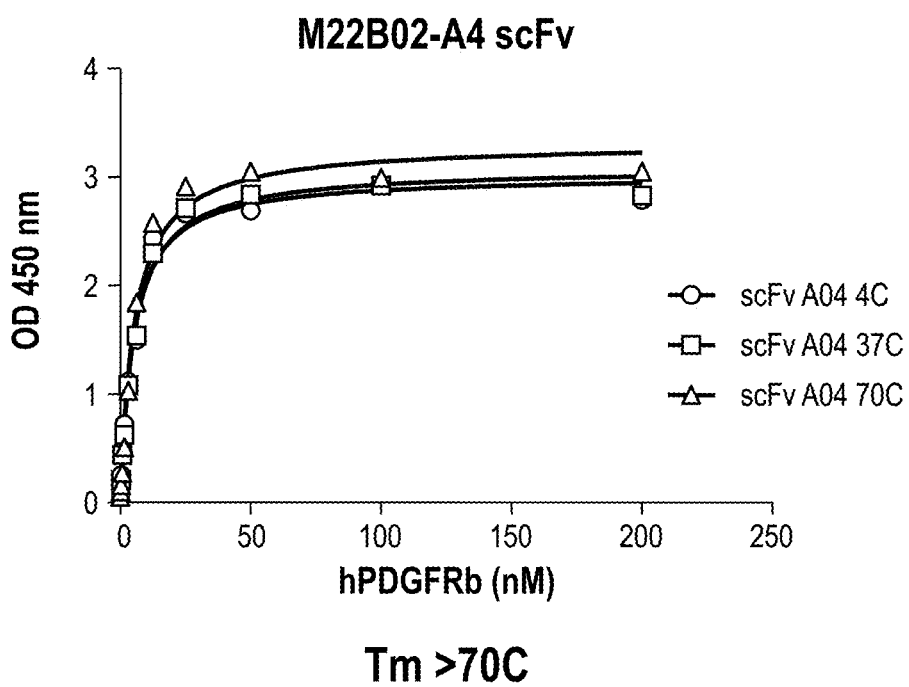

The thermostability of the XB2202 VH and scFv XB2202-A4 were determined. Specifically, 1 mg/mL of XB2202 and XB2202-A4 were incubated at 4 C, 37 C, 60 C and 70 C for 12 hours and PDGFRβ binding ELISA was performed to test the binding activity of the protein after incubation. As shown in FIG. 17, XB2202 VH lost significant PDGFRβ binding activity after incubation at 60 C and completely lost binding activity after incubation at 70 C. The Tm of XB2202 was measured to be approximately 62 C. In contrast, scFv XB2202-A4 was completely active after 12 hour incubation at 70 C, indicating that the Tm of scFv XB2202 was greater than 70 C.

We claim:

1. A method for selecting a bispecific, stable VH/VL pair, the method comprising:
    (a) providing an unpaired VH domain that binds specifically to a first antigen;
    (b) contacting the unpaired VH domain with a library of unpaired VL domains such that a library of VH/VL pairs is formed;
    (c) contacting the library of VH/VL pairs with a second antigen;
    (d) selecting from the library of VH/VL pairs at least one VH/VL pair that binds specifically to the second antigen;
    (e) contacting the VH/VL pair(s) selected in step (d) with the first antigen; and
    (f) selecting at least one VH/VL pair that binds specifically to the first antigen, thereby selecting a bispecific, stable VH/VL pair.

2. The method of claim 1, further comprising the step of introducing additional amino acid sequence diversity into the library of unpaired VL domains of step (b).

3. The method of claim 2, wherein the additional amino acid sequence diversity is introduced by random mutagenesis.

4. The method of claim 1, wherein the library of unpaired VL domains of step (b) comprises human VL domains.

5. The method of claim 1, wherein the library of unpaired VL domains is a nucleic acid display library.

6. The method of claim 1, wherein the unpaired VH domain of step (a) is produced by
    (a) providing a library of chimeric, unpaired VH domains wherein diversity lies in the FR1-FR3 regions, and wherein each member of the library comprises the CDR3 region sequence from the VH domain of a reference antibody that binds specifically to the first antigen;
    (b) contacting the library with the first antigen; and
    (c) selecting from the library at least one chimeric, unpaired VH domain that binds specifically to the first antigen, thereby producing an unpaired VH domain that binds specifically to the first antigen.

7. The method of claim 1, further comprising the step of expressing the selected VH/VL pair in a cell.

8. The method of claim 1, wherein the library is generated using at least one oligonucleotide having a sequence selected from the group consisting of SEQ ID NOs: 4, 5, 6, 7, 8, 9, 10, 11, 12, 13, 14, 15, 16, 17, 18, 19, 20, 21, 70, 71, 72, 73, 74, 75, 75, 76, 77, 78, 79, 80, 81, 82, 83, 84, 85, 86, 87, 88, 89, 90, 91, 92, 93, 94, 95, 96, 97, 98, 99, 100, 101, and 102.

9. The method of claim 1, wherein the library of VH/VL pairs is a nucleic acid display library.

10. The method of claim 1, further comprising the step of expressing an antibody comprising the VH/VL pair in a cell.

* * * * *

SEQUENCE LISTING

```
<160> NUMBER OF SEQ ID NOS: 187

<210> SEQ ID NO 1
<211> LENGTH: 116
<212> TYPE: PRT
<213> ORGANISM: Artificial Sequence
<220> FEATURE:
<223> OTHER INFORMATION: Synthetic amino acid - clone name: A4 XB1511

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Gly Gly Asp Arg Ser Tyr Trp Gly Gln Gly Thr Leu Val
            100                 105                 110

Thr Val Ser Ser
        115

<210> SEQ ID NO 2
<211> LENGTH: 116
<212> TYPE: PRT
<213> ORGANISM: Artificial Sequence
<220> FEATURE:
<223> OTHER INFORMATION: Synthetic amino acid - clone name: B4
```

-continued

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile His Gly Gly Asp Arg Ser Tyr Trp Gly Gln Gly Thr Leu Val
            100                 105                 110

Thr Val Ser Ser
        115

<210> SEQ ID NO 3
<211> LENGTH: 116
<212> TYPE: PRT
<213> ORGANISM: Artificial Sequence
<220> FEATURE:
<223> OTHER INFORMATION: Synthetic amino acid - clone name: G2

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Lys Asp Thr Ala Val Tyr Tyr Cys
                85                  90                  95

Ala Ile His Gly Gly Asp Arg Ser Tyr Trp Gly Gln Gly Thr Leu Val
            100                 105                 110

Thr Val Ser Ser
        115

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide: FR3 Reverse

<400> SEQUENCE: 4
cgcacagtaa tacacggc                                                 18

<210> SEQ ID NO 5
<211> LENGTH: 46
<212> TYPE: DNA
<213> ORGANISM: Artificial Sequence
<220> FEATURE:

<223> OTHER INFORMATION: Synthetic oligonucleotide: VH1a

<400> SEQUENCE: 5
caattactat ttacaattac aatgcaggtk cagctggtgc agtctg         46

<210> SEQ ID NO 6
<211> LENGTH: 46
<212> TYPE: DNA
<213> ORGANISM: Artificial Sequence
<220> FEATURE:
<223> OTHER INFORMATION: Synthetic oligonucleotide: VH1b

<400> SEQUENCE: 6
caattactat ttacaattac aatgcaggtc cagcttgtgc agtctg         46

<210> SEQ ID NO 7
<211> LENGTH: 46
<212> TYPE: DNA
<213> ORGANISM: Artificial Sequence
<220> FEATURE:
<223> OTHER INFORMATION: Synthetic oligonucleotide: VH1c

<400> SEQUENCE: 7
caattactat ttacaattac aatgsaggtc cagctggtac agtctg         46

<210> SEQ ID NO 8
<211> LENGTH: 46
<212> TYPE: DNA
<213> ORGANISM: Artificial Sequence
<220> FEATURE:
<223> OTHER INFORMATION: Synthetic oligonucleotide: VH1d

<400> SEQUENCE: 8
caattactat ttacaattac aatgcaratg cagctggtgc agtctg         46

<210> SEQ ID NO 9
<211> LENGTH: 46
<212> TYPE: DNA
<213> ORGANISM: Artificial Sequence
<220> FEATURE:
<223> OTHER INFORMATION: Synthetic oligonucleotide: VH2

<400> SEQUENCE: 9
caattactat ttacaattac aatgcagrtc accttgaagg agtctg         46

<210> SEQ ID NO 10
<211> LENGTH: 46
<212> TYPE: DNA
<213> ORGANISM: Artificial Sequence
<220> FEATURE:
<223> OTHER INFORMATION: Synthetic oligonucleotide: VH3a

<400> SEQUENCE: 10
caattactat ttacaattac aatggargtg cagctggtgg agtctg         46

<210> SEQ ID NO 11
<211> LENGTH: 46
<212> TYPE: DNA
<213> ORGANISM: Artificial Sequence
<220> FEATURE:
<223> OTHER INFORMATION: Synthetic oligonucleotide: VH3b

<400> SEQUENCE: 11
caattactat ttacaattac aatgcaggtg cagctggtgg agtctg         46

```
<210> SEQ ID NO 12
<211> LENGTH: 46
<212> TYPE: DNA
<213> ORGANISM: Artificial Sequence
<220> FEATURE:
<223> OTHER INFORMATION: Synthetic oligonucleotide: VH3c

<400> SEQUENCE: 12
caattactat ttacaattac aatggaggtg cagctgttgg agtctg                    46

<210> SEQ ID NO 13
<211> LENGTH: 42
<212> TYPE: DNA
<213> ORGANISM: Artificial Sequence
<220> FEATURE:
<223> OTHER INFORMATION: Synthetic oligonucleotide: VH4a

<400> SEQUENCE: 13
caattactat ttacaattac aatgcagstg cagctgcagg ag                        42

<210> SEQ ID NO 14
<211> LENGTH: 45
<212> TYPE: DNA
<213> ORGANISM: Artificial Sequence
<220> FEATURE:
<223> OTHER INFORMATION: Synthetic oligonucleotide: VH4b

<400> SEQUENCE: 14
caattactat ttacaattac aatgcaggtg cagctacagc agtgg                     45

<210> SEQ ID NO 15
<211> LENGTH: 46
<212> TYPE: DNA
<213> ORGANISM: Artificial Sequence
<220> FEATURE:
<223> OTHER INFORMATION: Synthetic oligonucleotide: VH5

<400> SEQUENCE: 15
caattactat ttacaattac aatggargtg cagctggtgc agtctg                    46

<210> SEQ ID NO 16
<211> LENGTH: 46
<212> TYPE: DNA
<213> ORGANISM: Artificial Sequence
<220> FEATURE:
<223> OTHER INFORMATION: Synthetic oligonucleotide: VH6

<400> SEQUENCE: 16
caattactat ttacaattac aatgcaggta cagctgcagc agtcag                    46

<210> SEQ ID NO 17
<211> LENGTH: 46
<212> TYPE: DNA
<213> ORGANISM: Artificial Sequence
<220> FEATURE:
<223> OTHER INFORMATION: Synthetic oligonucleotide: VH7

<400> SEQUENCE: 17
caattactat ttacaattac aatgcaggtg cagctggtgc aatctg                    46

<210> SEQ ID NO 18
<211> LENGTH: 42
<212> TYPE: DNA
<213> ORGANISM: Artificial Sequence
<220> FEATURE:
<223> OTHER INFORMATION: Synthetic oligonucleotide: T7TMVUTR
```

<400> SEQUENCE: 18
taatacgact cactataggg acaattacta tttacaatta ca                                 42

<210> SEQ ID NO 19
<211> LENGTH: 75
<212> TYPE: DNA
<213> ORGANISM: Artificial Sequence
<220> FEATURE:
<223> OTHER INFORMATION: Synthetic oligonucleotide: XB1511 FR3CDR3FR4
      Reverse

<400> SEQUENCE: 19
tgaggagacg gtgaccaggg ttccctggcc ccagtagctc ctgtcgcccc catgtktcgc              60
acagtaatac acggc                                                              75

<210> SEQ ID NO 20
<211> LENGTH: 39
<212> TYPE: DNA
<213> ORGANISM: Artificial Sequence
<220> FEATURE:
<223> OTHER INFORMATION: Synthetic oligonucleotide: FR4 Cu3 Reverse

<400> SEQUENCE: 20
ggagacgagg gggaaaaggg ttgaggagac ggtgaccag                                    39

<210> SEQ ID NO 21
<211> LENGTH: 87
<212> TYPE: DNA
<213> ORGANISM: Artificial Sequence
<220> FEATURE:
<223> OTHER INFORMATION: Synthetic oligonucleotide: Y109

<400> SEQUENCE: 21
tttttttttt ttttttttt aaatagcgga tgctaaggac gacttgtcgt cgtcgtcctt              60
gtagtcggag acgaggggga aagggt                                                  87

<210> SEQ ID NO 22
<211> LENGTH: 116
<212> TYPE: PRT
<213> ORGANISM: Artificial Sequence
<220> FEATURE:
<223> OTHER INFORMATION: Synthetic amino acid - clone name: XB2202

<400> SEQUENCE: 22

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: Synthetic amino acid - clone name: C4

<400> SEQUENCE: 23

```
Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Gly Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115
```

<210> SEQ ID NO 24
<211> LENGTH: 116
<212> TYPE: PRT
<213> ORGANISM: Artificial Sequence
<220> FEATURE:
<223> OTHER INFORMATION: Synthetic amino acid - clone name: B12

<400> SEQUENCE: 24

```
Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asn Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115
```

<210> SEQ ID NO 25
<211> LENGTH: 116
<212> TYPE: PRT
<213> ORGANISM: Artificial Sequence
<220> FEATURE:
<223> OTHER INFORMATION: Synthetic amino acid - clone name: D07

```
<400> SEQUENCE: 25

Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial Sequence
<220> FEATURE:
<223> OTHER INFORMATION: Synthetic amino acid - clone name: C05

<400> SEQUENCE: 26

Gln Met Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45

Gly Gly Val Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Synthetic amino acid - clone name: E05

<400> SEQUENCE: 27

Gln Val Gln Leu Val Gln Ser Gly Pro Lys Val Lys Lys Pro Gly Ser
1               5                   10                  15

Ser Val Arg Val Ser Cys Lys Ala Ser Gly Gly Thr Phe Ser Arg His
            20                  25                  30

Ala Ile Ser Trp Val Arg Gln Ala Pro Gly Gln Gly Leu Glu Trp Ile
        35                  40                  45
```

Gly Gly Ile Leu Pro Ile Leu Lys Thr Pro Asn Tyr Ala Gln Arg Phe
            50                  55                  60

Gln Gly Arg Val Thr Ile Asn Ala Asp Glu Ser Thr Ser Thr Val Tyr
 65                  70                  75                  80

Met Glu Met Ser Ser Leu Arg Ser Glu Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: Synthetic amino acid - clone name: E2

<400> SEQUENCE: 28

Gln Met Gln Leu Val Gln Ser Gly Ala Glu Val Lys Lys Pro Gly Ala
 1               5                  10                  15

Ser Val Lys Ile Ser Cys Lys Thr Ser Gly Tyr Thr Phe Thr Asp Tyr
                20                  25                  30

Tyr Ile Gln Trp Val Arg Gln Ala Pro Gly Gln Gly Leu Glu Trp Val
            35                  40                  45

Gly Trp Ile Asn Pro Asn Ser Gly Asn Thr Gly Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr His Gly Gly Asp Tyr Ser Tyr Trp Gly Gln Gly Thr Leu Val
                100                 105                 110

Thr Val Ser Ser
        115

<210> SEQ ID NO 29
<211> LENGTH: 116
<212> TYPE: PRT
<213> ORGANISM: Artificial Sequence
<220> FEATURE:
<223> OTHER INFORMATION: Synthetic amino acid - clone name: A3

<400> SEQUENCE: 29

Gln Val Gln Leu Val Gln Ser Gly Ala Glu Val Lys Lys Pro Gly Ala
 1               5                  10                  15

Ser Val Arg Val Ser Cys Lys Ala Ser Gly Tyr Thr Phe Ser Asp Tyr
                20                  25                  30

Tyr Ile Gln Trp Val Arg Gln Ala Pro Gly Gln Gly Leu Glu Trp Met
            35                  40                  45

Gly Trp Ile Asn Pro Asn Ser Gly Gly Thr Tyr Phe Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Ser Leu Thr Ser Asp Asp Thr Ala Val Tyr Tyr Cys
                 85                  90                  95

Ala Thr His Gly Gly Asp Arg Gly Tyr Trp Gly Gln Gly Thr Leu Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: Synthetic amino acid - clone name: C3

<400> SEQUENCE: 30

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Gln Trp Val Arg Gln Ala Pro Gly Gln Gly Leu Glu Trp Ile
        35                  40                  45

Gly Gly Ile Leu Pro Ile Leu Lys Thr Pro Asn Tyr Ala Gln Arg Phe
    50                  55                  60

Gln Gly Arg Val Thr Ile Asn Ala Asp Glu Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Synthetic amino acid - clone name: F10

<400> SEQUENCE: 31

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Gln Trp Val Arg Gln Ala Pro Gly Gln Gly Leu Glu Trp Met
        35                  40                  45

Gly Trp Ile Asn Pro Asp Ser Gly Gly Thr Tyr Phe Ala Gln Lys Phe
    50                  55                  60

Gln Gly Arg Val Ala Met Thr Arg Asp Thr Ser Ile Asn Thr Ala Tyr
65                  70                  75                  80

Met Glu Leu Ser Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 32
<211> LENGTH: 116
<212> TYPE: PRT

<213> ORGANISM: Artificial Sequence
<220> FEATURE:
<223> OTHER INFORMATION: Synthetic amino acid - clone name: C12

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Gln Trp Val Arg Gln Ala Pro Gly Glu Gly Leu Glu Trp Met
        35                  40                  45

Gly Trp Met Asn Pro Asp Ser Gly Thr Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Pro Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 33
<211> LENGTH: 116
<212> TYPE: PRT
<213> ORGANISM: Artificial Sequence
<220> FEATURE:
<223> OTHER INFORMATION: Synthetic amino acid - clone name: H2

<400> SEQUENCE: 33

Gln Met Gln Leu Val Gln Ser Gly Ala Glu Val Lys Asn Pro Gly Ala
1               5                   10                  15

Ser Val Lys Val Ser Cys Lys Ala Ser Gly Tyr Pro Phe Ser Ala Tyr
            20                  25                  30

Tyr Ile Gln Trp Val Arg Gln Ala Pro Gly Gln Gly Leu Glu Trp Met
        35                  40                  45

Gly Trp Leu Asn Pro Asn Ser Gly Asp Thr His Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Thr Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 34
<211> LENGTH: 116
<212> TYPE: PRT
<213> ORGANISM: Artificial Sequence
<220> FEATURE:
<223> OTHER INFORMATION: Synthetic amino acid - clone name: F11

<400> SEQUENCE: 34

Gln Met Gln Leu Val Gln Ser Gly Ala Glu Val Lys Asn Pro Gly Ala
1               5                   10                  15

Ser Val Lys Val Ser Cys Lys Ala Ser Gly Tyr Pro Phe Ser Ala Tyr
            20                  25                  30

```
Tyr Ile Gln Trp Val Arg Gln Ala Pro Gly Gln Gly Leu Glu Trp Met
            35                  40                  45

Gly Trp Leu Asn Pro Asn Ser Gly Asp Thr His Ser Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Gly Pro Thr Ser Asp Thr Ala Val Tyr Tyr Cys
                 85                  90                  95

Ala Thr His Gly Gly Asp Arg Ser Tyr Trp Gly Gln Gly Thr Leu Val
            100                 105                 110

Thr Val Ser Ser
         115

<210> SEQ ID NO 35
<211> LENGTH: 116
<212> TYPE: PRT
<213> ORGANISM: Artificial Sequence
<220> FEATURE:
<223> OTHER INFORMATION: Synthetic amino acid - clone name: B1

<400> SEQUENCE: 35

Gln Met Gln Leu Val Gln Ser Gly Ala Glu Val Arg Lys Pro Gly Ala
 1               5                  10                  15

Ser Val Lys Val Ser Cys Lys Ala Ser Gly Tyr Ser Phe Ser Asp Tyr
            20                  25                  30

Tyr Ile His Trp Val Arg Gln Ala Pro Gly Gln Gly Leu Glu Trp Ile
            35                  40                  45

Gly Trp Ile Asn Pro Asn Asn Gly Asn Thr Thr Tyr Ala Gln Lys Phe
 50                  55                  60

Gln Gly Arg Val Thr Met Ile Arg Asp Thr Ser Ile Ser Thr Ala Tyr
 65                  70                  75                  80

Met Glu Leu Ser Glu Leu Arg Ser Asp Asp Thr Ala Val Tyr Tyr Cys
                 85                  90                  95

Ala Thr His Gly Gly Asp Arg Ser Tyr Trp Gly Gln Gly Thr Leu Val
            100                 105                 110

Thr Val Ser Ser
         115

<210> SEQ ID NO 36
<211> LENGTH: 116
<212> TYPE: PRT
<213> ORGANISM: Artificial Sequence
<220> FEATURE:
<223> OTHER INFORMATION: Synthetic amino acid - clone name: E11

<400> SEQUENCE: 36

Gln Val Gln Leu Val Gln Ser Gly Ala Glu Val Glu Lys Pro Gly Ala
 1               5                  10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
            35                  40                  45

Arg Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: Synthetic amino acid - clone name: H1

<400> SEQUENCE: 37

Glu Val Gln Leu Leu Glu Ser Gly Ala Glu Val Lys Gln Pro Gly Ala
1               5                   10                  15

Ser Val Lys Val Ser Cys Lys Thr Ser Gly Tyr Thr Phe Thr Asp Tyr
            20                  25                  30

His Leu His Trp Val Arg Gln Ala Pro Gly Gln Gly Leu Glu Trp Met
        35                  40                  45

Gly Trp Ile Asn Pro Asn Ser Gly Gly Thr Asn Ser Ala Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Thr Ser Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 38
<211> LENGTH: 116
<212> TYPE: PRT
<213> ORGANISM: Artificial Sequence
<220> FEATURE:
<223> OTHER INFORMATION: Synthetic amino acid - clone name: E6

<400> SEQUENCE: 38

Gln Met Gln Leu Val Gln Ser Gly Ala Glu Val Lys Arg Pro Gly Ala
1               5                   10                  15

Ser Val Lys Val Pro Cys Lys Ala Ser Gly Tyr Thr Phe Thr Asp Tyr
            20                  25                  30

Tyr Leu His Trp Val Arg Gln Ala Pro Gly Gln Gly Leu Lys Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115
```

```
<210> SEQ ID NO 39
<211> LENGTH: 116
<212> TYPE: PRT
<213> ORGANISM: Artificial Sequence
<220> FEATURE:
<223> OTHER INFORMATION: Synthetic amino acid - clone name: A1

<400> SEQUENCE: 39

Gln Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial Sequence
<220> FEATURE:
<223> OTHER INFORMATION: Synthetic amino acid - clone name: H7

<400> SEQUENCE: 40

Gln Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 41
<211> LENGTH: 116
<212> TYPE: PRT
<213> ORGANISM: Artificial Sequence
<220> FEATURE:
<223> OTHER INFORMATION: Synthetic amino acid - clone name: G04

<400> SEQUENCE: 41

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Phe Thr Phe Thr Ser Tyr
            20                  25                  30

Ala Ile Ser Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 42
<211> LENGTH: 116
<212> TYPE: PRT
<213> ORGANISM: Artificial Sequence
<220> FEATURE:
<223> OTHER INFORMATION: Synthetic amino acid - clone name: B2

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Gln Val Gln Trp Val Arg Gln Ala Pro Gly Gln Gly Leu Glu Trp Leu
        35                  40                  45

Gly Val Ile Asn Thr Gly Val Gly Ser Thr Asn Tyr Ala Gln Lys Phe
50                  55                  60

Gln Gly Arg Val Thr Met Thr Arg Asp Thr Ala Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 43
<211> LENGTH: 116
<212> TYPE: PRT
<213> ORGANISM: Artificial Sequence
<220> FEATURE:
<223> OTHER INFORMATION: Synthetic amino acid - clone name: A7

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Pro Val Gln Trp Val Arg Gln Ala Pro Gly Gln Gly Leu Glu Trp Leu
        35                  40                  45

Gly Val Ile Asn Thr Gly Val Gly Ser Thr Asn Tyr Ala Gln Lys Phe
50                  55                  60
```

```
Gln Gly Arg Val Thr Met Thr Arg Asp Thr Ala Thr Ser Ile Val Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 44
<211> LENGTH: 116
<212> TYPE: PRT
<213> ORGANISM: Artificial Sequence
<220> FEATURE:
<223> OTHER INFORMATION: Synthetic amino acid - clone name: H3

<400> SEQUENCE: 44

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Ser
                20                  25                  30

Phe Met Gln Trp Val Arg Gln Val Pro Gly Gln Arg Leu Glu Trp Val
            35                  40                  45

Gly Leu Ser Asn Pro Ser Gly Asp Tyr Thr Val Tyr Ala Pro Lys Phe
        50                  55                  60

Gln Gly Arg Val Thr Met Thr Thr Asp Thr Ala Thr Ser Thr Phe Tyr
65                  70                  75                  80

Met Glu Leu Phe Ser Leu Arg Ser Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
            115

<210> SEQ ID NO 45
<211> LENGTH: 116
<212> TYPE: PRT
<213> ORGANISM: Artificial Sequence
<220> FEATURE:
<223> OTHER INFORMATION: Synthetic amino acid - clone name: B4

<400> SEQUENCE: 45

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Asn Ser
                20                  25                  30

Phe Met Gln Trp Val Arg Gln Val Pro Gly Gln Arg Leu Glu Trp Val
            35                  40                  45

Gly Leu Ser Asn Pro Ser Gly Asp Tyr Thr Val Tyr Ala Pro Lys Leu
        50                  55                  60

Gln Gly Arg Val Thr Met Thr Thr Asp Thr Ala Thr Gly Thr Phe Tyr
65                  70                  75                  80

Met Glu Leu Phe Ser Leu Arg Ser Asp Asp Thr Ala Val Tyr Tyr Cys
                85                  90                  95
```

```
Ala Thr His Gly Gly Asp Arg Ser Tyr Trp Gly Gln Gly Thr Leu Val
            100                 105                 110

Thr Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Synthetic amino acid - clone name: H05

<400> SEQUENCE: 46

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Phe Ile Leu Phe Asp Gly Asn Asn Lys Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 47
<211> LENGTH: 116
<212> TYPE: PRT
<213> ORGANISM: Artificial Sequence
<220> FEATURE:
<223> OTHER INFORMATION: Synthetic amino acid - clone name: D06

<400> SEQUENCE: 47

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Asp Arg Ser Tyr Trp Gly Gln Gly Thr Leu Val
            100                 105                 110

Thr Val Ser Ser
        115

<210> SEQ ID NO 48
<211> LENGTH: 116
<212> TYPE: PRT
```

<213> ORGANISM: Artificial Sequence
<220> FEATURE:
<223> OTHER INFORMATION: Synthetic amino acid - clone name: F3

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser His
            20                  25                  30

Gly Met Ser Trp Val Arg Gln Ala Pro Gly Gln Gly Leu Glu Trp Met
        35                  40                  45

Gly Trp Ile Ser Ala Asp Asn Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 49
<211> LENGTH: 116
<212> TYPE: PRT
<213> ORGANISM: Artificial Sequence
<220> FEATURE:
<223> OTHER INFORMATION: Synthetic amino acid - clone name: A12

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser His
            20                  25                  30

Gly Met Ser Trp Val Arg Gln Ala Pro Gly Gln Gly Leu Glu Trp Met
        35                  40                  45

Gly Trp Ile Ser Ala Asp Asn Gly Asn Thr Lys Tyr Ala Gln Lys Phe
    50                  55                  60

Gln Asp Arg Val Thr Leu Thr Thr Asp Thr Ser Thr Ser Thr Ala Tyr
65                  70                  75                  80

Leu Glu Leu Arg Ser Leu Arg Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 50
<211> LENGTH: 116
<212> TYPE: PRT
<213> ORGANISM: Artificial Sequence
<220> FEATURE:
<223> OTHER INFORMATION: Synthetic amino acid - clone name: G3

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 51
<211> LENGTH: 116
<212> TYPE: PRT
<213> ORGANISM: Artificial Sequence
<220> FEATURE:
<223> OTHER INFORMATION: Synthetic amino acid - clone name: F05

<400> SEQUENCE: 51

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Leu Thr Glu Leu
            20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                 85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 52
<211> LENGTH: 116
<212> TYPE: PRT
<213> ORGANISM: Artificial Sequence
<220> FEATURE:
<223> OTHER INFORMATION: Synthetic amino acid - clone name: H12

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asn
            20                  25                  30

Tyr Val His Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
            85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: Synthetic amino acid - clone name: G12

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Asn Ala Tyr
            20                  25                  30

Pro Ile Ser Trp Val Arg Gln Ala Pro Gly Gln Gly Leu Glu Trp Met
        35                  40                  45

Gly Gly Ile Ile Pro Val Ser Gly Thr Pro Asn Tyr Ala Gln Lys Phe
    50                  55                  60

Gln Gly Arg Val Thr Ile Thr Ala Asp Lys Ser Thr Tyr Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 54
<211> LENGTH: 116
<212> TYPE: PRT
<213> ORGANISM: Artificial Sequence
<220> FEATURE:
<223> OTHER INFORMATION: Synthetic amino acid - clone name: C06

<400> SEQUENCE: 54

Gln Met Gln Leu Val Gln Ser Gly Ala Glu Val Lys Lys Pro Gly Ala
1               5                   10                  15

Ser Val Lys Val Ser Cys Met Ala Ser Gly Tyr Thr Phe Thr Gly His
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Thr Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115
```

-continued

```
<210> SEQ ID NO 55
<211> LENGTH: 116
<212> TYPE: PRT
<213> ORGANISM: Artificial Sequence
<220> FEATURE:
<223> OTHER INFORMATION: Synthetic amino acid - clone name: C11

<400> SEQUENCE: 55

Gln Val Gln Leu Val Gln Ser Gly Ala Ala Val Lys Pro Gly Ala
1               5                   10                  15

Ser Val Lys Val Ser Arg Lys Ala Ser Gly Tyr Thr Phe Thr Asn Asp
                20                  25                  30

Tyr Ile His Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 56
<211> LENGTH: 116
<212> TYPE: PRT
<213> ORGANISM: Artificial Sequence
<220> FEATURE:
<223> OTHER INFORMATION: Synthetic amino acid - clone name: F08

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile His Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 57
<211> LENGTH: 116
<212> TYPE: PRT
<213> ORGANISM: Artificial Sequence
<220> FEATURE:
<223> OTHER INFORMATION: Synthetic amino acid - clone name: E9

<400> SEQUENCE: 57

Gln Val Gln Leu Val Glu Ser Gly Ala Glu Val Arg Lys Pro Gly Glu
1               5                   10                  15
```

Ser Leu Gln Ile Ser Cys Lys Ala Ser Gly Tyr Arg Phe Thr Asn Tyr
            20                  25                  30

Trp Ile Gly Trp Val Arg Gln Met Pro Gly Lys Gly Leu Glu Trp Met
        35                  40                  45

Gly Ile Thr Tyr Pro Ala Asp Ser Thr Thr Val Tyr Ser Pro Ser Phe
    50                  55                  60

Gln Gly Gln Val Thr Ile Ser Ala Asp Lys Ser Ile Ser Thr Val Phe
65                  70                  75                  80

Leu Gln Trp Ser Ser Leu Arg Ser Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 58
<211> LENGTH: 116
<212> TYPE: PRT
<213> ORGANISM: Artificial Sequence
<220> FEATURE:
<223> OTHER INFORMATION: Synthetic amino acid - clone name: E11

<400> SEQUENCE: 58

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Asn Asp Gly Ser Ser Thr Ser Tyr Ala Asp Ser Val
    50                  55                  60

Lys Gly Arg Phe Thr Ile Ser Arg Asp Thr Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 59
<211> LENGTH: 116
<212> TYPE: PRT
<213> ORGANISM: Artificial Sequence
<220> FEATURE:
<223> OTHER INFORMATION: Synthetic amino acid - clone name: H11

<400> SEQUENCE: 59

Gln Val Gln Leu Leu Glu Ser Gly Ala Glu Val Lys Asn Pro Gly Ala
1               5                   10                  15

Ser Val Lys Val Ser Cys Lys Ala Ser Gly Tyr Pro Phe Ser Ala Tyr
            20                  25                  30

Tyr Ile Gln Trp Val Arg Gln Ala Pro Gly Gln Gly Leu Glu Trp Met
        35                  40                  45

Gly Trp Leu Asn Pro Asn Ser Gly Asp Thr His Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Gly Leu Thr Ser Asp Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 60
<211> LENGTH: 116
<212> TYPE: PRT
<213> ORGANISM: Artificial Sequence
<220> FEATURE:
<223> OTHER INFORMATION: Synthetic amino acid - clone name: C08

<400> SEQUENCE: 60

Glu Val Gln Leu Leu Glu Ser Gly Gly Leu Val Gln Pro Gly Gly
1               5                   10                  15

Ser Leu Arg Leu Ser Cys Thr Ala Ser Gly Phe Ser Phe Asn Ala Phe
                20                  25                  30

Trp Met His Trp Val Arg Gln Ala Pro Gly Lys Gly Leu Glu Trp Val
            35                  40                  45

Ser Arg Ile Ser Ile Asp Gly Thr Thr Thr Tyr Ala Asp Ser Val
        50                  55                  60

Gln Gly Arg Phe Thr Ile Ser Arg Asp Asn Ala Arg Asn Thr Leu Tyr
65                  70                  75                  80

Leu Gln Met Asn Ser Leu Arg Ala Glu Asp Ala Ala Val Tyr Tyr Cys
                85                  90                  95

Ala Thr His Gly Gly Asp Arg Ser Tyr Trp Ser Gln Gly Thr Leu Val
            100                 105                 110

Thr Val Ser Ser
        115

<210> SEQ ID NO 61
<211> LENGTH: 116
<212> TYPE: PRT
<213> ORGANISM: Artificial Sequence
<220> FEATURE:
<223> OTHER INFORMATION: Synthetic amino acid - clone name: XB2708

<400> SEQUENCE: 61

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Ser Arg Ser Tyr
                20                  25                  30

Gly Met His Trp Val Arg Gln Ala Pro Gly Lys Gly Leu Glu Trp Val
            35                  40                  45

Ala Phe Ile Leu Phe Asp Gly Asn Asn Lys Tyr Tyr Ala Asp Ser Val
        50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: Synthetic amino acid - clone name: D03

<400> SEQUENCE: 62

Gln Val Gln Leu Val Gln Ser Gly Gly Gly Leu Val Gln Pro Gly Gly
1               5                   10                  15

Ser Leu Arg Leu Ser Cys Val Ala Ser Gly Phe Thr Phe Gly Asn Asp
            20                  25                  30

Trp Met His Trp Val Arg Gln Ala Pro Gly Lys Gly Leu Val Trp Val
        35                  40                  45

Ser Arg Ile Asn Ala Asp Gly Thr Ser Thr Ala Tyr Ala Glu Ser Val
    50                  55                  60

Lys Gly Arg Phe Thr Val Ser Arg Asp Asn Ala Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
                100                 105                 110

Thr Val Ser Ser
        115

<210> SEQ ID NO 63
<211> LENGTH: 115
<212> TYPE: PRT
<213> ORGANISM: Artificial Sequence
<220> FEATURE:
<223> OTHER INFORMATION: Synthetic amino acid - clone name: A10

<400> SEQUENCE: 63

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Ala Pro Gly Lys Gly Leu Glu Trp Val
        35                  40                  45

Ser Leu Ile Tyr Ser Asp Gly Ser Thr Tyr Tyr Ala Asp Ser Val Lys
    50                  55                  60

Gly Arg Phe Thr Ile Ser Arg Asp Asn Ser Lys Lys Thr Leu Tyr Leu
65                  70                  75                  80

Gln Met Asn Asn Leu Arg Val Glu Asp Thr Ala Val Tyr Tyr Cys Ala
                85                  90                  95

Thr His Gly Gly Asp Arg Ser Tyr Trp Gly Gln Gly Thr Leu Val Thr
                100                 105                 110

Val Ser Ser
        115

<210> SEQ ID NO 64
<211> LENGTH: 116
<212> TYPE: PRT

<213> ORGANISM: Artificial Sequence
<220> FEATURE:
<223> OTHER INFORMATION: Synthetic amino acid - clone name: C09

<400> SEQUENCE: 64

Gln Val Gln Leu Val Gln Ser Gly Gly Ala Leu Val Gln Pro Gly Gly
1               5                   10                  15

Ser Leu Arg Leu Ser Cys Ala Ala Ser Gly Phe Thr Leu Ser Asn Asn
            20                  25                  30

Ala Met Ser Trp Val Arg Gln Ala Pro Gly Lys Arg Leu Glu Trp Val
        35                  40                  45

Ser Ala Ile Asp Gly Ser Gly Gly Thr Thr Tyr Tyr Ala Gly Ser Val
    50                  55                  60

Lys Gly Arg Phe Thr Ile Ser Ser Asp Asn Ser Lys Asn Thr Val Phe
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 65
<211> LENGTH: 116
<212> TYPE: PRT
<213> ORGANISM: Artificial Sequence
<220> FEATURE:
<223> OTHER INFORMATION: Synthetic amino acid - clone name: A06

<400> SEQUENCE: 65

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Gly His
            20                  25                  30

Trp Met His Trp Val Arg Gln Val Pro Gly Lys Gly Leu Val Trp Val
        35                  40                  45

Ser His Ile Ser Asn Asp Gly Ser Ile Thr Arg Tyr Ala Asp Ser Val
    50                  55                  60

Lys Gly Arg Phe Thr Val Ala Arg Asp Asn Ala Lys Asn Thr Met Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 66
<211> LENGTH: 116
<212> TYPE: PRT
<213> ORGANISM: Artificial Sequence
<220> FEATURE:
<223> OTHER INFORMATION: Synthetic amino acid - clone name: C05

<400> SEQUENCE: 66

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ile Phe Ser Ser Asn
            20                  25                  30

```
Trp Met His Trp Val Arg Gln Val Pro Gly Lys Gly Leu Glu Trp Val
            35                  40                  45

Ser Arg Ile Lys Thr Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 67
<211> LENGTH: 116
<212> TYPE: PRT
<213> ORGANISM: Artificial Sequence
<220> FEATURE:
<223> OTHER INFORMATION: Synthetic amino acid - clone name: H01

<400> SEQUENCE: 67

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Ser Asp
            20                  25                  30

Trp Met His Trp Val Arg Gln Ala Pro Gly Lys Gly Leu Val Trp Val
            35                  40                  45

Ser Arg Ile Ser Ser Asp Gly Ser Thr Thr Ala Tyr Ala Asp Ser Val
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 68
<211> LENGTH: 116
<212> TYPE: PRT
<213> ORGANISM: Artificial Sequence
<220> FEATURE:
<223> OTHER INFORMATION: Synthetic amino acid - clone name: G04

<400> SEQUENCE: 68

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Ser Asp
            20                  25                  30

Trp Met His Trp Val Arg Gln Ala Pro Gly Lys Gly Leu Val Trp Val
            35                  40                  45

Ser Arg Ile Ser Ser Asp Gly Ser Thr Thr Ala Tyr Ala Asp Ser Val
    50                  55                  60

Arg Gly Arg Phe Thr Ile Ser Arg Asp Asn Thr Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 69
<211> LENGTH: 116
<212> TYPE: PRT
<213> ORGANISM: Artificial Sequence
<220> FEATURE:
<223> OTHER INFORMATION: Synthetic amino acid - clone name: G07

<400> SEQUENCE: 69

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Trp Met His Trp Val Arg Gln Ala Pro Gly Glu Gly Leu Val Trp Val
        35                  40                  45

Ser Arg Ile Ser Ser Asp Gly Ser Ser Thr Ala Tyr Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Arg Ala Glu Asp Thr Ala Val Tyr Tyr Cys
                85                  90                  95

Ala Thr His Gly Gly Asp Arg Ser Tyr Trp Gly Gln Gly Thr Leu Val
            100                 105                 110

Thr Val Ser Ser
        115

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide: Ck1

<400> SEQUENCE: 70
caactgctca tcagatggcg g                                           21

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide: Cl1

<400> SEQUENCE: 71
cagtgtggcc ttgttggctt g                                           21

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide: Ck2

<400> SEQUENCE: 72
agatggtgca gccacagttc g                                           21

<210> SEQ ID NO 73
<211> LENGTH: 41
<212> TYPE: DNA
<213> ORGANISM: Artificial Sequence
<220> FEATURE:
<223> OTHER INFORMATION: Synthetic oligonucleotide: Jl1-3Ck2

<400> SEQUENCE: 73
agatggtgca gccacagttc gtagacggts ascttggtcc c           41

<210> SEQ ID NO 74
<211> LENGTH: 41
<212> TYPE: DNA
<213> ORGANISM: Artificial Sequence
<220> FEATURE:
<223> OTHER INFORMATION: Synthetic oligonucleotide: Jl7Ck2

<400> SEQUENCE: 74
agatggtgca gccacagttc ggagacggtc agctgggtgc c           41

<210> SEQ ID NO 75
<211> LENGTH: 42
<212> TYPE: DNA
<213> ORGANISM: Artificial Sequence
<220> FEATURE:
<223> OTHER INFORMATION: Synthetic oligonucleotide: T7TMVUTR

<400> SEQUENCE: 75
taatacgact cactataggg acaattacta tttacaatta ca          42

<210> SEQ ID NO 76
<211> LENGTH: 42
<212> TYPE: DNA
<213> ORGANISM: Artificial Sequence
<220> FEATURE:
<223> OTHER INFORMATION: Synthetic oligonucleotide: UTRVk1a

<400> SEQUENCE: 76
caattactat ttacaattac aatgracatc cagatgaccc ag          42

<210> SEQ ID NO 77
<211> LENGTH: 42
<212> TYPE: DNA
<213> ORGANISM: Artificial Sequence
<220> FEATURE:
<223> OTHER INFORMATION: Synthetic oligonucleotide: UTRVk1b

<400> SEQUENCE: 77
caattactat ttacaattac aatggmcatc cagttgaccc ag          42

<210> SEQ ID NO 78
<211> LENGTH: 42
<212> TYPE: DNA
<213> ORGANISM: Artificial Sequence
<220> FEATURE:
<223> OTHER INFORMATION: Synthetic oligonucleotide: UTRVk1c

<400> SEQUENCE: 78
caattactat ttacaattac aatggccatc crgatgaccc ag          42

<210> SEQ ID NO 79
<211> LENGTH: 42
<212> TYPE: DNA
<213> ORGANISM: Artificial Sequence
<220> FEATURE:

<223> OTHER INFORMATION: Synthetic oligonucleotide: UTRVk1d

<400> SEQUENCE: 79
caattactat ttacaattac aatggtcatc tggatgaccc ag                              42

<210> SEQ ID NO 80
<211> LENGTH: 42
<212> TYPE: DNA
<213> ORGANISM: Artificial Sequence
<220> FEATURE:
<223> OTHER INFORMATION: Synthetic oligonucleotide: UTRVk2a

<400> SEQUENCE: 80
caattactat ttacaattac aatggatatt gtgatgaccc ag                              42

<210> SEQ ID NO 81
<211> LENGTH: 42
<212> TYPE: DNA
<213> ORGANISM: Artificial Sequence
<220> FEATURE:
<223> OTHER INFORMATION: Synthetic oligonucleotide: UTRVk2b

<400> SEQUENCE: 81
caattactat ttacaattac aatggatrtt gtgatgactc ag                              42

<210> SEQ ID NO 82
<211> LENGTH: 42
<212> TYPE: DNA
<213> ORGANISM: Artificial Sequence
<220> FEATURE:
<223> OTHER INFORMATION: Synthetic oligonucleotide: UTRVk3a

<400> SEQUENCE: 82
caattactat ttacaattac aatggaaatt gtgttgacrc ag                              42

<210> SEQ ID NO 83
<211> LENGTH: 42
<212> TYPE: DNA
<213> ORGANISM: Artificial Sequence
<220> FEATURE:
<223> OTHER INFORMATION: Synthetic oligonucleotide: UTRVk3b

<400> SEQUENCE: 83
caattactat ttacaattac aatggaaata gtgatgacgc ag                              42

<210> SEQ ID NO 84
<211> LENGTH: 42
<212> TYPE: DNA
<213> ORGANISM: Artificial Sequence
<220> FEATURE:
<223> OTHER INFORMATION: Synthetic oligonucleotide: UTRVk3c

<400> SEQUENCE: 84
caattactat ttacaattac aatggaaatt gtaatgacac ag                              42

<210> SEQ ID NO 85
<211> LENGTH: 42
<212> TYPE: DNA
<213> ORGANISM: Artificial Sequence
<220> FEATURE:
<223> OTHER INFORMATION: Synthetic oligonucleotide: UTRVk4a

<400> SEQUENCE: 85
caattactat ttacaattac aatggacatc gtgatgaccc ag                              42

```
<210> SEQ ID NO 86
<211> LENGTH: 42
<212> TYPE: DNA
<213> ORGANISM: Artificial Sequence
<220> FEATURE:
<223> OTHER INFORMATION: Synthetic oligonucleotide: UTRVk5a

<400> SEQUENCE: 86
caattactat ttacaattac aatggaaacg acactcacgc ag                              42

<210> SEQ ID NO 87
<211> LENGTH: 42
<212> TYPE: DNA
<213> ORGANISM: Artificial Sequence
<220> FEATURE:
<223> OTHER INFORMATION: Synthetic oligonucleotide: UTRVk6a

<400> SEQUENCE: 87
caattactat ttacaattac aatggaaatt gtgctgactc ag                              42

<210> SEQ ID NO 88
<211> LENGTH: 42
<212> TYPE: DNA
<213> ORGANISM: Artificial Sequence
<220> FEATURE:
<223> OTHER INFORMATION: Synthetic oligonucleotide: UTRVk6b

<400> SEQUENCE: 88
caattactat ttacaattac aatggatgtt gtgatgacac ag                              42

<210> SEQ ID NO 89
<211> LENGTH: 42
<212> TYPE: DNA
<213> ORGANISM: Artificial Sequence
<220> FEATURE:
<223> OTHER INFORMATION: Synthetic oligonucleotide: UTRVL1a

<400> SEQUENCE: 89
caattactat ttacaattac aatgcagtct gtgctgackc ag                              42

<210> SEQ ID NO 90
<211> LENGTH: 42
<212> TYPE: DNA
<213> ORGANISM: Artificial Sequence
<220> FEATURE:
<223> OTHER INFORMATION: Synthetic oligonucleotide: UTRVL1b

<400> SEQUENCE: 90
caattactat ttacaattac aatgcagtct gtgytgacgc ag                              42

<210> SEQ ID NO 91
<211> LENGTH: 42
<212> TYPE: DNA
<213> ORGANISM: Artificial Sequence
<220> FEATURE:
<223> OTHER INFORMATION: Synthetic oligonucleotide: UTRVL2

<400> SEQUENCE: 91
caattactat ttacaattac aatgcagtct gccctgactc ag                              42

<210> SEQ ID NO 92
<211> LENGTH: 42
<212> TYPE: DNA
<213> ORGANISM: Artificial Sequence
<220> FEATURE:
<223> OTHER INFORMATION: Synthetic oligonucleotide: UTRVL3a
```

```
<400> SEQUENCE: 92
caattactat ttacaattac aatgtcctat gwgctgactc ag                              42

<210> SEQ ID NO 93
<211> LENGTH: 42
<212> TYPE: DNA
<213> ORGANISM: Artificial Sequence
<220> FEATURE:
<223> OTHER INFORMATION: Synthetic oligonucleotide: UTRVL3b

<400> SEQUENCE: 93
caattactat ttacaattac aatgtcctat gagctgacac ag                              42

<210> SEQ ID NO 94
<211> LENGTH: 42
<212> TYPE: DNA
<213> ORGANISM: Artificial Sequence
<220> FEATURE:
<223> OTHER INFORMATION: Synthetic oligonucleotide: UTRVL3c

<400> SEQUENCE: 94
caattactat ttacaattac aatgtcttct gagctgactc ag                              42

<210> SEQ ID NO 95
<211> LENGTH: 42
<212> TYPE: DNA
<213> ORGANISM: Artificial Sequence
<220> FEATURE:
<223> OTHER INFORMATION: Synthetic oligonucleotide: UTRVL3d

<400> SEQUENCE: 95
caattactat ttacaattac aatgtcctat gagctgatgc ag                              42

<210> SEQ ID NO 96
<211> LENGTH: 42
<212> TYPE: DNA
<213> ORGANISM: Artificial Sequence
<220> FEATURE:
<223> OTHER INFORMATION: Synthetic oligonucleotide: UTRVL4

<400> SEQUENCE: 96
caattactat ttacaattac aatgcagcyt gtgctgactc aa                              42

<210> SEQ ID NO 97
<211> LENGTH: 42
<212> TYPE: DNA
<213> ORGANISM: Artificial Sequence
<220> FEATURE:
<223> OTHER INFORMATION: Synthetic oligonucleotide: UTRVL5

<400> SEQUENCE: 97
caattactat ttacaattac aatgcagsct gtgctgactc ag                              42

<210> SEQ ID NO 98
<211> LENGTH: 42
<212> TYPE: DNA
<213> ORGANISM: Artificial Sequence
<220> FEATURE:
<223> OTHER INFORMATION: Synthetic oligonucleotide: UTRVL6

<400> SEQUENCE: 98
caattactat ttacaattac aatgaattt atgctgactc ag                               42

<210> SEQ ID NO 99
<211> LENGTH: 42
```

```
<210> SEQ ID NO 99
<211> LENGTH: 42
<212> TYPE: DNA
<213> ORGANISM: Artificial Sequence
<220> FEATURE:
<223> OTHER INFORMATION: Synthetic oligonucleotide: UTRVL7

<400> SEQUENCE: 99
caattactat ttacaattac aatgcagrct gtggtgactc ag                    42

<210> SEQ ID NO 100
<211> LENGTH: 42
<212> TYPE: DNA
<213> ORGANISM: Artificial Sequence
<220> FEATURE:
<223> OTHER INFORMATION: Synthetic oligonucleotide: UTRVL8

<400> SEQUENCE: 100
caattactat ttacaattac aatgcagact gtggtgaccc ag                    42

<210> SEQ ID NO 101
<211> LENGTH: 42
<212> TYPE: DNA
<213> ORGANISM: Artificial Sequence
<220> FEATURE:
<223> OTHER INFORMATION: Synthetic oligonucleotide: UTRVL4/9

<400> SEQUENCE: 101
caattactat ttacaattac aatgcwgcct gtgctgactc ag                    42

<210> SEQ ID NO 102
<211> LENGTH: 42
<212> TYPE: DNA
<213> ORGANISM: Artificial Sequence
<220> FEATURE:
<223> OTHER INFORMATION: Synthetic oligonucleotide: UTRVL10

<400> SEQUENCE: 102
caattactat ttacaattac aatgcaggca gggctgactc ag                    42

<210> SEQ ID NO 103
<211> LENGTH: 107
<212> TYPE: PRT
<213> ORGANISM: Artificial Sequence
<220> FEATURE:
<223> OTHER INFORMATION: Synthetic amino acid - clone name: B10

<400> SEQUENCE: 103
```

Gln Ser Val Leu Thr Gln Ser Pro Asp Leu Gln Ser Val Thr Pro Arg
1               5                  10                  15

Glu Lys Leu Thr Ile Thr Cys Arg Ala Ser Gln Thr Ile Gly Ser Thr
            20                  25                  30

Leu His Trp Tyr Gln Gln Lys Pro Gly Gln Ser Pro Arg Leu Val Ile
        35                  40                  45

Lys Tyr Ala Tyr Gln Ser Val Ser Gly Val Pro Ser Arg Phe Ser Gly
    50                  55                  60

Ser Gly Ser Gly Thr Glu Phe Thr Leu Thr Ile Asn Gly Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Leu Thr Val Leu
            100                 105

```
<210> SEQ ID NO 104
<211> LENGTH: 107
```

<212> TYPE: PRT
<213> ORGANISM: Artificial Sequence
<220> FEATURE:
<223> OTHER INFORMATION: Synthetic amino acid - clone name: H10

<400> SEQUENCE: 104

Gln Ser Val Leu Thr Gln Ser Pro Asp Phe Gln Ser Val Ser Pro Lys
1               5                   10                  15

Asp Lys Val Thr Ile Thr Cys Arg Ala Ser Gln Ser Ile Gly Ser Ser
            20                  25                  30

Leu His Trp Tyr Gln Gln Lys Pro Gly Gln Ser Pro Lys Leu Leu Ile
        35                  40                  45

Lys Tyr Ser Ser Gln Ser Phe Ser Gly Val Pro Ser Arg Phe Ser Gly
    50                  55                  60

Ser Ala Ser Gly Thr Glu Phe Thr Leu Thr Ile Thr Gly Leu Glu Ala
65                  70                  75                  80

Glu Asp Ala Ala Thr Tyr Tyr Cys His Gln Ser Ser Ser Leu Pro His
                85                  90                  95

Thr Phe Gly Gln Gly Thr Lys Val Thr Val Leu
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic amino acid - clone name: F10

<400> SEQUENCE: 105

Gln Ser Val Leu Thr Gln Ser Pro Glu Phe Gln Ser Val Thr Pro Lys
1               5                   10                  15

Glu Lys Val Thr Ile Thr Cys Arg Ala Ser Gln Ser Ile Gly Ser Gly
            20                  25                  30

Leu His Trp Tyr Gln Gln Lys Pro His Gln Ser Pro Lys Leu Leu Ile
        35                  40                  45

Arg Tyr Ala Ser Gln Ser Met Ser Gly Val Pro Ser Arg Phe Ser Gly
    50                  55                  60

Ser Gly Ser Gly Thr Asp Phe Thr Leu Thr Ile Ser Arg Leu Glu Val
65                  70                  75                  80

Glu Asp Ala Ala Met Tyr Tyr Cys His Gln Ser Ser Ser Leu Pro Trp
                85                  90                  95

Thr Phe Gly Gln Gly Thr Lys Val Thr Val Leu
            100                 105

<210> SEQ ID NO 106
<211> LENGTH: 107
<212> TYPE: PRT
<213> ORGANISM: Artificial Sequence
<220> FEATURE:
<223> OTHER INFORMATION: Synthetic amino acid - clone name: B12

<400> SEQUENCE: 106

Gln Ser Val Leu Thr Gln Ser Pro Asp Phe Gln Ser Val Thr Pro Lys
1               5                   10                  15

Gln Asn Val Thr Phe Thr Cys Arg Ala Ser Gln Ser Ile Gly Ile Lys
            20                  25                  30

Leu His Trp Tyr Gln Gln Lys Pro Asp Gln Ser Pro Lys Val Leu Ile
        35                  40                  45

Lys Tyr Ala Ser Gln Pro Phe Ser Gly Val Pro Ser Arg Phe Ser Gly
            50                  55                  60

Arg Gly Ser Gly Thr Asp Phe Thr Leu Thr Ile Asn Ser Leu Glu Ala
65                  70                  75                  80

Glu Asp Ala Ala Thr Tyr Tyr Cys His Gln Thr Ser Ser Leu Pro Leu
                    85                  90                  95

Thr Phe Gly Gly Gly Thr Lys Val Thr Val Leu
                100                 105

<210> SEQ ID NO 107
<211> LENGTH: 108
<212> TYPE: PRT
<213> ORGANISM: Artificial Sequence
<220> FEATURE:
<223> OTHER INFORMATION: Synthetic amino acid - clone name: B11

<400> SEQUENCE: 107

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Val Arg Val Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Leu Thr Val Leu
                100                 105

<210> SEQ ID NO 108
<211> LENGTH: 108
<212> TYPE: PRT
<213> ORGANISM: Artificial Sequence
<220> FEATURE:
<223> OTHER INFORMATION: Synthetic amino acid - clone name: E7

<400> SEQUENCE: 108

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Gln Thr Phe Gly Gln Gly Thr Lys Leu Thr Val Leu
                100                 105

<210> SEQ ID NO 109
<211> LENGTH: 109
<212> TYPE: PRT

<213> ORGANISM: Artificial Sequence
<220> FEATURE:
<223> OTHER INFORMATION: Synthetic amino acid - clone name: E8

<400> SEQUENCE: 109

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Thr Val Leu
            100                 105

<210> SEQ ID NO 110
<211> LENGTH: 108
<212> TYPE: PRT
<213> ORGANISM: Artificial Sequence
<220> FEATURE:
<223> OTHER INFORMATION: Synthetic amino acid - clone name: H8

<400> SEQUENCE: 110

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Leu Gln Lys Pro Gly Gln Ala Pro Arg Leu Leu
        35                  40                  45

Ile Ser Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Pro
                85                  90                  95

Phe Thr Phe Gly Pro Gly Thr Lys Leu Thr Val Leu
            100                 105

<210> SEQ ID NO 111
<211> LENGTH: 108
<212> TYPE: PRT
<213> ORGANISM: Artificial Sequence
<220> FEATURE:
<223> OTHER INFORMATION: Synthetic amino acid - clone name: H12

<400> SEQUENCE: 111

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Val Ala Trp Tyr Gln Gln Lys Pro Gly Gln Ala Pro Arg Leu Leu
        35                  40                  45

Ile Ser Gly Ala Ser Arg Arg Ala Thr Gly Ile Pro Asp Arg Phe Thr
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr His Cys Gln Gln Phe Gly Ser Ser Pro
                85                  90                  95

Trp Thr Phe Gly Gln Gly Thr Lys Leu Thr Val Leu
            100                 105

<210> SEQ ID NO 112
<211> LENGTH: 108
<212> TYPE: PRT
<213> ORGANISM: Artificial Sequence
<220> FEATURE:
<223> OTHER INFORMATION: Synthetic amino acid - clone name: F8

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Arg Ser Asn Ile Gly Gly Asn
            20                  25                  30

Ala Val Asn Trp Tyr Gln Gln Lys Pro Gly Gln Ala Pro Arg Leu Leu
            35                  40                  45

Ile His Val Ala Ser Arg Arg Val Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Ile Tyr Tyr Cys Gln Gln Tyr Gly Ser Ser Pro
                85                  90                  95

Leu Thr Phe Gly Gly Gly Thr Lys Leu Thr Val Leu
            100                 105

<210> SEQ ID NO 113
<211> LENGTH: 108
<212> TYPE: PRT
<213> ORGANISM: Artificial Sequence
<220> FEATURE:
<223> OTHER INFORMATION: Synthetic amino acid - clone name: D11

<400> SEQUENCE: 113

Gln Ser Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Thr Ser Asn
            20                  25                  30

Phe Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Ile Ser
        50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Gly Ala Ser Pro
                85                  90                  95

Arg Thr Phe Gly Gln Gly Thr Gln Leu Thr Val Leu
            100                 105

<210> SEQ ID NO 114
<211> LENGTH: 108
<212> TYPE: PRT
<213> ORGANISM: Artificial Sequence
<220> FEATURE:
<223> OTHER INFORMATION: Synthetic amino acid - clone name: G8

<400> SEQUENCE: 114

Gln Ser Val Leu Thr Gln Ser Pro Gly Thr Leu Ser Leu Ser Pro Gly
1               5                   10                  15

Asp Arg Ala Thr Leu Ser Cys Arg Ala Ser Gln Ser Leu Ser Gly Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Ala Gly Ile Pro Lys Arg Phe Ser
50                  55                  60

Gly Ser Gly Ser Arg Thr Asp Phe Thr Leu Thr Ile Ser Arg Val Asp
65                  70                  75                  80

Pro Ala Asp Ser Ala Val Tyr Tyr Cys Gln Gln Tyr Gly Ser Ala Leu
                85                  90                  95

Leu Thr Phe Gly Gly Gly Thr Lys Val Thr Val Leu
            100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic amino acid - clone name: H9

<400> SEQUENCE: 115

Gln Ser Val Leu Thr Gln Ser Pro Gly Thr Leu Ser Leu Ser Pro Gly
1               5                   10                  15

Glu Ser Ala Thr Leu Ser Cys Arg Ala Ser Glu Asp Ile Tyr Asn Asn
            20                  25                  30

Tyr Leu Ala Trp Tyr Gln His Lys Arg Gly Gln Pro Pro Arg Leu Leu
        35                  40                  45

Ile Phe Arg Ala Ser Thr Arg Ala Thr Gly Ile Pro Thr Arg Phe Ser
50                  55                  60

Gly Ser Gly Ser Gly Arg Asp Phe Val Leu Thr Ile Asn Arg Leu Glu
65                  70                  75                  80

Pro Glu Asp Phe Ala Val Tyr Tyr Cys Gln Gln Tyr Gly Asn Ser Trp
                85                  90                  95

Thr Phe Gly Gln Gly Thr Lys Leu Thr Val Leu
            100                 105

<210> SEQ ID NO 116
<211> LENGTH: 107
<212> TYPE: PRT
<213> ORGANISM: Artificial Sequence
<220> FEATURE:
<223> OTHER INFORMATION: Synthetic amino acid - clone name: H11

<400> SEQUENCE: 116

Gln Ser Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Thr Phe Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Arg Asn Leu Pro Phe
                85                  90                  95

Thr Phe Gly Pro Gly Thr Lys Leu Thr Val Leu
            100                 105

<210> SEQ ID NO 117
<211> LENGTH: 107
<212> TYPE: PRT
<213> ORGANISM: Artificial Sequence
<220> FEATURE:
<223> OTHER INFORMATION: Synthetic amino acid - clone name: G12

<400> SEQUENCE: 117

Gln Ser Val Leu Thr Gln Ser Pro Asp Phe Gln Ser Val Thr Pro Lys
1               5                   10                  15

Glu Glu Val Thr Ile Thr Cys Arg Ala Ser Glu Ser Ile Gly Thr Ala
            20                  25                  30

Leu His Trp Tyr Gln Gln Lys Pro Asp Gln Ser Pro Lys Leu Leu Ile
        35                  40                  45

Lys Tyr Ser Ser Gln Ser Ile Ser Gly Val Pro Ser Arg Phe Val Gly
    50                  55                  60

Arg Gly Ser Glu Thr Glu Phe Thr Leu Thr Ile Asn Ser Leu Glu Ala
65                  70                  75                  80

Glu Asn Ala Ala Thr Tyr Tyr Cys His Gln Ser Arg Ser Phe Pro Leu
                85                  90                  95

Thr Phe Gly Gln Gly Thr Gln Leu Thr Val Leu
            100                 105

<210> SEQ ID NO 118
<211> LENGTH: 107
<212> TYPE: PRT
<213> ORGANISM: Artificial Sequence
<220> FEATURE:
<223> OTHER INFORMATION: Synthetic amino acid - clone name: E11

<400> SEQUENCE: 118

Gln Ser Val Leu Thr Gln Ser Pro Gly Thr Leu Ser Leu Ser Pro Gly
1               5                   10                  15

Glu Arg Ala Thr Leu Ser Cys Arg Thr Ser Gln Ile Leu His Ser Gln
            20                  25                  30

Tyr Leu Ala Trp Tyr Gln Gln Lys Arg Gly Gln Ala Pro Arg Leu Leu
        35                  40                  45

Ile Phe Arg Ala Ser Thr Arg Ala Thr Gly Ile Pro Glu Arg Phe Ser
    50                  55                  60

Gly Ser Gly Ser Gly Arg Asp Phe Val Leu Thr Ile Ser Arg Leu Glu
65                  70                  75                  80

Pro Glu Asp Ser Ala Val Tyr Tyr Cys Gln Gln Tyr Glu Thr Ser Trp
                85                  90                  95

Thr Phe Gly Gln Gly Thr Lys Val Thr Val Leu
            100                 105

<210> SEQ ID NO 119
<211> LENGTH: 107
<212> TYPE: PRT
<213> ORGANISM: Artificial Sequence
<220> FEATURE:
<223> OTHER INFORMATION: Synthetic amino acid - clone name: F12

<400> SEQUENCE: 119

Gln Ser Val Leu Thr Gln Asp Pro Val Ser Val Ala Leu Gly Gln
1               5                   10                  15

Thr Val Arg Ile Thr Cys Gln Gly Asp Thr Leu Arg Thr Cys Tyr Ala
                20                  25                  30

Ser Trp Tyr Gln Gln Arg Pro Arg Gln Ala Pro Ile Leu Val Ile Tyr
            35                  40                  45

Gly Glu Asn Asn Arg Pro Ser Gly Ile Pro Ala Arg Phe Ser Gly Ser
50                  55                  60

Ser Ser Gly Ser Thr Ala Ser Leu Thr Ile Thr Gly Ala Gln Ala Glu
65                  70                  75                  80

Asp Glu Gly Asp Tyr Tyr Cys His Cys Arg Asp Gly Leu Asn His Leu
                85                  90                  95

Val Phe Gly Gly Gly Thr Lys Val Thr Val Leu
                100                 105

<210> SEQ ID NO 120
<211> LENGTH: 110
<212> TYPE: PRT
<213> ORGANISM: Artificial Sequence
<220> FEATURE:
<223> OTHER INFORMATION: Synthetic amino acid - clone name: C8

<400> SEQUENCE: 120

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Lys Asn
                20                  25                  30

Phe Val Ser Trp Tyr Gln His Leu Pro Gly Thr Ala Pro Lys Leu Leu
            35                  40                  45

Ile Tyr Asp Asn Tyr Gln Arg Phe Ser Gly Ile Pro Asp Arg Phe Ser
50                  55                  60

Gly Phe Lys Ser Gly Thr Ser Ala Thr Leu Ser Ile Thr Gly Leu Gln
65                  70                  75                  80

Thr Ala Asp Glu Ala Asp Tyr Tyr Cys Gly Thr Trp Asp Ser Ser Leu
                85                  90                  95

Ser Val Val Ile Phe Gly Gly Gly Thr Lys Leu Thr Val Leu
                100                 105                 110

<210> SEQ ID NO 121
<211> LENGTH: 107
<212> TYPE: PRT
<213> ORGANISM: Artificial Sequence
<220> FEATURE:
<223> OTHER INFORMATION: Synthetic amino acid - clone name: A8

<400> SEQUENCE: 121

Gln Ala Gly Leu Thr Gln Ser Pro Asp Phe Gln Ser Val Thr Pro Lys
1               5                   10                  15

Glu Arg Val Thr Ile Thr Cys Arg Ala Ser Arg Tyr Ile Gly Ser Asn
                20                  25                  30

Leu His Trp Tyr Gln Gln Lys Pro Asp Gln Pro Pro Lys Leu Leu Ile
            35                  40                  45

Lys Leu Ala Ser Gln Ser Phe Ser Gly Val Pro Pro Arg Phe Ser Gly
50                  55                  60

Gly Gly Ser Gly Thr Asp Phe Thr Leu Thr Ile Asn Gly Leu Glu Ala
65                  70                  75                  80

Glu Asp Ala Ala Thr Tyr Tyr Cys His Gln Thr Gly Ser Phe Pro Tyr
                85                  90                  95

Thr Phe Gly Gln Gly Thr Lys Leu Thr Val Leu
            100                 105

<210> SEQ ID NO 122
<211> LENGTH: 110
<212> TYPE: PRT
<213> ORGANISM: Artificial Sequence
<220> FEATURE:
<223> OTHER INFORMATION: Synthetic amino acid - clone name: B8

<400> SEQUENCE: 122

Gln Ala Val Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Ser Pro Phe Trp Phe Gln Gln Arg Pro Gly Gln Ala Pro Arg Thr
        35                  40                  45

Leu Ile Tyr Asp Thr Ser Asn Lys Gln Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Pro Arg Val Val Phe Gly Gly Gly Thr Lys Val Thr Val Leu
            100                 105                 110

<210> SEQ ID NO 123
<211> LENGTH: 113
<212> TYPE: PRT
<213> ORGANISM: Artificial Sequence
<220> FEATURE:
<223> OTHER INFORMATION: Synthetic amino acid - clone name: F7
<220> FEATURE:
<221> NAME/KEY: misc_feature
<222> LOCATION: (27)..(27)
<223> OTHER INFORMATION: Xaa can be any naturally occurring amino acid

<400> SEQUENCE: 123

Gln Ala Val Val Thr Gln Ser Pro Asp Ser Leu Ala Val Ser Leu Gly
1               5                   10                  15

Glu Arg Ala Thr Ile Ser Cys Lys Ser Ser Xaa Ser Leu Leu Tyr Arg
            20                  25                  30

Ser Asn Asn Lys Asn Tyr Leu Ala Trp Tyr Gln Gln Lys Pro Gly Gln
        35                  40                  45

Pro Pro Arg Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Val Ser Arg Leu Arg Ala Glu Asp Ala Ala Val Tyr Tyr Cys Gln Gln
                85                  90                  95

Ser Tyr Arg Thr Pro Phe Ser Phe Gly Pro Gly Thr Lys Val Thr Val
            100                 105                 110

Leu

<210> SEQ ID NO 124
<211> LENGTH: 106
<212> TYPE: PRT

<213> ORGANISM: Artificial Sequence
<220> FEATURE:
<223> OTHER INFORMATION: Synthetic amino acid - clone name: B7

<400> SEQUENCE: 124

Ser Tyr Val Leu Thr Gln Pro Leu Ser Val Ser Val Ala Leu Gly Gln
1               5                   10                  15

Thr Ala Arg Ile Ser Cys Gly Gly Ala Asn Ile Ala Asn Lys Asn Val
            20                  25                  30

His Trp Tyr Gln Leu Gln Pro Gly Gln Ala Pro Val Leu Val Ile Tyr
        35                  40                  45

Arg Asp Ser Asn Arg Pro Ser Gly Ile Pro Glu Arg Phe Ser Gly Ser
50                  55                  60

Asn Ser Gly Asn Thr Ala Thr Leu Thr Ile Thr Arg Ala Gln Ala Arg
65                  70                  75                  80

Asp Glu Ala Asp Tyr Tyr Cys Gln Val Trp Asp Ser Ser Val Ile
                85                  90                  95

Ile Gly Gly Gly Thr Lys Val Thr Val Leu
            100                 105

<210> SEQ ID NO 125
<211> LENGTH: 108
<212> TYPE: PRT
<213> ORGANISM: Artificial Sequence
<220> FEATURE:
<223> OTHER INFORMATION: Synthetic amino acid - clone name: G9

<400> SEQUENCE: 125

Ser Tyr Val Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Arg Gln Lys Pro Gly Gln Ala Pro Val Leu Val Phe Tyr
        35                  40                  45

Gly Lys Asp Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Ser Ser Ala Met Arg
                85                  90                  95

Trp Val Phe Gly Gly Gly Thr Lys Leu Thr Val Leu
            100                 105

<210> SEQ ID NO 126
<211> LENGTH: 108
<212> TYPE: PRT
<213> ORGANISM: Artificial Sequence
<220> FEATURE:
<223> OTHER INFORMATION: Synthetic amino acid - clone name: A9

<400> SEQUENCE: 126

Asn Phe Met Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Val Pro Arg Thr
        35                  40                  45

Phe Ile Tyr Asp Thr His Asn Arg His Ser Trp Thr Pro Val Arg Phe
50                  55                  60

```
Ser Gly Ser Leu Phe Gly Gly Lys Ala Ala Leu Thr Leu Ser Gly Ala
 65                  70                  75                  80

Gln Pro Glu Asp Glu Ala Glu Tyr Tyr Cys Leu Leu Tyr Phe Asn Pro
                 85                  90                  95

Thr Arg Val Phe Gly Gly Gly Thr Lys Leu Thr Val
            100                 105
```

<210> SEQ ID NO 127
<211> LENGTH: 110
<212> TYPE: PRT
<213> ORGANISM: Artificial Sequence
<220> FEATURE:
<223> OTHER INFORMATION: Synthetic amino acid - clone name: A11

<400> SEQUENCE: 127

```
Asn Phe Met Leu Thr Gln Pro Pro Ser Ala Ser Ala Ser Leu Gly Ala
 1               5                  10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
             35                  40                  45

Arg Val Gly Thr Gly Gly Ile Val Gly Ser Lys Gly Asp Gly Ile Pro
 50                  55                  60

Asp Arg Phe Ser Val Leu Gly Ser Gly Leu Asn Arg Tyr Leu Thr Ile
 65                  70                  75                  80

Lys Asn Ile Gln Glu Glu Asp Glu Ser Asp Tyr His Cys Gly Ala Asp
                 85                  90                  95

His Gly Arg Val Phe Gly Gly Gly Thr Lys Leu Thr Val Leu
            100                 105                 110
```

<210> SEQ ID NO 128
<211> LENGTH: 105
<212> TYPE: PRT
<213> ORGANISM: Artificial Sequence
<220> FEATURE:
<223> OTHER INFORMATION: Synthetic amino acid - clone name: E12

<400> SEQUENCE: 128

```
Gln Pro Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                20                  25                  30

His Trp Tyr His Leu Arg Pro Gly Gln Ala Pro Val Leu Val Ile Tyr
             35                  40                  45

Phe Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp His Ser Gly Val Ile Phe
                 85                  90                  95

Gly Gly Gly Thr Lys Leu Thr Val Leu
            100                 105
```

<210> SEQ ID NO 129
<211> LENGTH: 106
<212> TYPE: PRT
<213> ORGANISM: Artificial Sequence
<220> FEATURE:
<223> OTHER INFORMATION: Synthetic amino acid - clone name: H7

<400> SEQUENCE: 129

Gln Pro Val Leu Thr Gln Ser Leu Asp Phe Gln Ser Val Thr Pro Lys
1               5                   10                  15

Glu Lys Val Thr Ile Thr Cys Arg Ala Ser Gln Asn Ile Gly Asn Ser
            20                  25                  30

Leu His Trp Tyr Gln Gln Lys Pro Asn Gln Ser Pro Lys Val Leu Ile
        35                  40                  45

Lys Tyr Ala Ser Gln Ser Phe Ser Gly Val Pro Ser Arg Phe Ser Gly
    50                  55                  60

Ser Gly Phe Gly Thr Asp Phe Thr Leu Thr Ile Asn Ser Leu Glu Pro
65                  70                  75                  80

Glu Asp Ala Ala Thr Tyr Tyr Cys His Gln Ser Arg Ser Ser His Thr
                85                  90                  95

Phe Gly Gln Gly Thr Lys Leu Thr Val Leu
            100                 105

<210> SEQ ID NO 130
<211> LENGTH: 113
<212> TYPE: PRT
<213> ORGANISM: Artificial Sequence
<220> FEATURE:
<223> OTHER INFORMATION: Synthetic amino acid - clone name: A10

<400> SEQUENCE: 130

Glu Ile Val Leu Thr Gln Ser Pro Gly Asn Leu Ser Leu Ser Pro Gly
1               5                   10                  15

Glu Arg Ala Thr Leu Ser Cys Thr Arg Cys Thr Gly Asn Ile Ala Ser
            20                  25                  30

His Phe Val Gln Trp Tyr Gln Gln Arg Pro Gly Ser Ser Pro Thr Thr
        35                  40                  45

Val Ile Phe Gly Asn Asn Gln Arg Pro Ser Gly Val Ser Asp Arg Phe
    50                  55                  60

Ser Gly Ser Ile Asp Ser Ser Asn Ser Ala Ser Leu Thr Ile Ser
65                  70                  75                  80

Arg Leu Lys Thr Glu Asp Glu Ala Asp Tyr Tyr Cys Gln Ser Phe Asp
                85                  90                  95

Val Tyr Ser His Glu Val Val Phe Gly Gly Gly Thr Lys Leu Thr Val
            100                 105                 110

Leu

<210> SEQ ID NO 131
<211> LENGTH: 113
<212> TYPE: PRT
<213> ORGANISM: Artificial Sequence
<220> FEATURE:
<223> OTHER INFORMATION: Synthetic amino acid - clone name: C11

<400> SEQUENCE: 131

Gln Thr Val Val Thr Gln Thr Pro Val Ser Leu Ser Val Thr Pro Gly
1               5                   10                  15

Gln Pro Ala Ser Ile Ser Cys Lys Ser Ser Gln Ser Leu Leu Asn Ser
            20                  25                  30

Asp Asp Gly Lys Thr Tyr Leu Tyr Trp Tyr Leu Gln Arg Pro Gly Gln
        35                  40                  45

Pro Pro His Leu Leu Ile Tyr Glu Val Ser Lys Arg Phe Ser Gly Val
    50                  55                  60

-continued

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Phe Tyr Cys Met Gln
                85                  90                  95

Ser Thr His Phe Pro Phe Thr Phe Gly Pro Gly Thr Lys Val Thr Val
            100                 105                 110

Leu

<210> SEQ ID NO 132
<211> LENGTH: 107
<212> TYPE: PRT
<213> ORGANISM: Artificial Sequence
<220> FEATURE:
<223> OTHER INFORMATION: Synthetic amino acid - clone name: D10

<400> SEQUENCE: 132

Asn Ile Gln Met Thr Gln Ser Pro Val Ser Leu Ser Ala Ser Leu Gly
1               5                   10                  15

Asp Thr Val Ser Ile Thr Cys Gln Ala Ser His Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser His Leu Glu Ala Gly Val Pro Ser Arg Phe Arg Gly
        50                  55                  60

Ser Gly Ser Gly Thr Asp Phe Thr Leu Thr Ile Asn Arg Leu Glu Pro
65                  70                  75                  80

Glu Asp Phe Ala Val Tyr Tyr Cys Gln Gln Tyr Asp Ser Pro Pro Trp
                85                  90                  95

Thr Phe Gly Gln Gly Thr Lys Leu Thr Val Leu
            100                 105

<210> SEQ ID NO 133
<211> LENGTH: 108
<212> TYPE: PRT
<213> ORGANISM: Artificial Sequence
<220> FEATURE:
<223> OTHER INFORMATION: Synthetic amino acid - clone name: D12

<400> SEQUENCE: 133

Asp Val Val Leu Thr Gln Ser Pro Gly Thr Met Ser Leu Ser Pro Gly
1               5                   10                  15

Glu Arg Ala Thr Leu Ser Cys Arg Ala Ser Gln Ser Val Ser Arg Thr
                20                  25                  30

Tyr Leu Ala Trp His Gln Gln Lys Pro Gly Gln Ala Pro Arg Leu Leu
            35                  40                  45

Ile Tyr Gly Ala Ser Ser Arg Ala Ala Gly Ile Pro Asp Arg Phe Ser
        50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Tyr Cys Gln Gln His Asp Thr Ser Gln
                85                  90                  95

Trp Thr Phe Gly Gln Gly Thr Lys Leu Thr Val Leu
            100                 105

<210> SEQ ID NO 134
<211> LENGTH: 112
<212> TYPE: PRT
<213> ORGANISM: Artificial Sequence
<220> FEATURE:

<223> OTHER INFORMATION: Synthetic amino acid - clone name: C7

<400> SEQUENCE: 134

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr His Leu Phe Trp Tyr Leu Gln Arg Pro Gly Gln Ser
        35                  40                  45

Pro Gln Leu Leu Ile Tyr Glu Val Ser Gly Arg Phe Ser Gly Val Ser
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Ile Pro His Thr Phe Gly Gln Gly Thr Lys Val Glu Ile Lys
            100                 105                 110
```

<210> SEQ ID NO 135
<211> LENGTH: 111
<212> TYPE: PRT
<213> ORGANISM: Artificial Sequence
<220> FEATURE:
<223> OTHER INFORMATION: Synthetic amino acid - clone name: D7

<400> SEQUENCE: 135

```
Asp Ile Val Met Thr Gln Ser Pro Leu Ser Leu Pro Val Thr Leu Gly
1               5                   10                  15

Gln Pro Ala Ser Ile Ser Cys Arg Ser Ser His Ser Leu Val His Ser
            20                  25                  30

Asp Gly Asn Ile Tyr Leu Asn Trp Tyr His Gln Arg Pro Gly Gln Ser
        35                  40                  45

Pro Arg Arg Leu Ile Tyr Ser Val Ser Lys Arg Asp Ser Gly Val Pro
    50                  55                  60

Asp Arg Phe Ser Gly Ser Gly Ser Arg Thr Asp Phe Thr Leu Lys Ile
65                  70                  75                  80

Ser Arg Val Glu Ala Glu Asp Val Gly Val Tyr Phe Cys Met Gln Ser
                85                  90                  95

Thr His Gln Trp Thr Phe Gly Gln Gly Thr Lys Val Glu Ile Lys
            100                 105                 110
```

<210> SEQ ID NO 136
<211> LENGTH: 107
<212> TYPE: PRT
<213> ORGANISM: Artificial Sequence
<220> FEATURE:
<223> OTHER INFORMATION: Synthetic amino acid - clone name: C9
<220> FEATURE:
<221> NAME/KEY: misc_feature
<222> LOCATION: (75)..(75)
<223> OTHER INFORMATION: Xaa can be any naturally occurring amino acid

<400> SEQUENCE: 136

```
Val Ile Trp Met Thr Gln Ser Pro Ser Thr Val Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45
```

```
Tyr Glu Ala Ser Arg Leu Glu Ser Gly Ile Pro Ser Arg Phe Ser Gly
        50                  55                  60

Ser Gly Ser Gly Thr Glu Phe Thr Leu Thr Xaa Ser Ser Leu Gln Pro
65                  70                  75                  80

Asp Asp Phe Ala Thr Tyr Tyr Cys Gln Gln Tyr Asp Ser Tyr Ser Arg
                85                  90                  95

Thr Phe Gly Gln Gly Thr Lys Val Ala Ile Lys
                100                 105
```

<210> SEQ ID NO 137
<211> LENGTH: 106
<212> TYPE: PRT
<213> ORGANISM: Artificial Sequence
<220> FEATURE:
<223> OTHER INFORMATION: Synthetic amino acid - clone name: C12

<400> SEQUENCE: 137

```
Asp Val Val Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Tyr
                20                  25                  30

Leu Ser Trp Tyr Gln Gln Lys Pro Ala Lys Ala Pro Lys Leu Leu Ile
            35                  40                  45

His Gly Ala Ser Gly Leu Gln Ser Gly Val Pro Ser Arg Phe Ser Gly
        50                  55                  60

Ser Gly Ser Gly Thr Asn Phe Thr Leu Thr Ile Ser Ser Leu Gln Pro
65                  70                  75                  80

Glu Asp Phe Ala Thr Tyr Tyr Cys Gln Gln Ser Phe Ser Met Arg Thr
                85                  90                  95

Phe Gly Gln Gly Thr Lys Val Glu Ile Lys
                100                 105
```

<210> SEQ ID NO 138
<211> LENGTH: 114
<212> TYPE: PRT
<213> ORGANISM: Artificial Sequence
<220> FEATURE:
<223> OTHER INFORMATION: Synthetic amino acid - clone name: D8

<400> SEQUENCE: 138

```
Glu Ile Val Met Thr Gln Ser Pro Gly Thr Leu Thr Leu Ser Pro Gly
1               5                   10                  15

Glu Gly Ala Thr Leu Ser Cys Arg Ala Ser Gln Ser Val Thr Ser Asn
                20                  25                  30

Tyr Leu Ala Trp Tyr Gln Gln Arg Pro Gly Ala Ser Ser Leu Gln Ser
            35                  40                  45

Gly Gln Ala Pro Arg Leu Leu Ile Tyr Asp Ala Ser Asn Arg Ala Thr
        50                  55                  60

Gly Ile Pro Asp Arg Phe Ser Gly Ser Gly Phe Gly Thr Asp Phe Thr
65                  70                  75                  80

Leu Thr Ile Ser Arg Leu Glu Pro Glu Asp Phe Ala Val Tyr Tyr Cys
                85                  90                  95

Gln Gln Tyr Val Asn Ser Arg Thr Phe Gly Gly Gly Thr Lys Val Glu
                100                 105                 110

Ile Lys
```

<210> SEQ ID NO 139
<211> LENGTH: 106

```
<212> TYPE: PRT
<213> ORGANISM: Artificial Sequence
<220> FEATURE:
<223> OTHER INFORMATION: Synthetic amino acid - clone name: D9

<400> SEQUENCE: 139
```

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Ser Val Ser Ser Lys
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asp Phe Phe Thr
                85                  90                  95

Phe Gly Pro Gly Thr Lys Val Asp Ile Lys
            100                 105

```
<210> SEQ ID NO 140
<211> LENGTH: 111
<212> TYPE: PRT
<213> ORGANISM: Artificial Sequence
<220> FEATURE:
<223> OTHER INFORMATION: Synthetic amino acid - clone name: G7

<400> SEQUENCE: 140
```

Glu Ile Val Leu Thr Gln Thr Pro Leu Ser Pro Val Thr Leu Gly
1               5                   10                  15

Gln Pro Ala Ser Ile Ser Cys Arg Ser Ser Glu Ser Pro Val His Ser
            20                  25                  30

Asp Gly Asn Ile Tyr Leu Ser Trp Leu His Gln Arg Pro Gly Gln Pro
        35                  40                  45

Pro Arg Leu Leu Leu Tyr Lys Ile Ser Asn Arg Met Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Ser Phe Gly Gln Gly Thr Lys Leu Glu Ile Lys
            100                 105                 110

```
<210> SEQ ID NO 141
<211> LENGTH: 108
<212> TYPE: PRT
<213> ORGANISM: Artificial Sequence
<220> FEATURE:
<223> OTHER INFORMATION: Synthetic amino acid - clone name: G11

<400> SEQUENCE: 141
```

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Arg
            20                  25                  30

Asn Leu Ala Trp Tyr Gln Gln Lys Pro Gly Gln Ala Pro Arg Leu Leu
        35                  40                  45

Ile Tyr Gly Gly Ser Ile Arg Ala Ser Gly Thr Ser Thr Arg Phe Ser
        50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Asp Ser Val
                85                  90                  95

Phe Thr Phe Gly Pro Gly Thr Lys Val Asp Ile Lys
            100                 105

<210> SEQ ID NO 142
<211> LENGTH: 107
<212> TYPE: PRT
<213> ORGANISM: Artificial Sequence
<220> FEATURE:
<223> OTHER INFORMATION: Synthetic amino acid - clone name: F9

<400> SEQUENCE: 142

Asn Ile Gln Met Thr Gln Ser Pro Ser Ser Leu Ser Ala Ser Val Gly
1               5                   10                  15

Asp Arg Val Asn Ile Thr Cys Arg Ala Ser Asp Asn Ile Gly Asn Tyr
            20                  25                  30

Leu Asn Trp Tyr Gln His Lys Pro Gly Lys Ala Pro Thr Val Leu Ile
        35                  40                  45

Tyr Ala Ala Ser Thr Leu His Tyr Gly Val Pro Ser Arg Phe Ser Gly
    50                  55                  60

Arg Gly Ser Gly Thr Asp Phe Thr Val Thr Ile Ser Ser Leu Gln Pro
65                  70                  75                  80

Glu Asp Ser Ala Thr Tyr Tyr Cys Gln Gln Ser Tyr Ser Thr Pro Arg
                85                  90                  95

Thr Phe Gly Gln Gly Thr Arg Val Glu Leu Lys
            100                 105

<210> SEQ ID NO 143
<211> LENGTH: 108
<212> TYPE: PRT
<213> ORGANISM: Artificial Sequence
<220> FEATURE:
<223> OTHER INFORMATION: Synthetic amino acid - clone name: E9

<400> SEQUENCE: 143

Ala Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Asn Tyr
            20                  25                  30

Leu Asn Trp Tyr Gln Gln Lys Pro Gly Lys Ala Pro Lys Leu Leu Leu
        35                  40                  45

Ser Ala Ala Ser Arg Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Leu Ala Thr Tyr Tyr Cys Gln Glu Ser Tyr Ser Thr Leu Leu
                85                  90                  95

Tyr Thr Phe Gly Gln Gly Thr Lys Leu Glu Ile Lys
            100                 105

<210> SEQ ID NO 144
<211> LENGTH: 108
<212> TYPE: PRT

```
<213> ORGANISM: Artificial Sequence
<220> FEATURE:
<223> OTHER INFORMATION: Synthetic amino acid - clone name: B1

<400> SEQUENCE: 144

Ser Tyr Glu Leu Thr Gln Pro Pro Ser Val Ser Val Ala Pro Gly Lys
1               5                   10                  15

Thr Ala Ser Ile Thr Cys Gly Gly Asn Asn Ile Gly Tyr Asp Ser Val
            20                  25                  30

His Trp Tyr Gln Gln Lys Pro Gly Gln Ala Pro Val Leu Val Val Phe
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Ser Gly Ser Glu His
                85                  90                  95

Tyr Val Phe Gly Thr Gly Thr Gln Leu Thr Val Leu
            100                 105

<210> SEQ ID NO 145
<211> LENGTH: 108
<212> TYPE: PRT
<213> ORGANISM: Artificial Sequence
<220> FEATURE:
<223> OTHER INFORMATION: Synthetic amino acid - clone name: E6

<400> SEQUENCE: 145

Leu Pro Val Leu Thr Gln Pro Pro Ser Val Ser Val Ala Pro Gly Gln
1               5                   10                  15

Thr Ala Arg Ile Ser Cys Gly Gly Asn Asn Ile Gly Ala Thr Thr Val
            20                  25                  30

His Trp Tyr Gln His Arg Pro Gly Gln Ala Pro Val Ser Val Ile Phe
        35                  40                  45

Tyr Asp Asn Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Glu Ser Thr Ser Asp His
                85                  90                  95

Pro Thr Phe Gly Gly Gly Thr Gln Leu Thr Val Leu
            100                 105

<210> SEQ ID NO 146
<211> LENGTH: 108
<212> TYPE: PRT
<213> ORGANISM: Artificial Sequence
<220> FEATURE:
<223> OTHER INFORMATION: Synthetic amino acid - clone name: F3

<400> SEQUENCE: 146

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Trp Val Phe Gly Gly Gly Thr Lys Leu Thr Val Leu
            100                 105

<210> SEQ ID NO 147
<211> LENGTH: 109
<212> TYPE: PRT
<213> ORGANISM: Artificial Sequence
<220> FEATURE:
<223> OTHER INFORMATION: Synthetic amino acid - clone name: H4

<400> SEQUENCE: 147

Ser Tyr Glu Leu Thr Gln Ser Pro Ser Val Ser Val Pro Pro Gly Gln
 1               5                  10                  15

Thr Ala Arg Ile Thr Cys Gly Gly Asn Asn Ile Val Ser Lys Gly Val
                20                  25                  30

His Trp Tyr Gln Gln Arg Pro Gly Gln Ala Pro Val Leu Val Val Tyr
             35                  40                  45

Asp Asp Ser Asp Arg Pro Ser Gly Ile Pro Glu Arg Phe Ala Gly Phe
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Gly His
                 85                  90                  95

Arg Gly Val Phe Gly Gly Gly Thr Lys Val Thr Val Leu
            100                 105

<210> SEQ ID NO 148
<211> LENGTH: 108
<212> TYPE: PRT
<213> ORGANISM: Artificial Sequence
<220> FEATURE:
<223> OTHER INFORMATION: Synthetic amino acid - clone name: H5

<400> SEQUENCE: 148

Ser Tyr Glu Leu Thr Gln Pro Pro Ser Val Ser Met Ala Pro Gly Lys
 1               5                  10                  15

Thr Ala Arg Ile Thr Cys Gly Gly Asn Asn Leu Gly Ser Lys Ile Val
                20                  25                  30

His Trp Tyr Gln Gln Lys Pro Gly Gln Ala Pro Val Val Ile Tyr
             35                  40                  45

Ser Asp Arg Asp Arg Pro Ser Gly Val Pro Glu Arg Phe Ser Gly Ser
 50                  55                  60

Asn Ser Gly Asn Ser Ala Thr Leu Thr Ile Ser Gly Val Glu Ala Gly
 65                  70                  75                  80

Asp Glu Ala Asp Tyr Tyr Cys Gln Val Trp Asp Ser Ala Thr Asp His
                 85                  90                  95

Val Val Phe Gly Gly Gly Thr Lys Leu Thr Val Leu
            100                 105

<210> SEQ ID NO 149
<211> LENGTH: 108
<212> TYPE: PRT
<213> ORGANISM: Artificial Sequence
<220> FEATURE:
<223> OTHER INFORMATION: Synthetic amino acid - clone name: B5
```

<400> SEQUENCE: 149

Ser Tyr Glu Leu Thr Gln Pro Pro Ser Val Ser Val Ala Pro Gly Gln
1               5                   10                  15

Thr Ala Thr Ile Thr Cys Ala Gly Asn Asn Ile Gly Gly Lys Ser Val
            20                  25                  30

Gln Trp Tyr Gln Gln Lys Pro Gly Gln Ala Pro Val Val Val Val Tyr
        35                  40                  45

Asp Asp Tyr Gly Arg Pro Ser Gly Ile Pro Glu Arg Val Ser Gly Ser
    50                  55                  60

Asn Ser Gly Asn Thr Ala Thr Leu Thr Leu Thr Arg Val Glu Ala Gly
65                  70                  75                  80

Asp Glu Ala Asp Tyr Tyr Cys Gln Val Trp Asp Ser Asp Arg His His
                85                  90                  95

Val Val Phe Gly Gly Gly Thr Lys Leu Thr Val Leu
            100                 105

<210> SEQ ID NO 150
<211> LENGTH: 108
<212> TYPE: PRT
<213> ORGANISM: Artificial Sequence
<220> FEATURE:
<223> OTHER INFORMATION: Synthetic amino acid - clone name: G6
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 150

Gln Leu Val Leu Thr Gln Pro Pro Ser Val Ser Val Ser Pro Gly Gln
1               5                   10                  15

Thr Ala Ser Ile Thr Cys Ser Gly Asp Asn Leu Gly His Thr Asn Ala
            20                  25                  30

Cys Trp Tyr Gln Gln Asn Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Pro Ala Thr Leu Thr Ile Xaa Arg Val Xaa Ala Gly
65                  70                  75                  80

Asp Glu Ala Asn Tyr Tyr Cys Gln Val Trp Asp Ile Asn Asp Asp Tyr
                85                  90                  95

Ala Val Phe Gly Thr Gly Thr Xaa Leu Thr Val Leu
            100                 105

<210> SEQ ID NO 151
<211> LENGTH: 104
<212> TYPE: PRT
<213> ORGANISM: Artificial Sequence
<220> FEATURE:
<223> OTHER INFORMATION: Synthetic amino acid - clone name: C1

<400> SEQUENCE: 151

Gln Ser Val Leu Thr Gln Ser Pro Gly Thr Leu Ser Leu Ser Pro Gly
1               5                   10                  15

```
Glu Arg Ala Thr Leu Ser Cys Thr Ala Ser Gln Ser Val Ser Ser Thr
                20                  25                  30

Tyr Leu Thr Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Ser Pro
                85                  90                  95

Pro Met Tyr Thr Phe Gly Gln Leu
                100
```

```
<210> SEQ ID NO 152
<211> LENGTH: 107
<212> TYPE: PRT
<213> ORGANISM: Artificial Sequence
<220> FEATURE:
<223> OTHER INFORMATION: Synthetic amino acid - clone name: F1
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

<400> SEQUENCE: 152

Asp Ile Gln Met Thr Gln Ser Pro Ser Thr Leu Ser Ala Ser Val Gly
 1               5                  10                  15

Asp Arg Val Thr Ile Ser Cys Arg Ala Ser Gln Asn Ile Asp Tyr Asp
                20                  25                  30

Leu Ala Trp Tyr Gln Xaa Lys Pro Gly Lys Ala Pro Xaa Leu Leu Ile
            35                  40                  45

Tyr Gly Ala Ser Asn Leu Glu Gly Gly Val Pro Ser Xaa Phe Ser Gly
 50                  55                  60

Xaa Gly Ser Gly Thr Glu Phe Thr Leu Thr Ile Ser Ser Leu Gln Pro
 65                  70                  75                  80

Asp Xaa Ser Ala Thr Tyr Tyr Cys Gln Gln Tyr Val Thr Tyr Pro Leu
                85                  90                  95

Thr Phe Gly Gln Gly Thr Arg Leu Glu Ile Lys
                100                 105
```

```
<210> SEQ ID NO 153
<211> LENGTH: 111
<212> TYPE: PRT
<213> ORGANISM: Artificial Sequence
<220> FEATURE:
<223> OTHER INFORMATION: Synthetic amino acid - clone name: A3
```

<400> SEQUENCE: 153

Ala Ile Gln Met Thr Gln Ser Pro Ser Ser Leu Ser Ala Ser Val Gly
1               5                   10                  15

Asp Arg Val Thr Met Thr Cys Gln Ala Ser Gln Val Ile Asp Lys Tyr
            20                  25                  30

Val Asn Trp Tyr Arg Gln Arg Pro Gly Lys Ala Pro Glu Leu Leu Ile
        35                  40                  45

Tyr Gly Ala Ser Thr Leu Glu Ser Gly Val Pro Ser Arg Phe Ser Gly
    50                  55                  60

Ser Gly Ser Gly Thr Gln Phe Thr Phe Ser Ile Thr Ser Val Gln Pro
65                  70                  75                  80

Glu Asp Phe Ala Thr Tyr Ile Cys Gln Gln Tyr Asp Ser Val Pro Leu
                85                  90                  95

Thr Phe Gly Pro Gly Thr Ile Leu Asp Val Lys Arg Thr Val Ala
            100                 105                 110

<210> SEQ ID NO 154
<211> LENGTH: 110
<212> TYPE: PRT
<213> ORGANISM: Artificial Sequence
<220> FEATURE:
<223> OTHER INFORMATION: Synthetic amino acid - clone name: B4

<400> SEQUENCE: 154

Asp Ile Gln Leu Thr Gln Ser Pro Ser Ser Leu Ser Ala Ser Ile Gly
1               5                   10                  15

Asp Arg Val Thr Ile Thr Cys Gln Ala Ser Gln Asp Ile Phe His Tyr
            20                  25                  30

Leu Asn Trp Phe Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
    50                  55                  60

Ser Gly Ser Val Thr Asp Phe Thr Phe Thr Ile Ser Ser Leu Gln Pro
65                  70                  75                  80

Glu Asp Ile Ala Thr Tyr Tyr Cys Gln Gln Tyr Glu Asp Leu Pro Ser
                85                  90                  95

Phe Gly Gly Gly Thr Lys Val Asp Ile Lys Arg Thr Val Ala
            100                 105                 110

<210> SEQ ID NO 155
<211> LENGTH: 108
<212> TYPE: PRT
<213> ORGANISM: Artificial Sequence
<220> FEATURE:
<223> OTHER INFORMATION: Synthetic amino acid - clone name: B6

<400> SEQUENCE: 155

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Gly Ser Asn
            20                  25                  30

Tyr Leu Ala Trp Tyr Gln His Lys Pro Gly Gln Ala Pro Arg Leu Leu
        35                  40                  45

Ile Phe Ala Ala Ser Asn Arg Ala Thr Gly Ile Pro Asp Arg Phe Thr
    50                  55                  60

Gly Ser Ala Ser Gly Thr Asp Phe Thr Leu Thr Ile Asn Arg Val Glu
65                  70                  75                  80

```
Pro Glu Asp Leu Ala Val Tyr Tyr Cys Gln Gln Tyr Gly Ser Phe Pro
                85                  90                  95

Tyr Ser Phe Gly Gln Gly Thr Lys Leu Glu Ile Lys
            100                 105
```

<210> SEQ ID NO 156
<211> LENGTH: 111
<212> TYPE: PRT
<213> ORGANISM: Artificial Sequence
<220> FEATURE:
<223> OTHER INFORMATION: Synthetic amino acid - clone name: F2

<400> SEQUENCE: 156

```
Asn Ile Gln Met Thr Gln Ser Pro Ser Ser Leu Ser Ala Ser Val Gly
1               5                   10                  15

Asp Arg Val Thr Ile Thr Cys Gln Ala Ser Gln Phe Ile His Ile Tyr
                20                  25                  30

Leu Asn Trp Tyr Gln Gln Lys Leu Gly Lys Ala Pro Lys Leu Leu Ile
            35                  40                  45

Tyr Gly Ala Ser Asn Leu Glu Arg Gly Val Pro Ser Arg Phe Ser Gly
    50                  55                  60

Arg Gly Ser Glu Thr Asp Phe Thr Phe Thr Ile Asp Ser Leu Gln Pro
65                  70                  75                  80

Glu Asp Ile Ala Thr Tyr Phe Cys Gln Gln Tyr Gln Asn Pro Pro Phe
                85                  90                  95

Thr Phe Gly Gly Gly Thr Lys Val Glu Ile Asn Gly Thr Val Ala
            100                 105                 110
```

<210> SEQ ID NO 157
<211> LENGTH: 111
<212> TYPE: PRT
<213> ORGANISM: Artificial Sequence
<220> FEATURE:
<223> OTHER INFORMATION: Synthetic amino acid - clone name: D3

<400> SEQUENCE: 157

```
Ala Ile Arg Met Thr Gln Ser Pro Ser Ser Leu Ser Ala Ser Ile Gly
1               5                   10                  15

Asp Arg Ile Ser Val Thr Cys Arg Ala Ser Gln Asp Val Gly Ile Tyr
                20                  25                  30

Val Ala Trp Phe Gln Gln Lys Pro Gly Lys Pro Arg Ser Leu Ile
            35                  40                  45

Tyr Ala Ala Ser Tyr Leu Gln Thr Ala Val Pro Pro Lys Phe Arg Gly
    50                  55                  60

Ser Gly Ser Gly Thr Asp Phe Thr Leu Thr Ile Ser Asp Leu Gln Pro
65                  70                  75                  80

Asp Asp Phe Ala Thr Tyr Tyr Cys Gln Gln Tyr Lys Thr Phe Pro His
                85                  90                  95

Thr Phe Gly Gln Gly Thr Lys Leu Asp Phe Lys Arg Thr Val Ala
            100                 105                 110
```

<210> SEQ ID NO 158
<211> LENGTH: 107
<212> TYPE: PRT
<213> ORGANISM: Artificial Sequence
<220> FEATURE:
<223> OTHER INFORMATION: Synthetic amino acid - clone name: G2

<400> SEQUENCE: 158

Val Ile Trp Met Thr Gln Ser Pro Ser Thr Leu Ser Ala Ser Val Gly
1               5                   10                  15

Asp Arg Val Thr Ile Thr Cys Arg Ala Ser Gln Asp Ile Asn Thr Trp
            20                  25                  30

Leu Ala Trp Tyr Gln Gln Lys Pro Gly Lys Ala Pro Lys Leu Leu Met
        35                  40                  45

Phe Lys Val Ser Thr Leu Glu Ser Gly Asp Phe Ser Arg Phe Ser Gly
50                  55                  60

Ser Gly Ser Gly Thr Glu Phe Thr Leu Thr Val Ser Ser Leu Gln Pro
65                  70                  75                  80

Asp Asp Ser Ala Ile Tyr Tyr Cys Gln Gln Tyr His Ser Tyr Pro Tyr
                85                  90                  95

Thr Phe Gly Gln Gly Thr Arg Leu Glu Ile Lys
            100                 105

<210> SEQ ID NO 159
<211> LENGTH: 107
<212> TYPE: PRT
<213> ORGANISM: Artificial Sequence
<220> FEATURE:
<223> OTHER INFORMATION: Synthetic amino acid - clone name: A4

<400> SEQUENCE: 159

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Trp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Asn Val Leu Arg
                85                  90                  95

Thr Phe Gly Gln Gly Thr Lys Val Glu Ile Lys
            100                 105

<210> SEQ ID NO 160
<211> LENGTH: 106
<212> TYPE: PRT
<213> ORGANISM: Artificial Sequence
<220> FEATURE:
<223> OTHER INFORMATION: Synthetic amino acid - clone name: G4
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid

<400> SEQUENCE: 160

Glu Ile Val Met Thr Xaa Ser Pro Ala Thr Leu Ser Val Ser Pro Gly
1               5                   10                  15

Glu Arg Val Thr Leu Ser Cys Arg Val Ser Gln Asn Val Phe Ser Asp
            20                  25                  30

```
Leu Ala Trp Tyr Gln Arg Lys Thr Gly Gln Ser Pro Arg Leu Leu Ile
             35                  40                  45

His Gly Ala Ser Thr Arg Ala Thr Gly Ile Pro Thr Arg Phe Ser Gly
 50                  55                  60

Ser Gly Ser Gly Thr Glu Phe Thr Leu Thr Ile Ser Ser Leu Xaa Ser
 65                  70                  75                  80

Asp Asp Phe Ala Val Tyr Tyr Cys Gln Gln Tyr Asn Lys Trp Pro Thr
                 85                  90                  95

Phe Gly Gln Gly Thr Lys Val Glu Ile Lys
                100                 105

<210> SEQ ID NO 161
<211> LENGTH: 112
<212> TYPE: PRT
<213> ORGANISM: Artificial Sequence
<220> FEATURE:
<223> OTHER INFORMATION: Synthetic amino acid - clone name: D5

<400> SEQUENCE: 161

Ala Ile Gln Leu Thr Gln Ser Pro Ser Ser Leu Ser Ala Ser Val Gly
 1               5                  10                  15

Asp Arg Val Asn Ile Thr Cys Arg Ala Ser Asp Asn Ile Gly Asn Tyr
             20                  25                  30

Leu Asn Trp Tyr Gln His Lys Pro Gly Lys Ala Pro Thr Val Leu Ile
             35                  40                  45

Tyr Ala Ala Ser Thr Leu His Tyr Gly Val Pro Ser Arg Phe Ser Gly
 50                  55                  60

Arg Gly Ser Gly Thr Asp Phe Thr Val Thr Ile Ser Ser Leu Arg Ser
 65                  70                  75                  80

Asp Asp Phe Ala Val Tyr Tyr Cys Gln Gln Tyr Tyr Asn Trp Pro Pro
                 85                  90                  95

Trp Thr Phe Gly Gln Gly Thr Thr Val Asp Ile Lys Arg Thr Val Ala
                100                 105                 110

<210> SEQ ID NO 162
<211> LENGTH: 106
<212> TYPE: PRT
<213> ORGANISM: Artificial Sequence
<220> FEATURE:
<223> OTHER INFORMATION: Synthetic amino acid - clone name: A1

<400> SEQUENCE: 162

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Phe
             20                  25                  30

Leu Ala Trp Tyr Gln Gln Lys Pro Gly Gln Ala Pro Arg Leu Leu Ile
             35                  40                  45

Phe Glu Ala Ser Thr Arg Ala Thr Gly Ile Ser Ala Arg Phe Ser Gly
 50                  55                  60

Ser Gly Ser Gly Thr Asp Phe Thr Leu Thr Ile Ser Thr Leu Glu Pro
 65                  70                  75                  80

Glu Asp Phe Ala Val Tyr Tyr Cys Gln Gln Arg Ser Asn Gly Val Thr
                 85                  90                  95

Phe Gly Gln Gly Thr Arg Leu Glu Ile Lys
                100                 105

<210> SEQ ID NO 163
```

```
<211> LENGTH: 111
<212> TYPE: PRT
<213> ORGANISM: Artificial Sequence
<220> FEATURE:
<223> OTHER INFORMATION: Synthetic amino acid - clone name: H2

<400> SEQUENCE: 163

Asp Ile Gln Met Thr Gln Ser Pro Ser Thr Leu Ser Ala Ser Val Gly
1               5                   10                  15

Asp Thr Val Thr Ile Thr Cys Arg Ala Thr Glu Ser Ile Ser Ile Trp
            20                  25                  30

Leu Ala Trp Tyr Gln Gln Glu Pro Gly Lys Ala Pro Asn Leu Leu Val
        35                  40                  45

Ser Gln Ala Ser Ser Leu Lys Thr Gly Val Pro Ser Arg Phe Ser Ala
    50                  55                  60

Ser Gly Ser Gly Thr Glu Phe Thr Leu Thr Ile Ser Ser Leu His Pro
65                  70                  75                  80

Asp Asp Phe Ala Thr Tyr Val Cys Gln His Tyr His Thr Tyr Pro Phe
                85                  90                  95

Thr Phe Gly Pro Gly Thr Lys Val Asp Met Lys Arg Thr Val Ala
            100                 105                 110

<210> SEQ ID NO 164
<211> LENGTH: 116
<212> TYPE: PRT
<213> ORGANISM: Artificial Sequence
<220> FEATURE:
<223> OTHER INFORMATION: Synthetic amino acid - clone name: E2
<220> FEATURE:
<221> NAME/KEY: misc_feature
<222> LOCATION: (11)..(11)
<223> OTHER INFORMATION: Xaa can be any naturally occurring amino acid

<400> SEQUENCE: 164

Glu Ile Val Leu Thr Gln Ser Pro Asp Ser Xaa Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Arg Leu Gln Ala Glu Asp Val Ala Val Tyr Tyr Cys Gln Gln
                85                  90                  95

Tyr Tyr Leu Thr Pro Thr Phe Thr Val Thr Phe Gly Gly Gly Thr Lys
            100                 105                 110

Leu Glu Ile Lys
        115

<210> SEQ ID NO 165
<211> LENGTH: 111
<212> TYPE: PRT
<213> ORGANISM: Artificial Sequence
<220> FEATURE:
<223> OTHER INFORMATION: Synthetic amino acid - clone name: F4

<400> SEQUENCE: 165

Asp Ile Gln Leu Thr Gln Ser Pro Ser Ser Val Ser Ala Ser Val Gly
1               5                   10                  15
```

```
Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Phe Leu Ile
        35                  40                  45

Tyr Arg Ala Thr Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Gly Asp Phe Ala Thr Tyr Tyr Cys Gln Gln Thr Asn Thr Phe Pro Leu
                 85                  90                  95

Thr Phe Gly Gly Gly Thr Lys Val Glu Val Lys Arg Thr Val Ala
            100                 105                 110
```

<210> SEQ ID NO 166
<211> LENGTH: 113
<212> TYPE: PRT
<213> ORGANISM: Artificial Sequence
<220> FEATURE:
<223> OTHER INFORMATION: Synthetic amino acid - clone name: C5

<400> SEQUENCE: 166

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Lys Lys Pro Gly Gln
        35                  40                  45

Pro Pro Lys Leu Leu Phe Tyr Trp Ala Ser Thr Arg Glu Ser Gly Val
 50                  55                  60

Ser Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr His Thr Thr Pro Tyr Thr Phe Gly Gln Gly Thr Lys Leu Glu Ile
            100                 105                 110

Lys
```

<210> SEQ ID NO 167
<211> LENGTH: 111
<212> TYPE: PRT
<213> ORGANISM: Artificial Sequence
<220> FEATURE:
<223> OTHER INFORMATION: Synthetic amino acid - clone name: E5

<400> SEQUENCE: 167

```
Val Ile Trp Met Thr Gln Ser Pro Ser Ser Leu Ser Ala Ser Val Gly
 1               5                  10                  15

Asp Arg Val Ser Ile Thr Cys Arg Ala Ser Gln Thr Phe Thr Ser His
            20                  25                  30

Leu Asn Trp Tyr Gln Gln Lys Pro Gly Gln Pro Pro Lys Leu Leu Ile
        35                  40                  45

Phe Ala Ala Ser Asn Leu Gln Ser Gly Val Pro Ser Arg Phe Ser Gly
 50                  55                  60

Ser Gly Ser Gly Thr Asp Phe Thr Leu Thr Ile Asn Gly Leu Gln Ala
 65                  70                  75                  80

Thr Asp Phe Ala Thr Tyr Tyr Cys Gln Gln Ser Phe Ser Ser Pro Trp
                 85                  90                  95
```

Thr Phe Gly Gln Gly Thr Thr Val Asp Val Lys Gly Thr Val Ala
            100                 105                 110

<210> SEQ ID NO 168
<211> LENGTH: 111
<212> TYPE: PRT
<213> ORGANISM: Artificial Sequence
<220> FEATURE:
<223> OTHER INFORMATION: Synthetic amino acid - clone name: F6

<400> SEQUENCE: 168

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Asn Val Tyr
            20                  25                  30

Leu Asn Trp Tyr Gln Gln Lys Pro Gly Lys Ala Pro Lys Leu Leu Ile
            35                  40                  45

Tyr Ser Ala Ser Thr Leu Gln Ser Gly Val Pro Ser Arg Phe Thr Gly
    50                  55                  60

Ser Gly Ser Arg Thr Asp Phe Thr Leu Thr Ile Asn Gly Leu Gln Pro
65                  70                  75                  80

Glu Asp Phe Ala Thr Tyr Tyr Cys Gln Gln Ser Phe Thr Thr Leu Val
                85                  90                  95

Thr Phe Gly Pro Gly Thr Arg Val Asp Val Thr Arg Thr Val Ala
            100                 105                 110

<210> SEQ ID NO 169
<211> LENGTH: 111
<212> TYPE: PRT
<213> ORGANISM: Artificial Sequence
<220> FEATURE:
<223> OTHER INFORMATION: Synthetic amino acid - clone name: G5

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ser
            20                  25                  30

Leu Ala Trp Tyr Gln Gln Lys Pro Gly Lys Ala Pro Lys Pro Leu Ile
            35                  40                  45

Tyr Asp Ala Ser Thr Leu Gln Thr Gly Val Pro Ser Arg Phe Ser Gly
    50                  55                  60

Arg Ala Ser Gly Thr Asp Phe Thr Leu Thr Ile Asp Ser Leu Gln Pro
65                  70                  75                  80

Glu Asp Phe Ala Thr Tyr Cys Cys Gln Gln Phe Asn Ser Tyr Pro Leu
                85                  90                  95

Ser Phe Gly Gly Gly Thr Lys Val Glu Leu Lys Arg Thr Val Ala
            100                 105                 110

<210> SEQ ID NO 170
<211> LENGTH: 116
<212> TYPE: PRT
<213> ORGANISM: Artificial Sequence
<220> FEATURE:
<223> OTHER INFORMATION: Synthetic amino acid - clone name: A5

<400> SEQUENCE: 170

Ser Tyr Glu Leu Thr Gln Pro Pro Ser Ala Ser Ala Ser Leu Gly Ala
1               5                   10                  15

Ser Val Thr Leu Thr Cys Thr Val Ser Ser Gly Tyr Arg Ser Tyr Glu
            20                  25                  30

Val Asp Trp Phe Gln Gln Arg Pro Gly Lys Gly Pro Arg Phe Val Met
            35                  40                  45

Arg Val Gly Thr Gly Gly Ile Val Gly Ser Arg Gly Asp Gly Ile Pro
        50                  55                  60

Asp Arg Phe Ser Val Trp Gly Ser Gly Leu Asn Arg Tyr Leu Thr Ile
65                  70                  75                  80

Glu Asp Ile Gln Glu Glu Asp Glu Ser Asp Tyr Tyr Cys Gly Ala Asp
                85                  90                  95

His Gly Ser Gly Ser Asn Leu Val Tyr Val Phe Gly Gly Thr Lys
            100                 105                 110

Val Thr Val Leu
        115

<210> SEQ ID NO 171
<211> LENGTH: 116
<212> TYPE: PRT
<213> ORGANISM: Artificial Sequence
<220> FEATURE:
<223> OTHER INFORMATION: Synthetic amino acid - clone name: D6

<400> SEQUENCE: 171

Gln Leu Val Leu Thr Gln Pro Pro Ser Ala Ser Ala Ser Leu Gly Ala
1               5                   10                  15

Ser Val Thr Leu Thr Cys Thr Leu Ser Ser Asp Tyr Ser Ser Tyr Asn
            20                  25                  30

Val Asp Trp Tyr Gln Gln Arg Pro Gly Met Gly Pro Arg Phe Leu Met
            35                  40                  45

Arg Val Gly Thr Gly Gly Ile Val Gly Ser Arg Gly Asp Gly Ile Pro
        50                  55                  60

Asp Arg Phe Ser Val Lys Gly Ser Gly Leu Asn Arg Tyr Leu Thr Ile
65                  70                  75                  80

Lys Asn Ile Gln Glu Glu Asp Glu Ser Asp Tyr Tyr Cys Gly Ala Asp
                85                  90                  95

His Gly Ser Gly Ser Asp Phe Val Tyr Val Phe Gly Ile Gly Thr Lys
            100                 105                 110

Leu Thr Val Leu
        115

<210> SEQ ID NO 172
<211> LENGTH: 110
<212> TYPE: PRT
<213> ORGANISM: Artificial Sequence
<220> FEATURE:
<223> OTHER INFORMATION: Synthetic amino acid - clone name: E4

<400> SEQUENCE: 172

Gln Ser Val Leu Thr Gln Pro Pro Ser Ala Ser Gly Thr Pro Gly Gln
1               5                   10                  15

Arg Val Thr Ile Ser Cys Ser Gly Ser Ser Thr Asn Ile Gly Ser Asn
            20                  25                  30

Ala Val Asn Trp Tyr Gln Gln Leu Pro Arg Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

-continued

Ser Glu Asp Glu Ala Asn Tyr Tyr Cys Ala Ala Trp Asp Asp Ser Leu
                85                  90                  95

Asn Gly Pro Val Phe Gly Gly Gly Thr Gln Leu Thr Val Leu
            100                 105                 110

<210> SEQ ID NO 173
<211> LENGTH: 110
<212> TYPE: PRT
<213> ORGANISM: Artificial Sequence
<220> FEATURE:
<223> OTHER INFORMATION: Synthetic amino acid - clone name: F5

<400> SEQUENCE: 173

Gln Ser Val Leu Thr Gln Pro Pro Ser Ala Ser Gly Thr Pro Gly Gln
1               5                   10                  15

Thr Val Ile Ile Ser Cys Ser Gly Gly Ser Asn Ile Gly Ser Asn
            20                  25                  30

Phe Gly Tyr Trp Tyr Gln Gln Phe Pro Gly Thr Ala Pro Lys Leu Leu
        35                  40                  45

Ile Tyr Thr Thr Asp Arg Arg Pro Ser Gly Val Pro Asp Arg Phe Ser
    50                  55                  60

Gly Ser Lys Ser Gly Thr Thr Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Pro Val Phe Gly Gly Gly Thr Gln Leu Thr Val Leu
            100                 105                 110

<210> SEQ ID NO 174
<211> LENGTH: 112
<212> TYPE: PRT
<213> ORGANISM: Artificial Sequence
<220> FEATURE:
<223> OTHER INFORMATION: Synthetic amino acid - clone name: G1

<400> SEQUENCE: 174

Gln Thr Val Val Thr Gln Pro Pro Ser Val Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Asp Trp Tyr Gln Gln Phe Pro Gly Ser Ala Pro Lys Leu Leu
        35                  40                  45

Ile Tyr Thr Thr Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Leu
                85                  90                  95

Ser Asn Pro Lys Trp Val Phe Gly Gly Gly Thr Lys Leu Thr Val Leu
            100                 105                 110

<210> SEQ ID NO 175
<211> LENGTH: 112
<212> TYPE: PRT
<213> ORGANISM: Artificial Sequence
<220> FEATURE:
<223> OTHER INFORMATION: Synthetic amino acid - clone name: E3

<400> SEQUENCE: 175

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Ser Trp Thr Phe Gly Gln Gly Thr Lys Leu Glu Ile Lys
            100                 105                 110

<210> SEQ ID NO 176
<211> LENGTH: 114
<212> TYPE: PRT
<213> ORGANISM: Artificial Sequence
<220> FEATURE:
<223> OTHER INFORMATION: Synthetic amino acid - clone name: A2

<400> SEQUENCE: 176

Asp Ile Cys Arg Ile Arg Pro Leu Ile Arg Leu Thr Ile Gly Thr Ile
1               5                   10                  15

Thr Ile Tyr Asn Tyr Asn Gly Cys Cys Asp Asp Thr Val Ser Thr Leu
            20                  25                  30

Pro Ala Arg His Pro Trp Thr Ala Gly Leu His Leu Gln Ser Pro Arg
        35                  40                  45

Arg Leu Met Tyr Gln Val Ser Thr Arg Asp Ser Gly Val Pro Asp Arg
    50                  55                  60

Phe Ser Gly Ser Gly Ser Gly Thr Asp Phe Thr Leu Arg Ile Ser Arg
65                  70                  75                  80

Val Glu Ala Glu Asp Val Gly Val Tyr Tyr Cys Met Gln Gly Thr His
                85                  90                  95

Trp Pro Tyr Thr Phe Gly Gln Gly Thr Lys Leu Glu Ile Arg Arg Thr
            100                 105                 110

Val Ala

<210> SEQ ID NO 177
<211> LENGTH: 112
<212> TYPE: PRT
<213> ORGANISM: Artificial Sequence
<220> FEATURE:
<223> OTHER INFORMATION: Synthetic amino acid - clone name: D1

<400> SEQUENCE: 177

Asp Ile Val Met Thr Gln Thr Pro Leu Ser Leu Ser Val Thr Pro Gly
1               5                   10                  15

Gln Pro Ala Ala Ile Ser Cys Lys Ser Ser Gln Ser Leu Val His Arg
            20                  25                  30

Asp Gly Lys Thr Tyr Leu Tyr Trp Tyr Leu Gln Lys Pro Gly His Ser
        35                  40                  45

Pro Gln Leu Leu Val Tyr Glu Ala Ser Ser Arg Phe Ser Gly Val Pro
    50                  55                  60

```
Asp Arg Ile Ser Gly Ser Ala Ser Gly Thr Gln Phe Thr Leu Asn Ile
65                  70                  75                  80

Ser Arg Val Glu Ala Glu Asp Val Gly Leu Tyr Tyr Cys Met Gln Ser
                85                  90                  95

Arg Asn Leu Pro Lys Thr Phe Gly Gln Gly Thr Lys Val Glu Ile Lys
            100                 105                 110

<210> SEQ ID NO 178
<211> LENGTH: 108
<212> TYPE: PRT
<213> ORGANISM: Artificial Sequence
<220> FEATURE:
<223> OTHER INFORMATION: Synthetic amino acid - clone name: C4

<400> SEQUENCE: 178

Ser Tyr Glu Leu Thr Gln Pro Thr Ser Leu Ser Ala Ser Pro Gly Ala
1               5                   10                  15

Ser Ala Ser Leu Thr Cys Thr Leu Ser Ser Gly Phe Asn Val Val Ser
                20                  25                  30

Tyr Asn Ile Tyr Trp Tyr Gln Gln Lys Pro Gly Ser Pro Pro Gln Tyr
            35                  40                  45

Leu Leu Arg Tyr Arg Ser Asp Ser Asp Arg His Gln Gly Ser Gly Val
    50                  55                  60

Pro Ser Arg Phe Ser Gly Ser Lys Asp Ala Ser Ala Asn Ala Gly Ile
65                  70                  75                  80

Leu Val Ile Ser Ala Leu Gln Ser Asp Glu Ala Asp Tyr Tyr Cys
                85                  90                  95

Met Val Trp Tyr Ser Ala Trp Val Phe Gly Gly Gly
            100                 105

<210> SEQ ID NO 179
<211> LENGTH: 107
<212> TYPE: PRT
<213> ORGANISM: Artificial Sequence
<220> FEATURE:
<223> OTHER INFORMATION: Synthetic amino acid - clone name: E1

<400> SEQUENCE: 179

Ser Tyr Glu Leu Thr Gln Pro Leu Ser Val Ser Val Ala Leu Gly Gln
1               5                   10                  15

Thr Ala Thr Ile Thr Cys Ala Gly Asn Asn Ile Gly Thr Tyr Tyr Val
                20                  25                  30

His Trp Tyr Gln Gln Arg Pro Gly Gln Ala Pro Val Leu Val Met Tyr
            35                  40                  45

Arg Asp Thr Asn Arg Pro Ser Gly Ile Ser Asp Arg Phe Ser Gly Ser
    50                  55                  60

Asn Ser Gly Asp Thr Ala Thr Leu Thr Ile Cys Gly Val Gln Val Gly
65                  70                  75                  80

Asp Glu Ala Asp Tyr Tyr Cys His Val Leu Asp Ser Ser Thr Ile Val
                85                  90                  95

Ile Phe Gly Gly Gly Thr Gln Leu Thr Val Leu
            100                 105

<210> SEQ ID NO 180
<211> LENGTH: 108
<212> TYPE: PRT
<213> ORGANISM: Artificial Sequence
<220> FEATURE:
<223> OTHER INFORMATION: Synthetic amino acid - clone name: A6
```

```
<400> SEQUENCE: 180

Gln Ser Val Leu Thr Gln Ser Pro Ala Thr Leu Ser Val Ser Pro Gly
1               5                   10                  15

Glu Arg Ala Ser Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys His Gln Tyr Asn Asn Trp Pro Leu
                85                  90                  95

Tyr Thr Phe Gly Gln Gly Thr Lys Leu Thr Val Leu
            100                 105

<210> SEQ ID NO 181
<211> LENGTH: 108
<212> TYPE: PRT
<213> ORGANISM: Artificial Sequence
<220> FEATURE:
<223> OTHER INFORMATION: Synthetic amino acid - clone name: H1

<400> SEQUENCE: 181

Gln Ser Val Leu Thr Gln Asp Pro Ala Val Pro Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Thr Arg Pro Ser Gly Ile Pro Val Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Tyr Leu
                85                  90                  95

Leu Leu Phe Gly Thr Gly Thr Lys Leu Thr Val Leu
            100                 105

<210> SEQ ID NO 182
<211> LENGTH: 109
<212> TYPE: PRT
<213> ORGANISM: Artificial Sequence
<220> FEATURE:
<223> OTHER INFORMATION: Synthetic amino acid - clone name: B2

<400> SEQUENCE: 182

Gln Ala Val Leu Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Ala Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80
```

Gln Pro Glu Asp Glu Ala Glu Tyr Tyr Cys Leu Leu Ser Tyr Ser Gly
                85                  90                  95

Ala Gly Val Phe Gly Thr Gly Thr Lys Val Thr Val Leu
            100                 105

<210> SEQ ID NO 183
<211> LENGTH: 111
<212> TYPE: PRT
<213> ORGANISM: Artificial Sequence
<220> FEATURE:
<223> OTHER INFORMATION: Synthetic amino acid - clone name: C2

<400> SEQUENCE: 183

Asp Ile Gln Met Thr Gln Ser Pro Ser Ser Leu Ser Ala Ser Val Gly
1               5                   10                  15

Asp Arg Val Ala Ile Ala Cys Arg Pro Ser Gln Asp Ile Gly Thr Asp
            20                  25                  30

Leu Gly Trp Tyr Gln Gln Lys Pro Gly Lys Ala Pro Lys Leu Leu Ile
        35                  40                  45

Phe Asp Ser Ser Thr Leu Gln Ser Gly Val Pro Ser Arg Phe Ser Gly
    50                  55                  60

Ser Leu Ser Gly Thr Asp Phe Ile Leu Thr Ile Thr Asn Leu Gln Pro
65                  70                  75                  80

Glu Asp Phe Ala Thr Tyr Tyr Cys Leu Gln Asp Tyr Ser Phe Pro Tyr
                85                  90                  95

Thr Phe Gly Gln Gly Thr Lys Leu Gln Ile Lys Arg Thr Val Ala
            100                 105                 110

<210> SEQ ID NO 184
<211> LENGTH: 106
<212> TYPE: PRT
<213> ORGANISM: Artificial Sequence
<220> FEATURE:
<223> OTHER INFORMATION: Synthetic amino acid - clone name: G3

<400> SEQUENCE: 184

Ser Tyr Val Leu Thr Gln Pro Pro Ser Val Ser Val Ser Pro Gly Gln
1               5                   10                  15

Thr Ala Ser Ile Thr Cys Ser Gly Asp Glu Leu Lys Tyr Lys Tyr Thr
            20                  25                  30

Cys Trp Tyr His Gln Lys Pro Gly Gln Ser Pro Val Leu Leu Ile Tyr
        35                  40                  45

Gln Asp Thr Lys Arg Pro Ser Gly Ile Pro Glu Arg Phe Ser Gly Ser
    50                  55                  60

Arg Ser Glu Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser His Ala Val
                85                  90                  95

Phe Gly Arg Gly Thr Gln Leu Thr Val Leu
            100                 105

<210> SEQ ID NO 185
<211> LENGTH: 106
<212> TYPE: PRT
<213> ORGANISM: Artificial Sequence
<220> FEATURE:
<223> OTHER INFORMATION: Synthetic amino acid - clone name: H3

<400> SEQUENCE: 185

Ser Tyr Val Leu Thr Gln Pro Pro Ser Val Ser Val Phe Pro Gly Gln
1               5                   10                  15

Thr Ala Arg Ile Thr Cys Ser Gly Ser Thr Phe Pro Lys Leu Tyr Ser
            20                  25                  30

Phe Trp Tyr Gln Gln Lys Thr Gly Gln Ala Pro Leu Leu Val Ile Tyr
        35                  40                  45

Lys Asp Thr Glu Arg Pro Ser Gly Ile Pro Glu Arg Phe Ser Gly Ser
    50                  55                  60

Thr Ser Gly Thr Thr Val Thr Leu Ile Ile Ser Gly Val Gln Pro Glu
65                  70                  75                  80

Asp Asp Ala Asp Tyr Tyr Cys Gln Ser Glu Asp Ser Arg Gly Pro Val
                85                  90                  95

Phe Gly Gly Gly Thr Lys Val Thr Val Leu
            100                 105

<210> SEQ ID NO 186
<211> LENGTH: 112
<212> TYPE: PRT
<213> ORGANISM: Artificial Sequence
<220> FEATURE:
<223> OTHER INFORMATION: Synthetic amino acid - clone name: D4

<400> SEQUENCE: 186

Gly Val Val Met Thr Gln Thr Pro Leu Ser Ser Leu Val Thr Leu Gly
1               5                   10                  15

Gln Pro Ala Ser Ile Ser Cys Arg Ser Ser Glu Ser Val Val His Asp
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Pro Glu Asp Val Gly Val Tyr Tyr Cys Val Gln Ala
                85                  90                  95

Thr His Phe Pro Val Thr Phe Gly Gly Gly Thr Arg Val Glu Ile Lys
            100                 105                 110

<210> SEQ ID NO 187
<211> LENGTH: 111
<212> TYPE: PRT
<213> ORGANISM: Artificial Sequence
<220> FEATURE:
<223> OTHER INFORMATION: Synthetic amino acid - clone name: C6

<400> SEQUENCE: 187

Gln Ser Ala Leu Thr Gln Pro Ala Ser Val Ser Ala Ser Pro Gly Gln
1               5                   10                  15

Ser Val Thr Ile Ser Cys Thr Gly Thr Ser Asp Asp Val Gly Arg Tyr
            20                  25                  30

Asp Tyr Val Ser Trp Tyr Gln Gln His Pro Gly Gly Ala Pro Lys Leu
        35                  40                  45

Ile Leu Tyr Asp Val Asn Arg Arg Pro Ser Gly Val Ser Asp Arg Phe
    50                  55                  60

Ser Gly Ser Lys Ser Ala Asn Lys Ala Ser Leu Thr Ile Ser Gly Leu
65                  70                  75                  80

```
Gln Ala Asp Asp Glu Gly Asp Tyr Tyr Cys Cys Ser Tyr Thr Thr Gly
                85                  90                  95

Ser Thr Leu Tyr Leu Phe Gly Thr Gly Thr Gln Leu Thr Val Leu
               100             105                 110
```